(12) United States Patent
Kaiser et al.

(10) Patent No.: US 9,408,599 B2
(45) Date of Patent: *Aug. 9, 2016

(54) METHOD AND APPARATUS FOR COUPLING SOFT TISSUE TO A BONE

(75) Inventors: Ryan A. Kaiser, Leesburg, IN (US); Kevin T. Stone, Winona Lake, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 1122 days.

This patent is subject to a terminal disclaimer.

(21) Appl. No.: 13/311,936

(22) Filed: Dec. 6, 2011

(65) Prior Publication Data

US 2012/0095470 A1    Apr. 19, 2012

Related U.S. Application Data

(63) Continuation-in-part of application No. 12/474,802, filed on May 29, 2009, now Pat. No. 8,088,130, which is a continuation-in-part of application No. 11/541,506, filed on Sep. 29, 2006, now Pat. No.

(Continued)

(51) Int. Cl.
| | |
|---|---|
| *A61B 17/10* | (2006.01) |
| *A61B 17/04* | (2006.01) |
| *A61B 17/16* | (2006.01) |
| *A61B 17/00* | (2006.01) |

(Continued)

(52) U.S. Cl.
CPC ....... *A61B 17/0401* (2013.01); *A61B 17/06166* (2013.01); *A61B 17/1617* (2013.01);

(Continued)

(58) Field of Classification Search
CPC ........... A61B 17/0401; A61B 17/1617; A61B 17/1675; A61B 17/06166; A61F 2/0805; A61F 2/0811; Y10T 408/9048; Y10T 408/9045; Y10T 409/300056; Y10T 409/300112

See application file for complete search history.

(56) References Cited

U.S. PATENT DOCUMENTS

| | | |
|---|---|---|
| 394,739 A | 12/1888 | Toulmin |
| 3,081,781 A | 3/1963 | Sterrner |

(Continued)

FOREIGN PATENT DOCUMENTS

| | | |
|---|---|---|
| EP | 0019062 A1 | 11/1980 |
| EP | 1864617 B1 | 10/2009 |

(Continued)

OTHER PUBLICATIONS

International Search Report and Written Opinion mailed May 23, 2012 for PCT/US2012/030294 claiming benefit of U.S. Appl. No. 13/071,563, filed Mar. 25, 2011.

(Continued)

*Primary Examiner* — Gregory Anderson
*Assistant Examiner* — Son Dang
(74) *Attorney, Agent, or Firm* — Schwegman Lundberg & Woessner, P.A.

(57) ABSTRACT

A method and apparatus for coupling a soft tissue implant into a locking cavity formed within a bone is disclosed. The method includes bringing a bone cutting tool extending along a longitudinal axis into engagement with an outer surface of the bone. The bone cutting tool is rotated about the longitudinal axis while driving it from the outer surface of the bone to a predetermined depth in the bone to form a bore. The bone cutting tool is then continuously rotated at the predetermined depth to establish an enlarged bone pocket at a distal end of the bore. The bone pocket defines a shoulder extending around a circumference between the bone pocket and bore. The bone cutting tool is removed from the bone pocket and bore. The fixation device is then inserted into the bone pocket through the bore, where it is seated against the bone pocket shoulder.

20 Claims, 53 Drawing Sheets

Related U.S. Application Data 7,601,165, and a continuation-in-part of application No. 11/541,505, filed on Sep. 29, 2006, now Pat. No. 7,658,751, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned, and application No. 13/311,936, Dec. 6, 2011, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 13/071,563, filed on Mar. 25, 2011.

(51) Int. Cl.
A61B 17/06 (2006.01)
A61F 2/08 (2006.01)

(52) U.S. Cl.
CPC ........... *A61B17/1675* (2013.01); *A61F 2/0805* (2013.01); *A61F 2/0811* (2013.01); *A61B 17/0469* (2013.01); *A61B 17/0485* (2013.01); *A61B 17/0487* (2013.01); *A61B 17/1631* (2013.01); *A61B 17/1633* (2013.01); *A61B 17/1655* (2013.01); *A61B 2017/00004* (2013.01); *A61B 2017/00336* (2013.01); *A61B 2017/00858* (2013.01); *A61B 2017/044* (2013.01); *A61B 2017/0406* (2013.01); *A61B 2017/0409* (2013.01); *A61B 2017/0414* (2013.01); *A61B 2017/0417* (2013.01); *A61B 2017/0432* (2013.01); *A61B 2017/0477* (2013.01); *A61B 2017/0496* (2013.01); *A61B 2017/06185* (2013.01); *A61F 2/08* (2013.01); *A61F 2002/0829* (2013.01); *A61F 2002/0835* (2013.01); *A61F 2002/0852* (2013.01); *A61F 2002/0864* (2013.01); *A61F 2002/0882* (2013.01); *A61F 2002/0888* (2013.01)

(56) References Cited

U.S. PATENT DOCUMENTS

| | | | |
|---|---|---|---|
| 3,650,274 A | 3/1972 | Edwards et al. | |
| 4,146,022 A | 3/1979 | Johnson et al. | |
| 4,158,250 A | 6/1979 | Ringwald | |
| 4,275,490 A | 6/1981 | Bivins | |
| 4,388,921 A | 6/1983 | Sutter et al. | |
| 4,489,464 A | 12/1984 | Massari et al. | |
| 4,736,746 A | 4/1988 | Anderson | |
| 4,738,255 A | 4/1988 | Goble et al. | |
| 4,751,922 A | 6/1988 | DiPietropolo | |
| 4,790,850 A | 12/1988 | Dunn et al. | |
| 4,858,603 A | 8/1989 | Clemow et al. | |
| 4,884,572 A | 12/1989 | Bays et al. | |
| 4,889,110 A | 12/1989 | Galline et al. | |
| 4,974,488 A | 12/1990 | Spralja | |
| 5,020,713 A | 6/1991 | Kunreuther | |
| 5,064,431 A | 11/1991 | Gilbertson et al. | |
| 5,171,274 A | 12/1992 | Fluckiger et al. | |
| 5,190,545 A | 3/1993 | Corsi et al. | |
| 5,199,135 A | 4/1993 | Gold | |
| 5,415,658 A | 5/1995 | Kilpela et al. | |
| 5,417,690 A | 5/1995 | Sennett et al. | |
| 5,423,824 A * | 6/1995 | Akerfeldt et al. | 606/80 |
| 5,441,508 A | 8/1995 | Gazielly et al. | |
| 5,456,721 A | 10/1995 | Legrand | |
| 5,464,426 A | 11/1995 | Bonutti | |
| 5,495,974 A | 3/1996 | Deschenes et al. | |
| 5,531,759 A | 7/1996 | Kensey et al. | |
| 5,549,630 A | 8/1996 | Bonutti | |
| 5,573,547 A | 11/1996 | LeVeen et al. | |
| 5,607,430 A | 3/1997 | Bailey | |
| 5,649,960 A | 7/1997 | Pavletic | |
| 5,715,578 A | 2/1998 | Knudson | |
| 5,725,557 A | 3/1998 | Gatturna et al. | |
| 5,741,259 A | 4/1998 | Chan | |
| 5,797,913 A | 8/1998 | Dambreville et al. | |
| 5,817,095 A | 10/1998 | Smith | |
| 5,824,066 A | 10/1998 | Gross | |
| 5,836,955 A | 11/1998 | Buelna et al. | |
| 5,849,012 A | 12/1998 | Abboudi | |
| 5,885,294 A | 3/1999 | Pedlick et al. | |
| 5,935,134 A | 8/1999 | Pedlick et al. | |
| 5,980,548 A | 11/1999 | Evans et al. | |
| 5,989,252 A | 11/1999 | Fumex | |
| 6,036,695 A | 3/2000 | Smith | |
| 6,041,485 A * | 3/2000 | Pedlick et al. | 29/450 |
| 6,110,207 A | 8/2000 | Eichhorn et al. | |
| 6,136,010 A | 10/2000 | Modesitt et al. | |
| 6,334,064 B1 | 12/2001 | Fiddian-Green | |
| 6,368,326 B1 | 4/2002 | Dakin et al. | |
| 6,425,924 B1 | 7/2002 | Rousseau | |
| 6,485,504 B1 | 11/2002 | Johnson et al. | |
| RE37,963 E | 1/2003 | Thal | |
| 6,511,498 B1 | 1/2003 | Fumex | |
| 6,514,274 B1 | 2/2003 | Boucher et al. | |
| 6,543,094 B2 | 4/2003 | D'addario | |
| 6,554,852 B1 | 4/2003 | Oberlander | |
| 6,592,609 B1 | 7/2003 | Bonutti | |
| 6,626,930 B1 | 9/2003 | Allen et al. | |
| 6,638,286 B1 | 10/2003 | Burbank et al. | |
| 6,645,211 B2 | 11/2003 | Magana | |
| 6,648,921 B2 | 11/2003 | Anderson et al. | |
| 6,669,707 B1 | 12/2003 | Swanstrom et al. | |
| 6,682,533 B1 | 1/2004 | Dinsdale et al. | |
| 6,712,859 B2 | 3/2004 | Rousseau | |
| 6,730,124 B2 | 5/2004 | Steiner | |
| 6,755,868 B2 | 6/2004 | Rousseau | |
| 6,790,210 B1 | 9/2004 | Cragg et al. | |
| 6,793,595 B1 | 9/2004 | Monnet | |
| 7,083,638 B2 | 8/2006 | Foerster | |
| 7,207,993 B1 | 4/2007 | Baldwin et al. | |
| 7,303,577 B1 | 12/2007 | Dean | |
| 7,481,814 B1 | 1/2009 | Metzger | |
| 7,485,149 B1 | 2/2009 | White | |
| 7,572,275 B2 | 8/2009 | Fallin et al. | |
| 7,601,165 B2 | 10/2009 | Stone | |
| 7,658,751 B2 | 2/2010 | Stone et al. | |
| 7,703,372 B1 | 4/2010 | Shakespeare | |
| 7,749,250 B2 | 7/2010 | Stone et al. | |
| 7,762,942 B2 | 7/2010 | Neisz et al. | |
| 7,790,945 B1 | 9/2010 | Watson, Jr. | |
| 7,828,820 B2 | 11/2010 | Stone et al. | |
| 7,856,698 B2 | 12/2010 | Hays | |
| 7,857,830 B2 | 12/2010 | Stone et al. | |
| 7,867,252 B2 * | 1/2011 | Criscuolo et al. | 606/232 |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,914,539 B2 | 3/2011 | Stone et al. | |
| 7,959,650 B2 | 6/2011 | Kaiser et al. | |
| 8,034,090 B2 | 10/2011 | Stone et al. | |
| 8,088,130 B2 | 1/2012 | Kaiser et al. | |
| 8,118,835 B2 | 2/2012 | Weisel et al. | |
| 8,118,836 B2 | 2/2012 | Denham et al. | |

(56) References Cited

U.S. PATENT DOCUMENTS

| | | |
|---|---|---|
| 8,118,868 B2 | 2/2012 | May et al. |
| 8,128,658 B2 | 3/2012 | Kaiser et al. |
| 8,137,382 B2 | 3/2012 | Denham et al. |
| 8,177,810 B2 | 5/2012 | Ferree |
| 8,231,654 B2 | 7/2012 | Kaiser et al. |
| 8,251,998 B2 | 8/2012 | Hoeppner et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,721,684 B2 | 5/2014 | Denham et al. |
| 8,771,316 B2 | 7/2014 | Denham et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,968,364 B2 | 3/2015 | Berelsman |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,078,644 B2 | 7/2015 | Stone |
| 9,149,267 B2 | 10/2015 | Norton et al. |
| 9,173,651 B2 | 11/2015 | Stone et al. |
| 9,198,673 B2 | 12/2015 | Stone |
| 9,216,078 B2 | 12/2015 | Conner et al. |
| 2001/0041916 A1 | 11/2001 | Bonutti |
| 2001/0051815 A1 | 12/2001 | Esplin |
| 2002/0019649 A1 | 2/2002 | Sikora et al. |
| 2002/0068254 A1 | 6/2002 | Campbell |
| 2002/0156475 A1 | 10/2002 | Lerch et al. |
| 2002/0177853 A1 | 11/2002 | Chervitz et al. |
| 2003/0105489 A1 | 6/2003 | Eichhorn et al. |
| 2003/0139752 A1 | 7/2003 | Pasricha et al. |
| 2003/0139775 A1 | 7/2003 | Grafton |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0220646 A1* | 11/2003 | Thelen ............... A61B 17/1642 606/79 |
| 2003/0229361 A1 | 12/2003 | Jackson |
| 2003/0236555 A1 | 12/2003 | Thornes |
| 2004/0073176 A1 | 4/2004 | Utterberg |
| 2004/0127907 A1 | 7/2004 | Dakin et al. |
| 2004/0138683 A1 | 7/2004 | Shelton et al. |
| 2004/0204722 A1 | 10/2004 | Sikora et al. |
| 2004/0225305 A1 | 11/2004 | Ewers et al. |
| 2004/0267317 A1 | 12/2004 | Higgins et al. |
| 2005/0004670 A1 | 1/2005 | Gebhardt et al. |
| 2005/0033363 A1 | 2/2005 | Bojarski et al. |
| 2005/0049598 A1 | 3/2005 | West, Jr. et al. |
| 2005/0076478 A1 | 4/2005 | Miyazaki et al. |
| 2005/0090827 A1 | 4/2005 | Gedebou |
| 2005/0137624 A1 | 6/2005 | Fallman |
| 2005/0149118 A1 | 7/2005 | Koyfman et al. |
| 2005/0187577 A1 | 8/2005 | Selvitelli et al. |
| 2005/0192632 A1 | 9/2005 | Geissler et al. |
| 2005/0251153 A1 | 11/2005 | Sakamoto et al. |
| 2005/0251159 A1 | 11/2005 | Ewers et al. |
| 2005/0251209 A1 | 11/2005 | Saadat et al. |
| 2006/0004364 A1 | 1/2006 | Green et al. |
| 2006/0030884 A1 | 2/2006 | Yeung et al. |
| 2006/0149266 A1 | 7/2006 | Cordasco |
| 2006/0189993 A1 | 8/2006 | Stone |
| 2006/0190042 A1 | 8/2006 | Stone et al. |
| 2006/0195106 A1 | 8/2006 | Jones et al. |
| 2006/0212055 A1 | 9/2006 | Karabey et al. |
| 2006/0229623 A1 | 10/2006 | Bonutti et al. |
| 2006/0229676 A1 | 10/2006 | Doll et al. |
| 2006/0253130 A1 | 11/2006 | Wolniewicz, II |
| 2006/0259076 A1 | 11/2006 | Burkhart |
| 2006/0264944 A1 | 11/2006 | Cole |
| 2006/0276896 A1 | 12/2006 | Fallin et al. |
| 2006/0282085 A1 | 12/2006 | Stone |
| 2007/0005068 A1 | 1/2007 | Sklar |
| 2007/0010857 A1 | 1/2007 | Sugimoto et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0043371 A1 | 2/2007 | Teague |
| 2007/0071568 A1 | 3/2007 | Dorstewitz |
| 2007/0073319 A1 | 3/2007 | Mikkaichi et al. |
| 2007/0073322 A1 | 3/2007 | Mikkaichi et al. |
| 2007/0088362 A1 | 4/2007 | Bonutti et al. |
| 2007/0112384 A1 | 5/2007 | Conlon et al. |
| 2007/0123984 A1 | 5/2007 | Hodorek |
| 2007/0156174 A1 | 7/2007 | Kaiser et al. |
| 2007/0167950 A1 | 7/2007 | Tauro et al. |
| 2007/0219558 A1 | 9/2007 | Deutsch |
| 2007/0225715 A1 | 9/2007 | Deffenbaugh et al. |
| 2007/0250059 A1 | 10/2007 | Weisshaupt et al. |
| 2007/0265704 A1 | 11/2007 | Mayer et al. |
| 2007/0288023 A1 | 12/2007 | Pellegrino et al. |
| 2008/0027440 A1 | 1/2008 | Marissen et al. |
| 2008/0082128 A1 | 4/2008 | Stone |
| 2008/0177302 A1 | 7/2008 | Shurnas |
| 2008/0208252 A1 | 8/2008 | Holmes |
| 2008/0255613 A1 | 10/2008 | Kaiser et al. |
| 2008/0319478 A1 | 12/2008 | Foerster et al. |
| 2009/0018655 A1 | 1/2009 | Brunelle et al. |
| 2009/0062847 A1 | 3/2009 | Ken |
| 2009/0082790 A1 | 3/2009 | Shad et al. |
| 2009/0105717 A1 | 4/2009 | Bluechel |
| 2009/0138002 A1 | 5/2009 | Fenton |
| 2009/0240335 A1 | 9/2009 | Arcenio et al. |
| 2009/0265015 A1 | 10/2009 | May et al. |
| 2009/0287215 A1 | 11/2009 | Fisher et al. |
| 2009/0312793 A1 | 12/2009 | Huxel et al. |
| 2010/0016899 A1 | 1/2010 | Gelfand |
| 2010/0063541 A1 | 3/2010 | Brunelle et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0152752 A1 | 6/2010 | Denove et al. |
| 2010/0204700 A1 | 8/2010 | Falahee |
| 2010/0211071 A1 | 8/2010 | Lettmann et al. |
| 2010/0211075 A1 | 8/2010 | Stone |
| 2011/0087225 A1 | 4/2011 | Fritzinger |
| 2011/0098727 A1 | 4/2011 | Kaiser et al. |
| 2011/0106153 A1 | 5/2011 | Stone et al. |
| 2011/0112538 A1 | 5/2011 | Dell'oca |
| 2012/0041486 A1 | 2/2012 | Stone et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0095470 A1 | 4/2012 | Kaiser et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2013/0023930 A1 | 1/2013 | Stone et al. |

(56) References Cited

U.S. PATENT DOCUMENTS

| | | |
|---|---|---|
| 2013/0035698 A1 | 2/2013 | Stone et al. |
| 2013/0046341 A1 | 2/2013 | Stone et al. |
| 2013/0116730 A1 | 5/2013 | Denham et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0317621 A1 | 11/2013 | Metzger et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0276992 A1 | 9/2014 | Stone et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |

FOREIGN PATENT DOCUMENTS

| | | |
|---|---|---|
| WO | WO-2007119057 A1 | 10/2007 |
| WO | WO-2010138832 A1 | 12/2010 |
| WO | WO-2012134999 A1 | 10/2012 |

OTHER PUBLICATIONS

International Preliminary Report on Patentability mailed Oct. 10, 2013 for PCT/US2012/030294 which claims benefit of U.S. Appl. No. 13/071,563, filed Mar. 25, 2011.

"U.S. Appl. No. 11/504,882, Supplemental Notice of Allowability mailed Mar. 12, 2015", 5 pgs.

"U.S. Appl. No. 12/719,337, Notice of Allowance mailed Mar. 11, 2015", 10 pgs.

"U.S. Appl. No. 13/098,927, Response filed Jul. 22, 2015 to Final Office Action mailed May 22, 2013", 17 pgs.

"U.S. Appl. No. 13/281,009, Non Final Office Action mailed Jun. 2, 2015", 9 pgs.

"U.S. Appl. No. 13/281,009, Notice of Allowance mailed Oct. 29, 2015", 8 pgs.

"U.S. Appl. No. 13/281,009, Response filed Sep. 2, 2015 to Non Final Office Action mailed Jun. 2, 2015", 13 pgs.

"U.S. Appl. No. 13/281,009, Restriction Requirement mailed Feb. 11, 2015", 6 pgs.

"U.S. Appl. No. 13/288,459, Examiner Interview Summary mailed Feb. 6, 2015", 3 pgs.

"U.S. Appl. No. 13/288,459, Non Final Office Action mailed Jun. 24, 2015", 10 pgs.

"U.S. Appl. No. 13/288,459, Notice of Allowance mailed Jan. 11, 2016", 13 pgs.

"U.S. Appl. No. 13/288,459, Response filed Mar. 3, 2015 to Non Final Office Action mailed Nov. 4, 2014", 16 pgs.

"U.S. Appl. No. 13/288,459, Response filed Oct. 23, 2015 to Non Final Office Action mailed Jun. 24, 2015", 14 pgs.

"U.S. Appl. No. 13/293,825, Notice of Allowability mailed Jun. 22, 2015", 7 pgs.

"U.S. Appl. No. 13/293,825, Notice of Allowance mailed May 19, 2015", 9 pgs.

"U.S. Appl. No. 13/293,825, Response filed Apr. 15, 2015 to Restriction Requirement mailed Feb. 12, 2015", 17 pgs.

"U.S. Appl. No. 13/293,825, Restriction Requirement mailed Feb. 12, 2015", 9 pgs.

"U.S. Appl. No. 13/295,126, Non Final Office Action mailed May 19, 2015", 9 pgs.

"U.S. Appl. No. 13/295,126, Notice of Allowance mailed Oct. 22, 2015", 9 pgs.

"U.S. Appl. No. 13/295,126, Response filed Apr. 13, 2015 to Restriction Requirement mailed Feb. 12, 2015", 1 pgs.

"U.S. Appl. No. 13/295,126, Response filed Aug. 17, 2015 to Non Final Office Action mailed May 19, 2015", 21 pgs.

"U.S. Appl. No. 13/295,126, Restriction Requirement mailed Feb. 12, 2015", 9 pgs.

"U.S. Appl. No. 13/350,985, Final Office Action mailed Apr. 16, 2015", 8 pgs.

"U.S. Appl. No. 13/350,985, Notice of Allowance mailed Jul. 27, 2015", 5 pgs.

"U.S. Appl. No. 13/350,985, Response filed Mar. 13, 2015 to Non Final Office Action mailed Dec. 15, 2014", 10 pgs.

"U.S. Appl. No. 13/350,985, Response filed Jul. 9, 2015 to Final Office Action mailed Apr. 16, 2015", 8 pgs.

"U.S. Appl. No. 13/625,413, Final Office Action mailed Oct. 30, 2015", 8 pgs.

"U.S. Appl. No. 13/625,413, Non Final Office Action mailed Jun. 8, 2015", 11 pgs.

"U.S. Appl. No. 13/625,413, Notice of Allowance mailed Dec. 11, 2015", 9 pgs.

"U.S. Appl. No. 13/625,413, Response filed May 11, 2015 to Restriction Requirement mailed Mar. 10, 2015", 1 pg.

"U.S. Appl. No. 13/625,413, Response filed Sep. 8, 2015 to Non Final Office Action mailed Jun. 8, 2015", 16 pgs.

"U.S. Appl. No. 13/625,413, Response filed Dec. 1, 2015 to Final Office Action mailed Oct. 30, 2015", 9 pgs.

"U.S. Appl. No. 13/625,413, Restriction Requirement mailed Mar. 10, 2015", 7 pgs.

"U.S. Appl. No. 13/645,964, Final Office Action mailed Oct. 6, 2015", 17 pgs.

"U.S. Appl. No. 13/645,964, Non Final Office Action mailed Mar. 17, 2015", 15 pgs.

"U.S. Appl. No. 13/645,964, Response filed Jul. 17, 2015 to Non Final Office Action mailed Mar. 17, 2015", 17 pgs.

"U.S. Appl. No. 13/645,964, Response filed Dec. 4, 2015 to Final Office Action mailed Oct. 6, 2015", 14 pgs.

"U.S. Appl. No. 13/656,821, Notice of Allowance mailed Jun. 18, 2015", 11 pgs.

"U.S. Appl. No. 13/656,821, Response filed May 11, 2015 to Restriction Requirement mailed Mar. 10, 2015", 1 pg.

"U.S. Appl. No. 13/656,821, Restriction Requirement mailed Mar. 10, 2015", 6 pgs.

"U.S. Appl. No. 13/720,648, Final Office Action mailed Nov. 16, 2015", 7 pgs.

"U.S. Appl. No. 13/720,648, Non Final Office Action mailed Jun. 10, 2015", 11 pgs.

"U.S. Appl. No. 13/720,648, Response filed Jan. 13, 2016 to Final Office Action mailed Nov. 16, 2015", 9 pgs.

"U.S. Appl. No. 13/720,648, Response filed May 11, 2015 to Restriction Requirement mailed Mar. 10, 2015", 8 pgs.

"U.S. Appl. No. 13/720,648, Response filed Oct. 9, 2015 to Non Final Office Action mailed Jun. 10, 2015", 12 pgs.

"U.S. Appl. No. 13/720,648, Restriction Requirement mailed Mar. 10, 2015", 8 pgs.

"U.S. Appl. No. 13/751,846, Final Office Action mailed Nov. 17, 2015", 9 pgs.

"U.S. Appl. No. 13/751,846, Non Final Office Action mailed Jun. 15, 2015", 10 pgs.

"U.S. Appl. No. 13/751,846, Response filed May 11, 2015 to Restriction Requirement mailed Mar. 10, 2015", 15 pgs.

"U.S. Appl. No. 13/751,846, Response filed Oct. 9, 2015 to Non Final Office Action mailed Jun. 15, 2015", 20 pgs.

(56) References Cited

OTHER PUBLICATIONS

"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/833,567, Non Final Office Action mailed Oct. 23, 2015", 10 pgs.
"U.S. Appl. No. 13/833,567, Response filed Jun. 25, 2015 to Restriction Requirement mailed Apr. 3, 2015", 10 pgs.
"U.S. Appl. No. 13/833,567, Restriction Requirement mailed Apr. 3, 2015"6 pgs.
"U.S. Appl. No. 13/838,755, Non Final Office Action mailed Sep. 17, 2015", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 14/071,295, Supplemental Notice of Allowability mailed Jan. 26, 2015", 2 pgs.
"U.S. Appl. No. 14/324,688, Non Final Office Action mailed Jan. 8, 2016", 18 pgs.
"U.S. Appl. No. 14/456,286, Non Final Office Action mailed Dec. 30, 2015", 16 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/589,101, Final Office Action mailed Oct. 2, 2015", 10 pgs.
"U.S. Appl. No. 14/589,101, Non Final Office Action mailed Feb. 12, 2015", 10 pgs.
"U.S. Appl. No. 14/589,101, Response filed Jun. 12, 2015 to Non Final Office Action mailed Feb. 12, 2015", 11 pgs.
"U.S. Appl. No. 14/589,101, Response filed Dec. 29, 2015 to Final Office Action mailed Oct. 2, 2015", 15 pgs.
"U.S. Appl. No. 14/794,309, Preliminary Amendment filed Sep. 22, 2015", 6 pgs.
"U.S. Appl. No. 14/876,167, Preliminary Amendment filed Oct. 27, 2015", 8 pgs.
"U.S. Appl. No. 14/936,831, Preliminary Amendment filed Nov. 11, 2015", 6 pgs.
"U.S. Appl. No. 14/956,724, Preliminary Amendment filed Dec. 7, 2015", 8 pgs.
"U.S. Appl. No. 14/983,108, Preliminary Amendment filed Dec. 30, 2015", 7 pgs.
"U.S. Appl. No. 14/983,747, Preliminary Amendment filed Jan. 4, 2016", 5 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Office Action mailed Nov. 10, 2015", 6 pgs.
"European Application Serial No. 11707316.3, Response filed Jun. 29, 2015 to Examination Notification Art. 94(3) mailed Dec. 17, 2014", 25 pgs.
"European Application Serial No. 12791902.5, Examination Notification Art. 94(3) mailed Aug. 14, 2015", 4 pgs.
"European Application Serial No. 12806211.4, Examination Notification Art. 94(3) mailed Aug. 13, 2015", 5 pgs.
"European Application Serial No. 13818131.8, Office Action mailed Jul. 28, 2015", 2 pgs.
"European Application Serial No. 14716173.1, Office Action mailed Nov. 5, 2015", 2 pgs.
"International Application Serial No. PCT/US2013/075989, International Preliminary Report on Patentability mailed Jul. 2, 2015", 10 pgs.
"International Application Serial No. PCT/US2014/026413, International Preliminary Report on Patentability mailed Sep. 24, 2015", 10 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.

\* cited by examiner

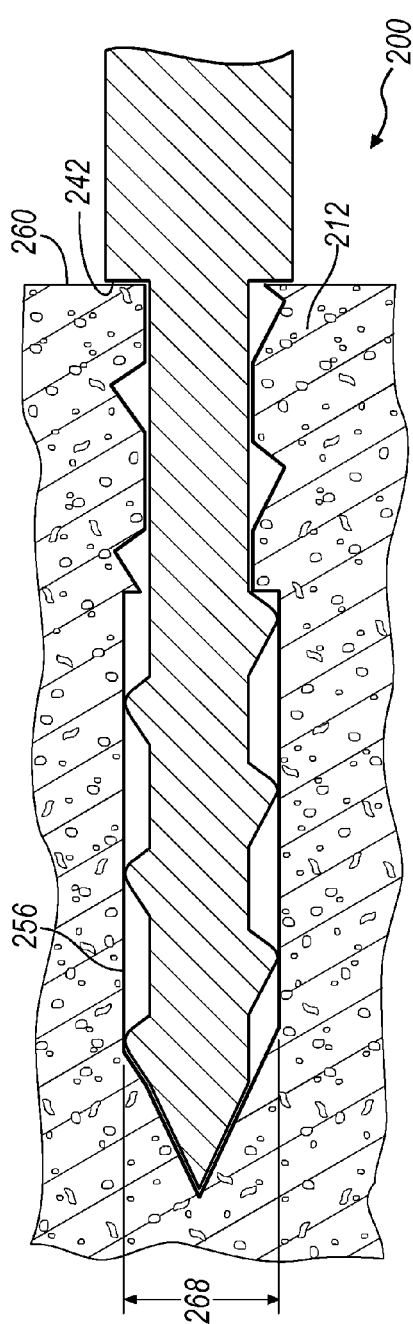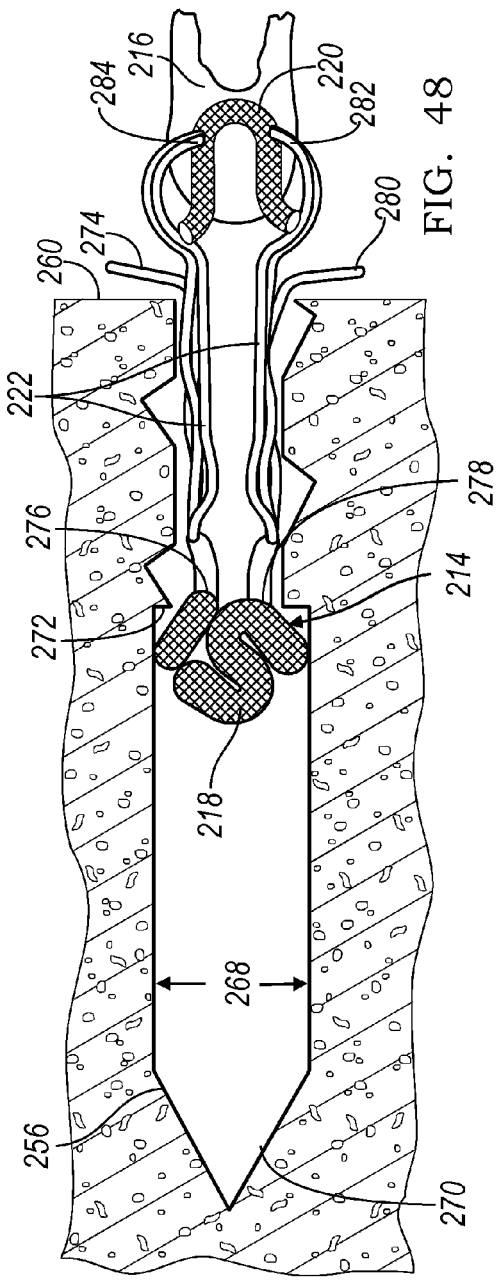

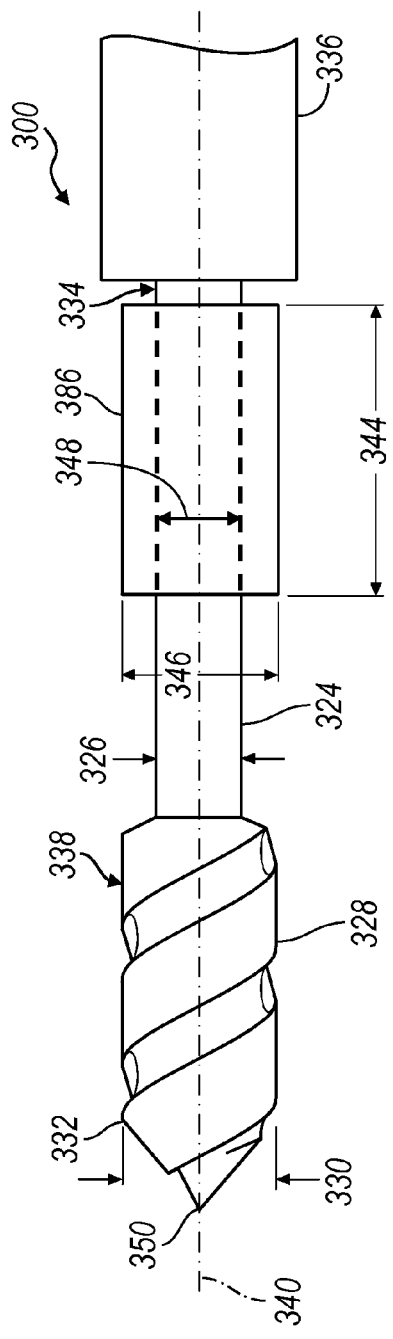
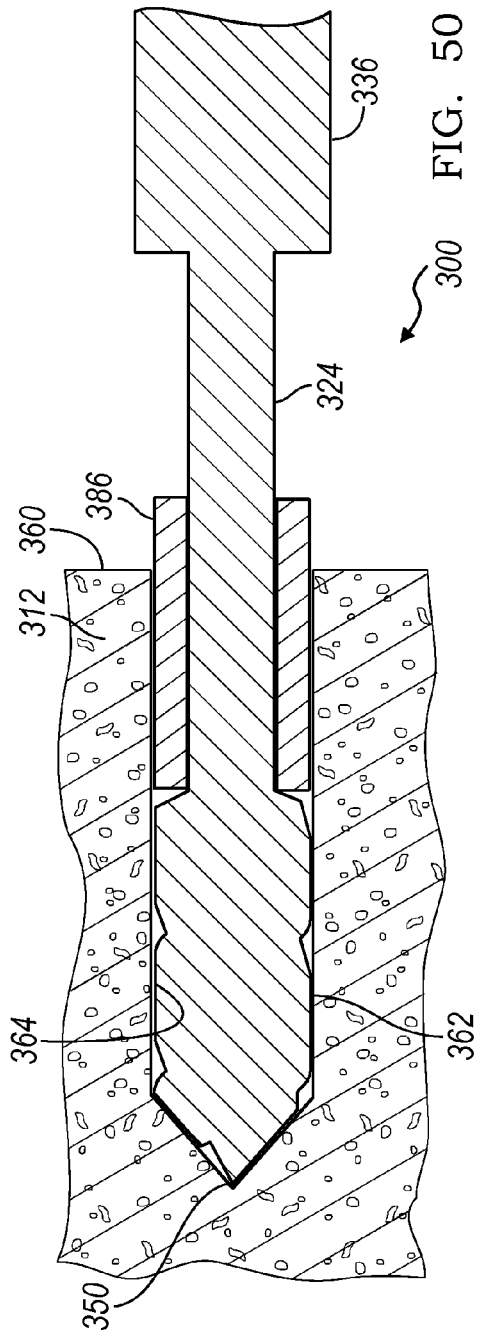

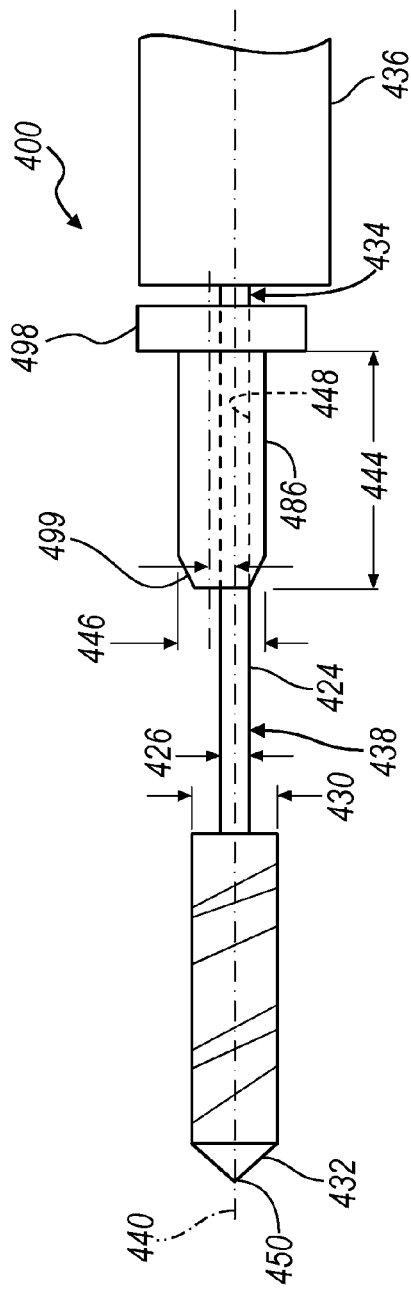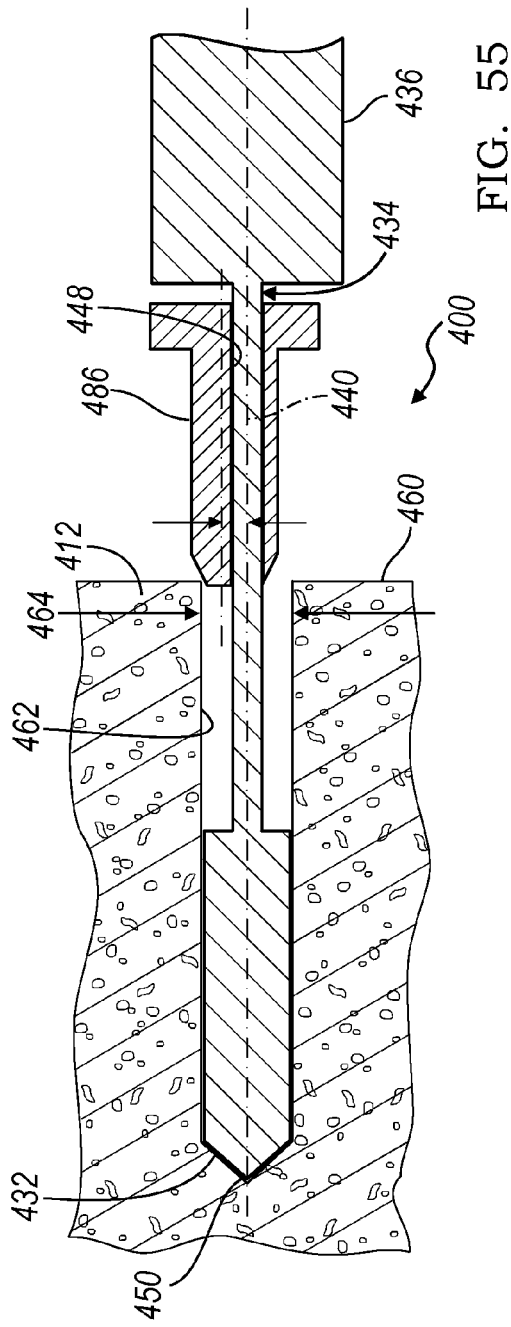

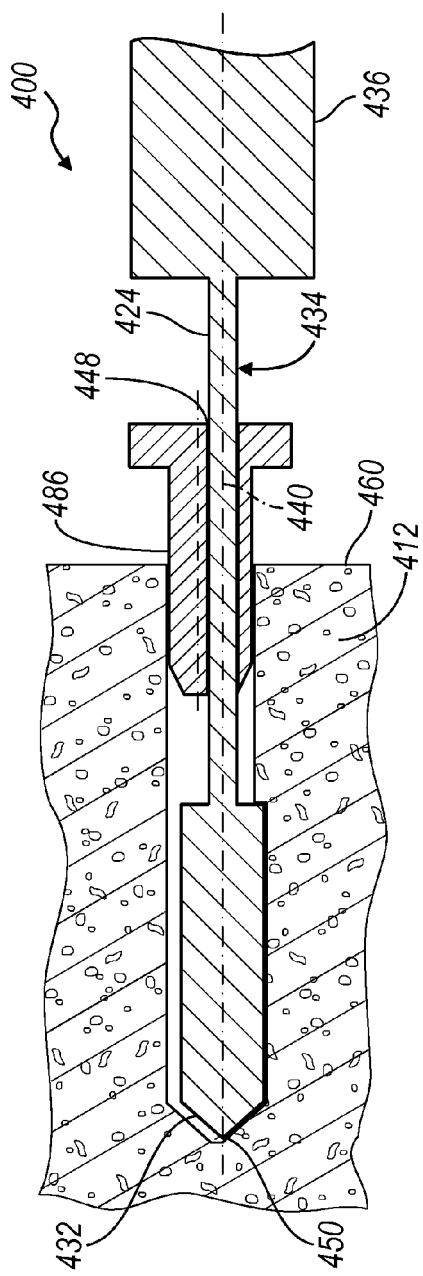
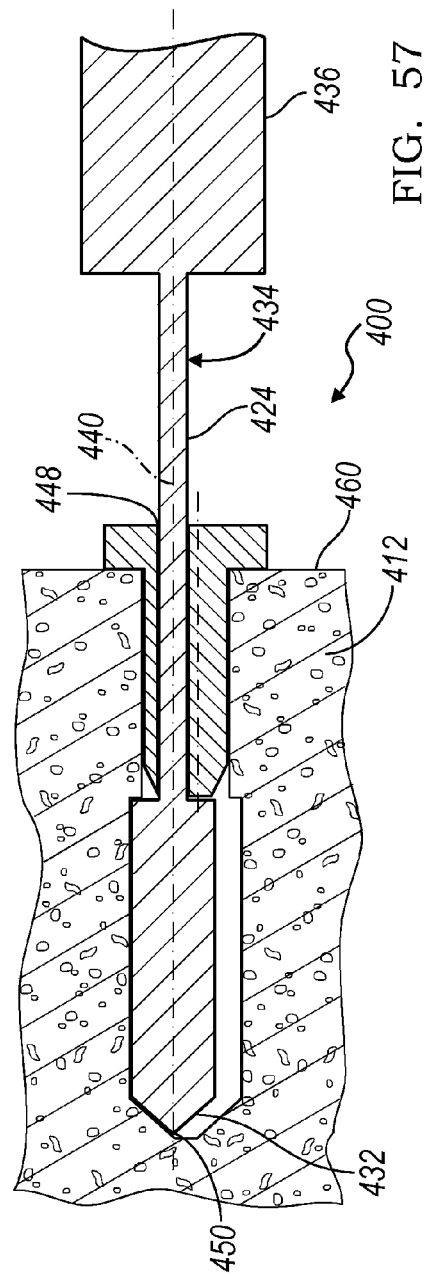

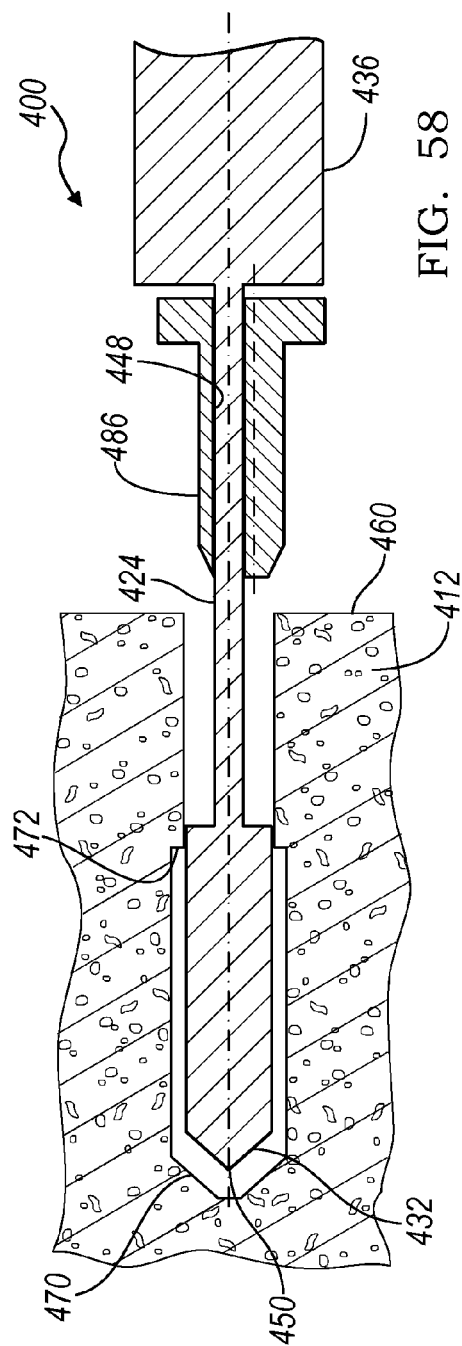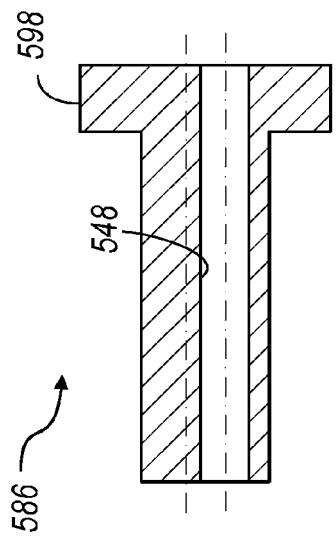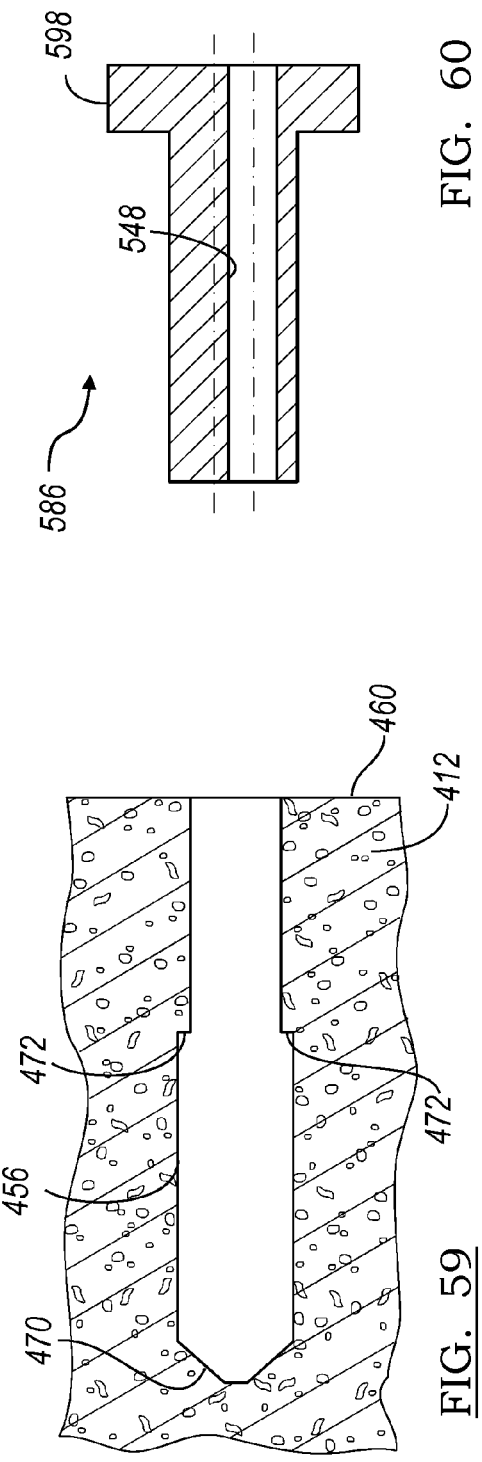

METHOD AND APPARATUS FOR COUPLING SOFT TISSUE TO A BONE

CROSS-REFERENCE TO RELATED APPLICATIONS

This application is a is a continuation-in-part application of U.S. patent application Ser. No. 12/474,802, filed on May 29, 2009, now U.S. Pat. No. 8,088,130 which is a continuation-in-part of (1.) U.S. patent application Ser. No. 11/541,506 filed on Sep. 29, 2006, now U.S. Pat. No. 7,601,165 issued on Oct. 13, 2009; (2.) U.S. patent application Ser. No. 11/541,505 filed on Sep. 29, 2006, now U.S. Pat. No. 7,658,751 issued on Feb. 9, 2010; (3.) U.S. patent application Ser. No. 12/014,399 filed on Jan. 15, 2008, now U.S. Pat. No. 7,909,851 issued on Mar. 22, 2011; (4.) U.S. patent application Ser. No. 12/014,340 filed on Jan. 15, 2008, now U.S. Pat. No. 7,905,904 issued on Mar. 15, 2011; (5.) U.S. patent application Ser. No. 11/935,681 filed on Nov. 6, 2007, now U.S. Pat. No. 7,905,903 issued on Mar. 15, 2011; (6.) U.S. patent application Ser. No. 11/869,440 filed on Oct. 9, 2007, now U.S. Pat. No. 7,857,830 issued on Dec. 28, 2010; (7.) U.S. patent application Ser. No. 11/784,821 filed on Apr. 10, 2007; (8.) U.S. patent application Ser. No. 11/347,661 filed on Feb. 3, 2006, now U.S. Pat. No. 7,749,250 issued on Jul. 6, 2010; and (9.) U.S. patent application Ser. No. 11/347,662 filed on Feb. 3, 2006, now abandoned.

This application is also a continuation-in-part of (1.) U.S. patent application Ser. No. 12/196,405 filed on Aug. 22, 2008 now U.S. Pat. No. 8,128,658; (2.) U.S. patent application Ser. No. 12/196,407, filed on Aug. 22, 2008 now U.S. Pat. No. 8,137,382; (3.) U.S. patent application Ser. No. 12/196,410, filed on Aug. 22, 2008 now U.S. Pat. No. 8,118,836; and (4.) U.S. patent application Ser. No. 13/071,563, filed on Mar. 25, 2011. The disclosures of the above applications are incorporated herein by reference.

FIELD

The present disclosure relates to method of coupling soft tissue and, more particularly, to a method of coupling soft tissue to a bone.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for attaching a fixation device to a bone is disclosed. The method includes bringing a bone cutting tool that extends along a longitudinal axis into engagement with an outer surface of the bone. The bone cutting tool is then rotated about the longitudinal axis while driving the bone cutting tool from the outer surface of the bone to a predetermined depth in the bone to form a bore. The bone cutting tool is continuously rotated at the predetermined depth to establish an enlarged bone pocket at a distal end of the bore. The bone pocket defines a shoulder extending around a circumference between the bone pocket and the bore. The bone cutting tool is next removed from the bone pocket and the bore and the fixation device is inserted into the bone pocket through the bore. The fixation device is now positioned against the shoulder of the bone pocket.

A method of attaching a fixation device to a bone is also disclosed. A bone cutting tool having a helical flute is brought into engagement with an outer surface of the bone. The bone cutting tool is rotated about a longitudinal axis to form a first bore having a helical flute groove extending from the outer surface of the bone to a depth within the bone. The bone cutting tool is continuously rotated at the depth to establish a second bore having a shoulder and a continuous sidewall. The shoulder extends around a circumference between the second bore and the first bore. The bone cutting tool is aligned with the first bore. The bone cutting tool is drawn out of the second and first bores. The fixation device is inserted into the second bore through the first bore. The fixation device is then positioned against the shoulder of the second bore.

In another embodiment, a method of attaching a fixation device to a bone is disclosed. A bone cutting tool is rotated through a cortical bone about a longitudinal axis of the tool to a predetermined depth in the cancellous bone to form a bore. The bone cutting tool includes a body portion, a first member, and a second member. The body portion extends from a proximal end to a distal end along the longitudinal axis. The first member extends radially outwardly from the distal end of the body portion. The first member has a first diameter defined by at least one transverse cutting flute. The second member extends radially outwardly from the body portion proximal the first member and has a second diameter greater than the first diameter. The bone cutting tool is continuously rotated at the predetermined depth to establish an enlarged bone pocket at a distal end of the bore. The bone pocket defines a shoulder extending around a circumference between the bone pocket and the bore.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 47 is a cross-sectional view of the bone cutting device of FIG. 45 in a final operative position in association with the bone of the body;

FIG. 48 is a cross-sectional view of a bone socket established by the bone cutting device of FIG. 45 having a soft suture anchor inserted therewith;

FIG. 49 is a side view of an alternate bone cutting device constructed in accordance with the teachings of the present disclosure;

FIG. 50 is a cross-sectional view of the bone cutting device of FIG. 49 in an initial operative position in association with a bone of a body;

FIG. 54 is a side view of another alternate bone cutting device constructed in accordance with the teachings of the present disclosure;

FIG. 55 is a cross-sectional view of the bone cutting device of FIG. 54 in an initial operative position in association with a bone of a body;

FIG. 56 is a cross-sectional view of the bone cutting device of FIG. 54 incorporating a sleeve in a first intermediate operative position in association with the bone of the body;

FIG. 57 is a cross-sectional view of the bone cutting device of FIG. 54 incorporating the sleeve in a second intermediate operative position in association with the bone of the body;

FIG. 58 is a cross-sectional view of the bone cutting device of FIG. 54 in a final operative position in association with the bone of the body;

FIG. 59 is a cross-sectional view of a bone socket established by the bone cutting device of FIG. 54 and the sleeve of FIG. 56; and FIG. 60 is a cross-sectional view of an alternate sleeve for use with the bone cutting device of FIG. 54.

Corresponding reference numerals indicate corresponding parts throughout the several views of the drawings.

DETAILED DESCRIPTION

Figure 1:
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
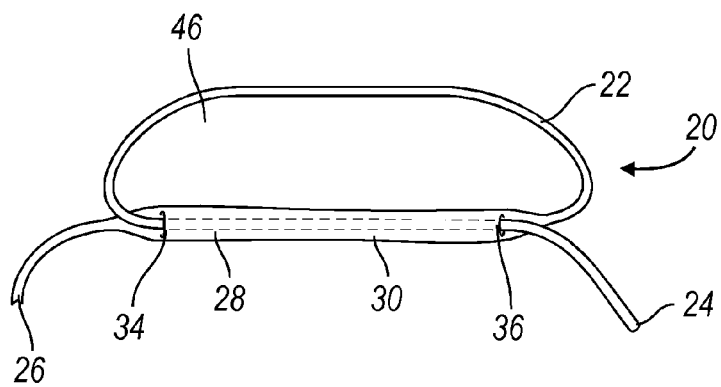
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
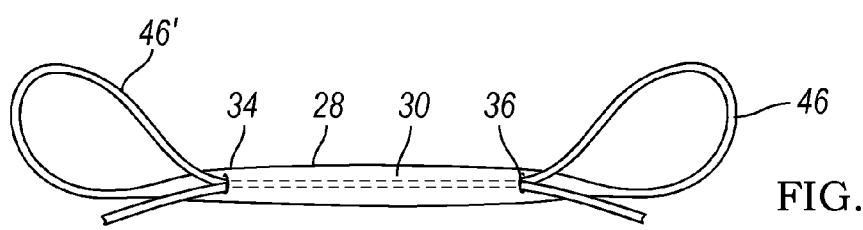
Figure 3:
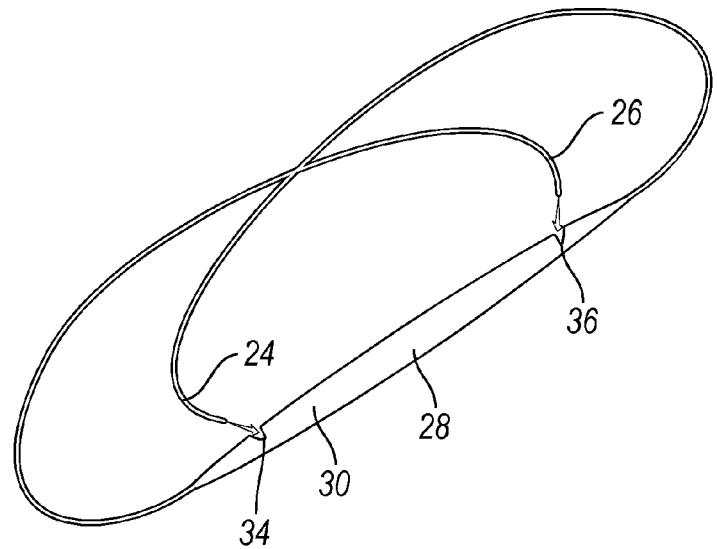
FIG. 3 represents the formation of the suture configuration shown in FIG. 2A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

Figure 4A:
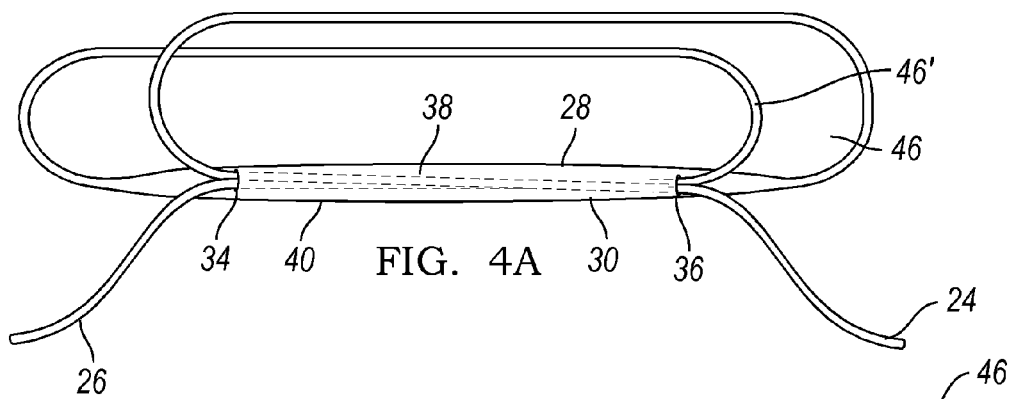
FIGS. 4A and 4B represent alternate suture configurations.
Figure 4B:
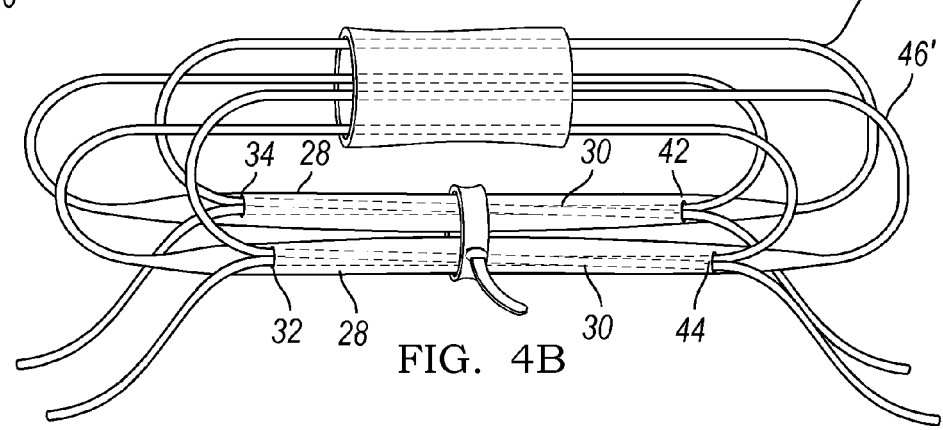

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
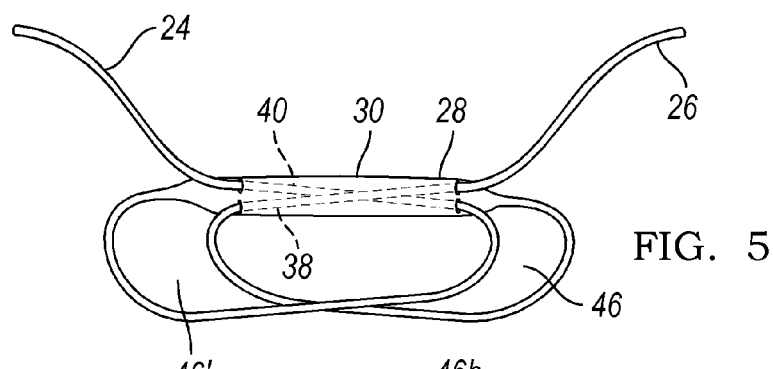
FIGS. 5-7 represent further alternate suture configurations.
Figure 6:
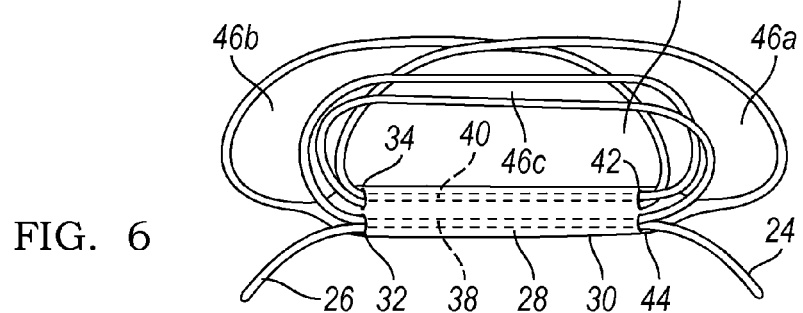
Figure 7:
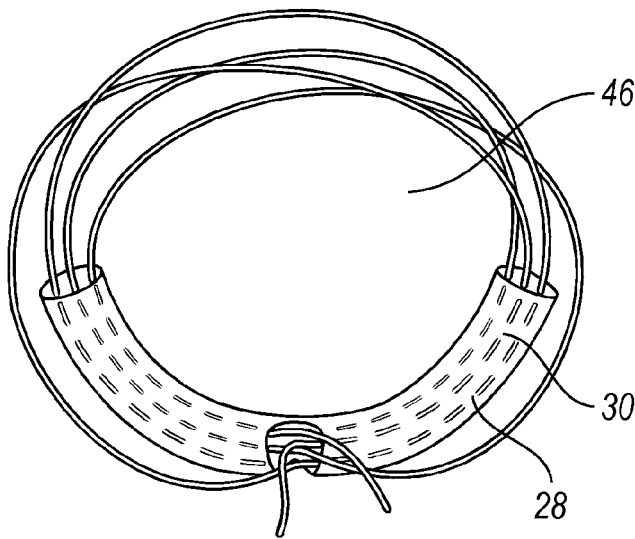
Figure 8:
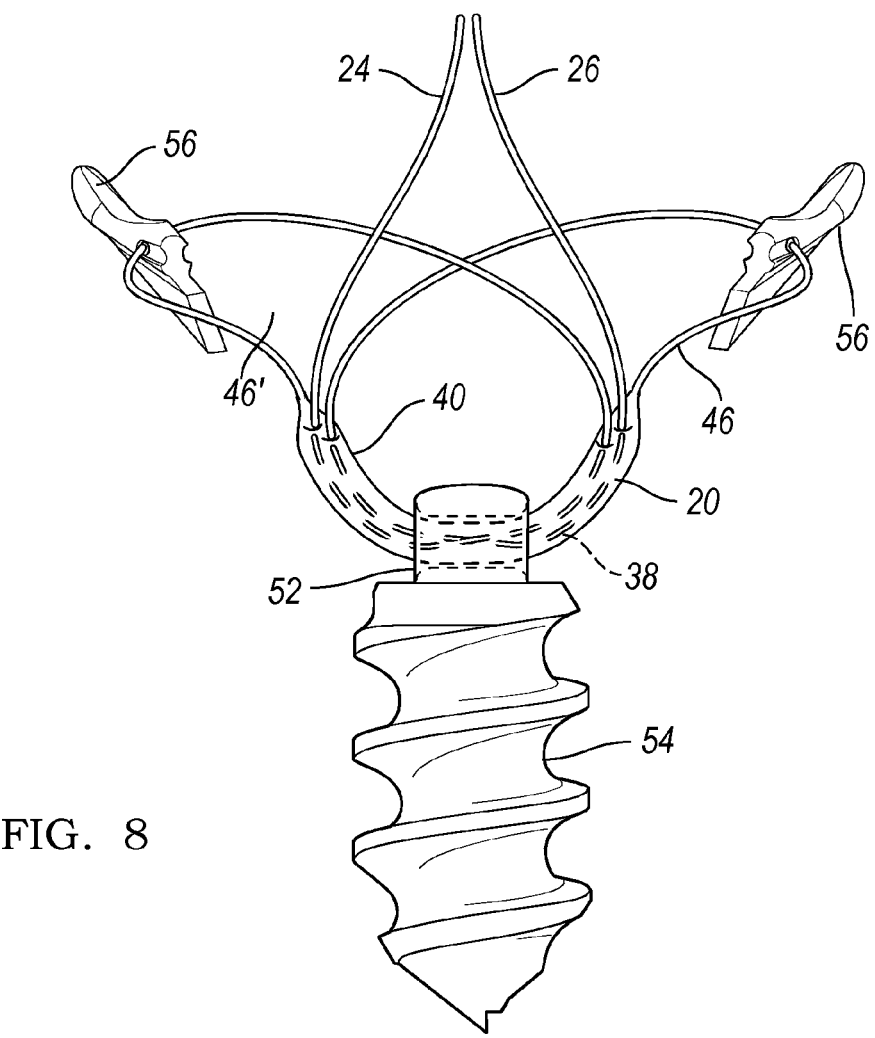
FIG. 8 represents the suture construction according to FIG. 5 coupled to a bone engaging fastener.
Figure 9:
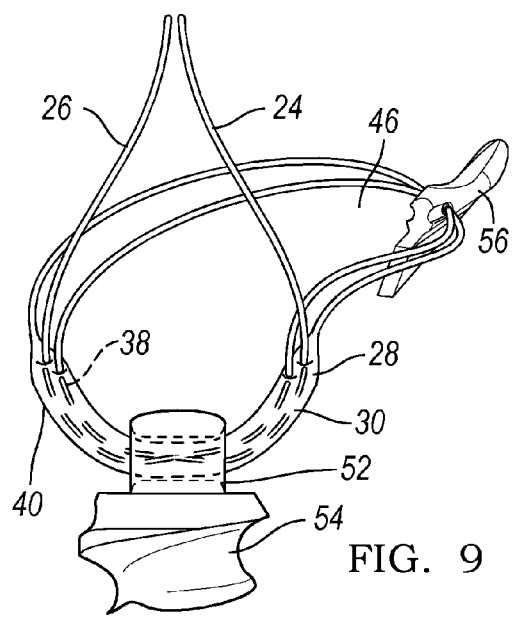
FIGS. 9-11 represent the coupling of the suture construction according to FIG. 5 to a bone screw.
Figure 10:
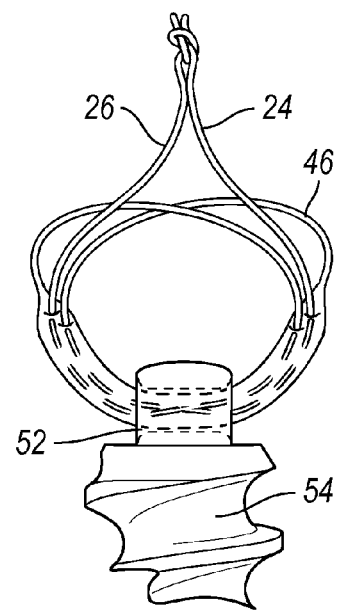

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
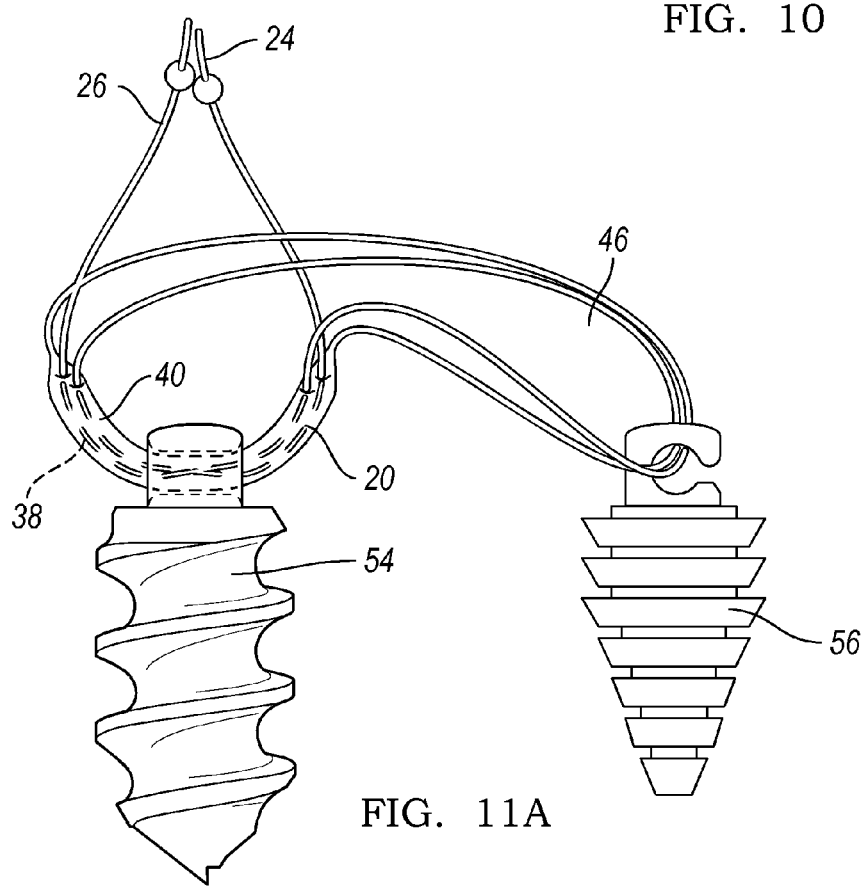
Figure 11B:
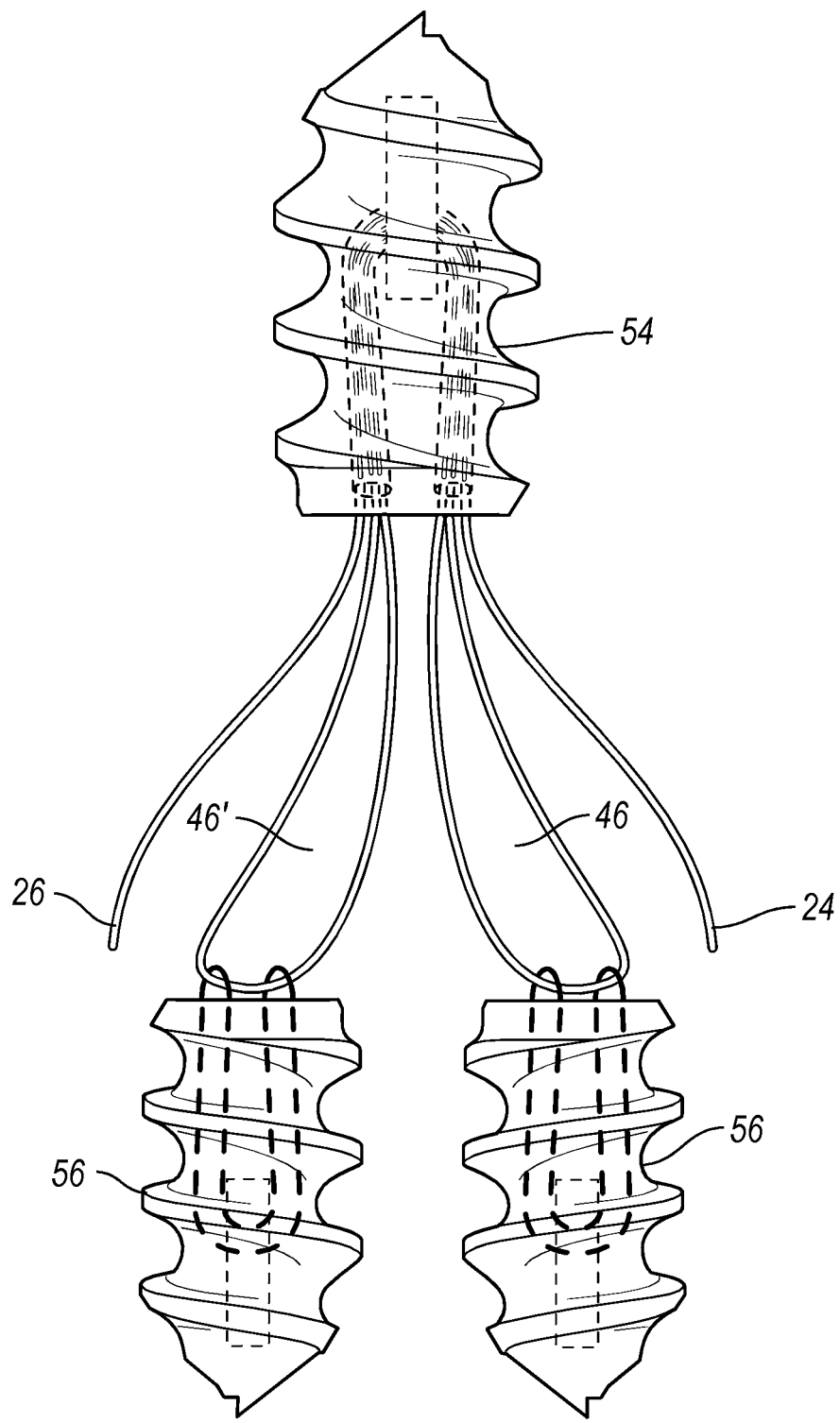

FIG. 11B represents the coupling of the suture construction according to FIG. 2B with a bone fastening member. Coupled to a pair of loops 46 and 46' are tissue fastening members 56. The application of tension to either the first or second end 24 or 26 will tighten the loops 46 or 46' separately.

Figure 12A:
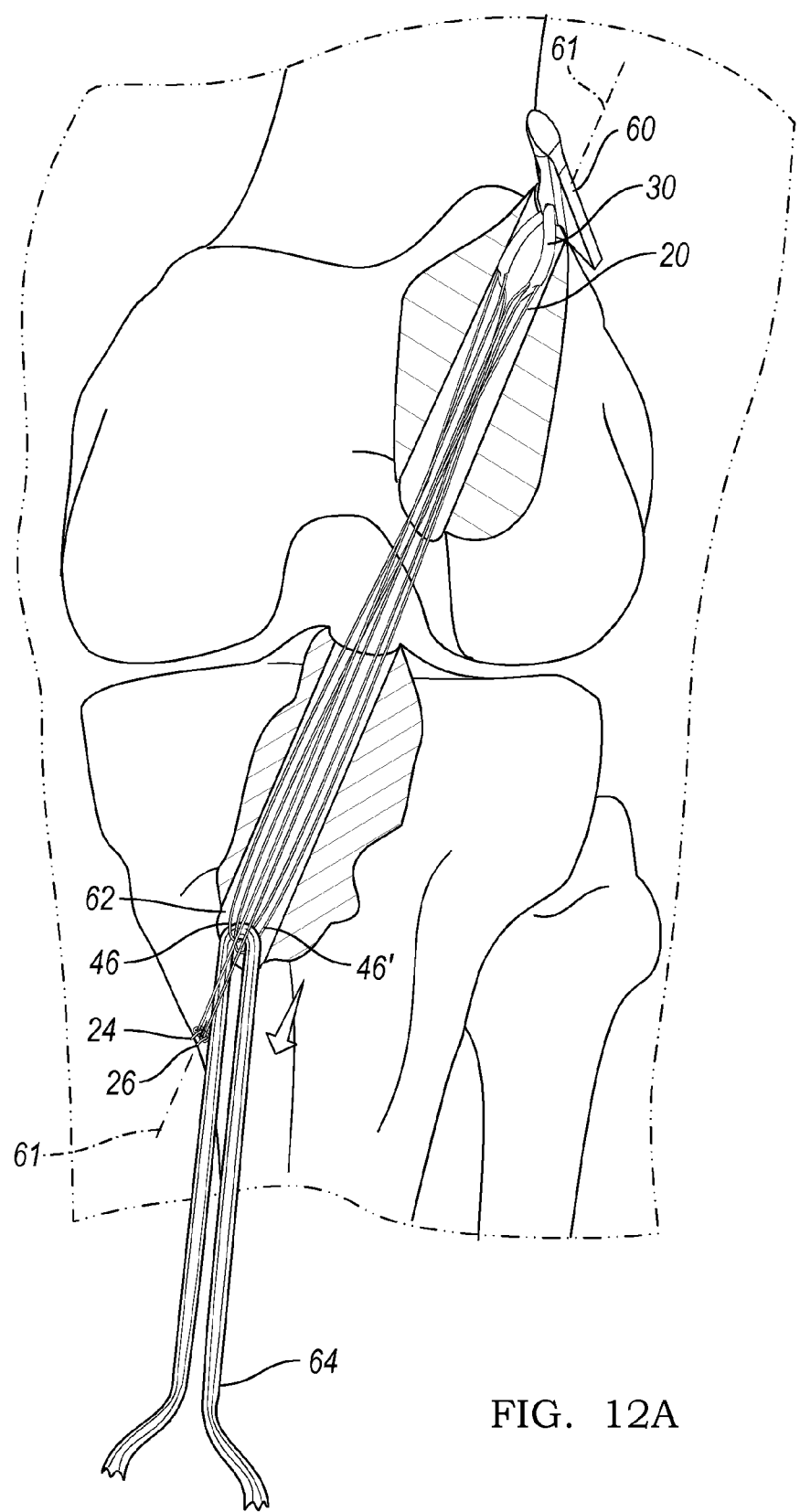
FIGS. 12A-12E represent the coupling of a soft tissue to an ACL replacement in a femoral/humeral reconstruction.
Figure 12B:
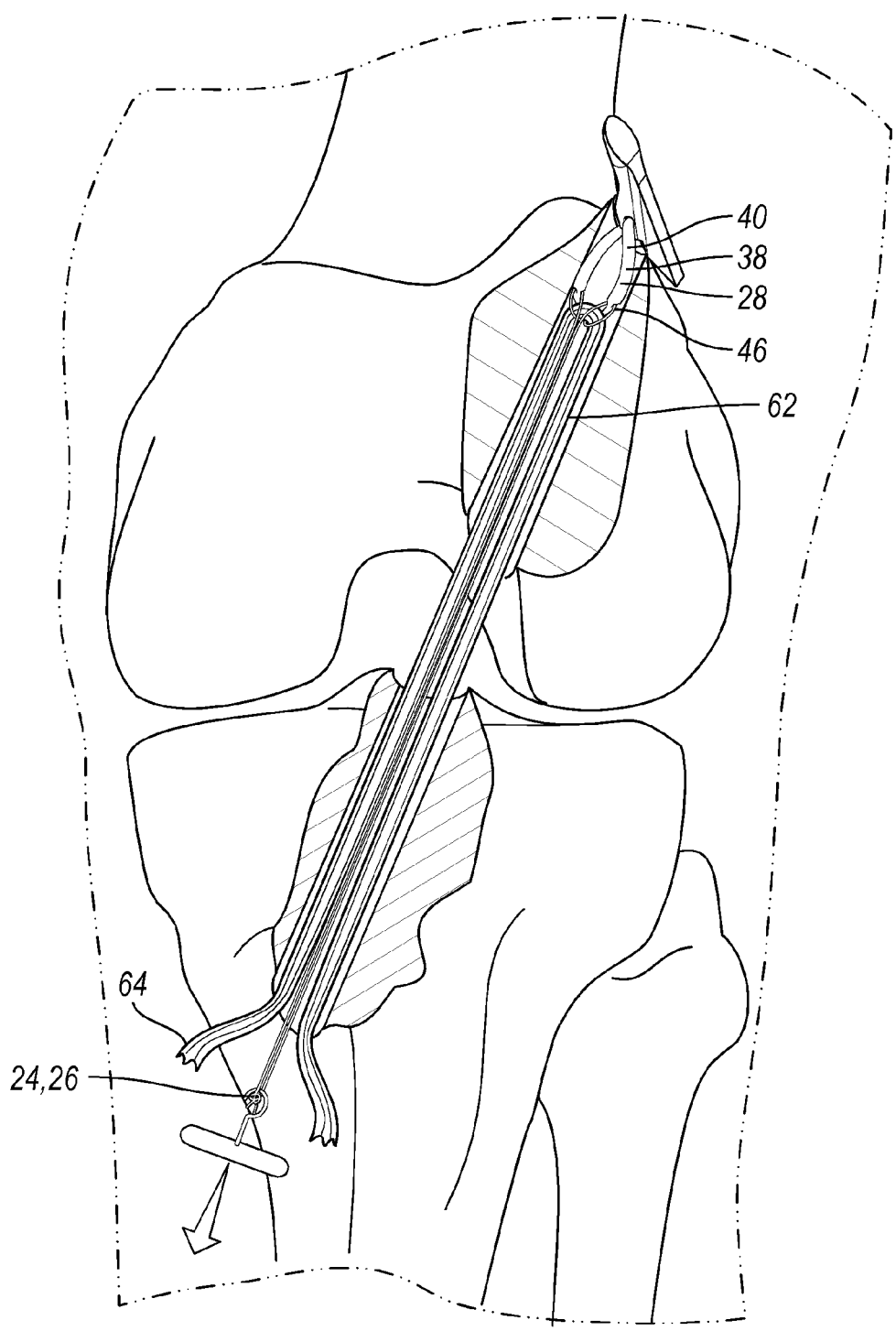

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member or fastener 60. The fixation member 60 can have a first profile which allows insertion of the fixation member 60 through the tunnel and a second profile which allows engagement with a positive locking surface upon rotation. The longitudinal passage portion 30 of the suture construction 20, fixation member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the fixation member 60, application of forces to the ends 24, 26 may reduce the seating force applied by the fixation member 60 onto the bone.

Figure 12C:
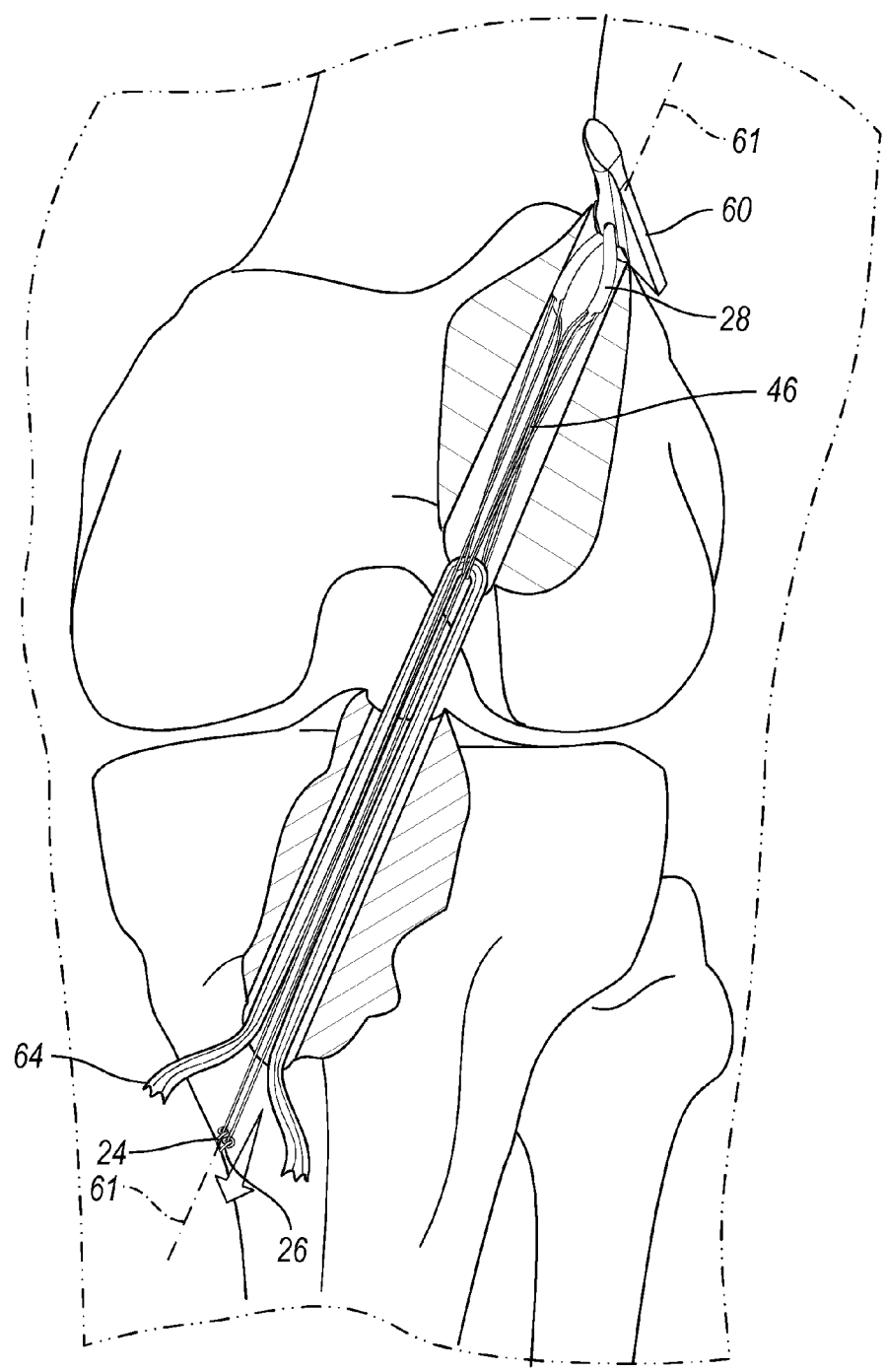
Figure 12D:
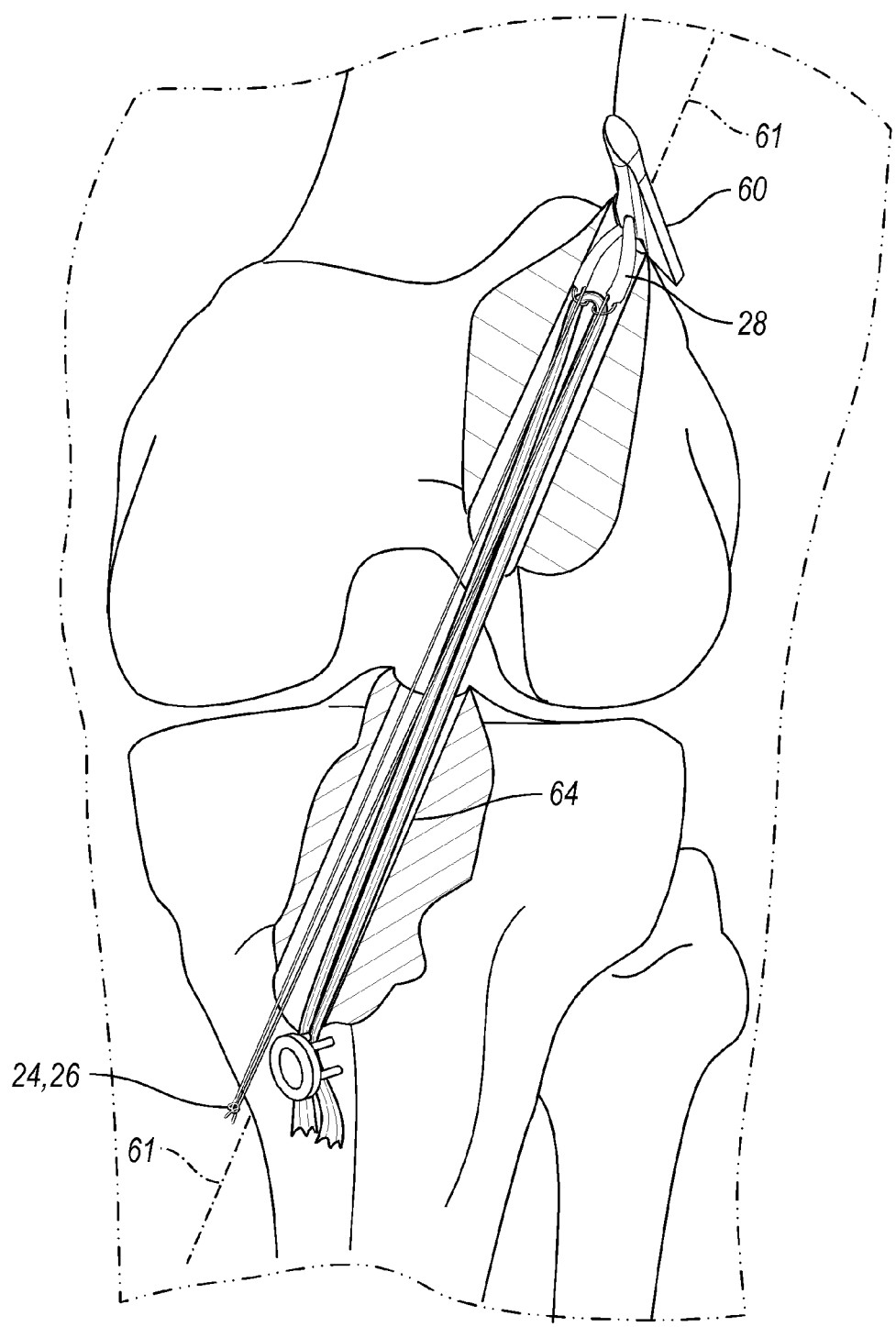

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
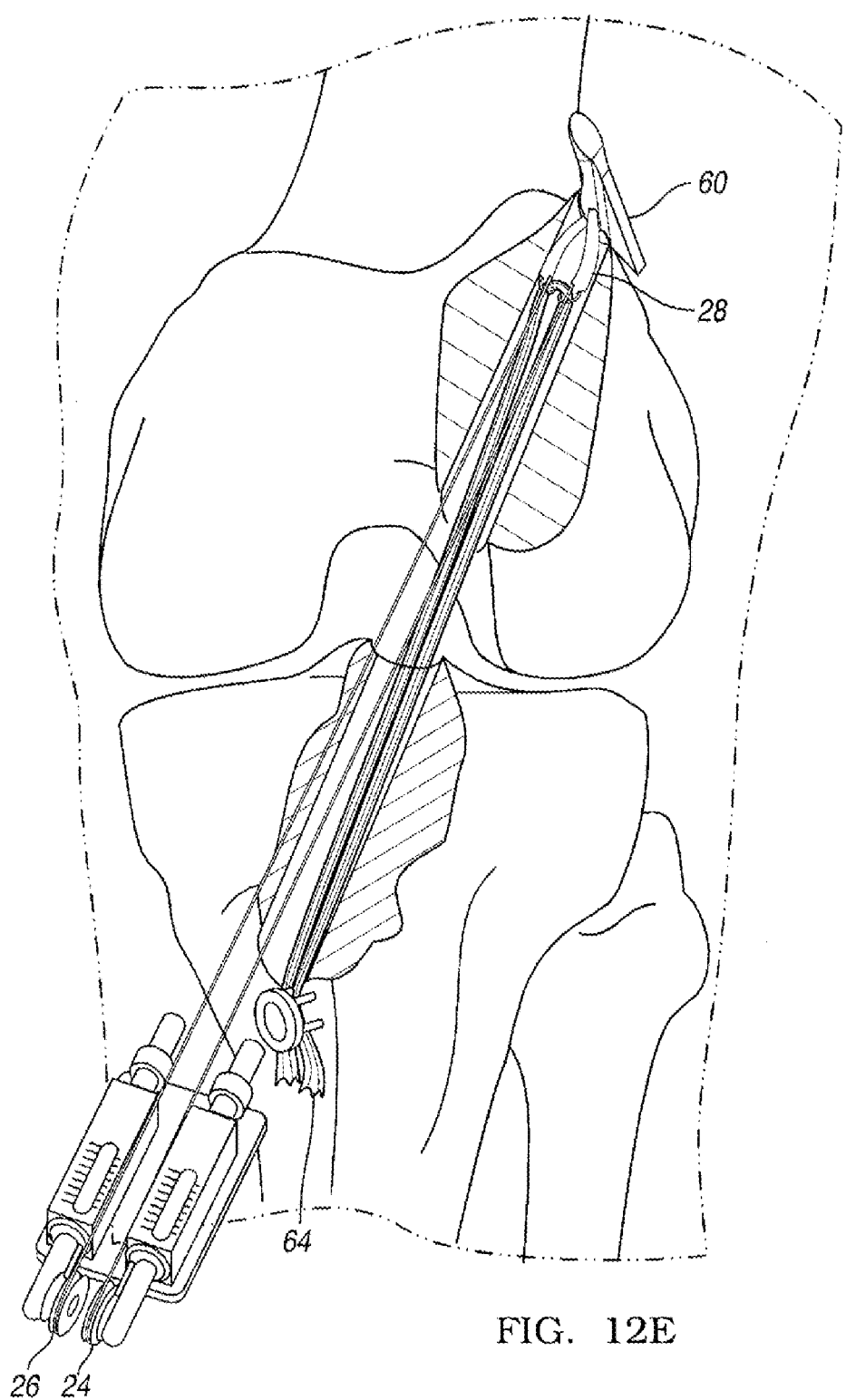
Figure 13A:
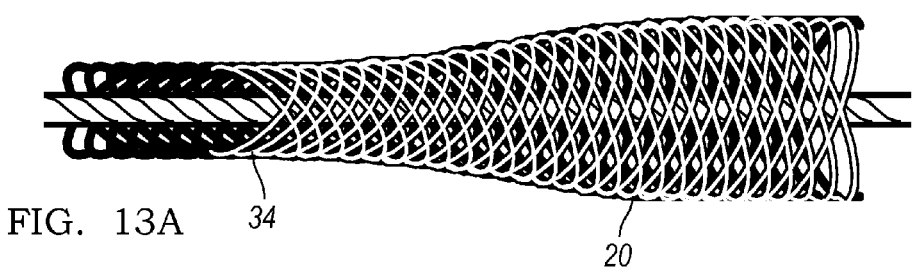
FIGS. 13A-13D represent a close-up view of the suture shown in FIGS. 1-11C.
Figure 13B:
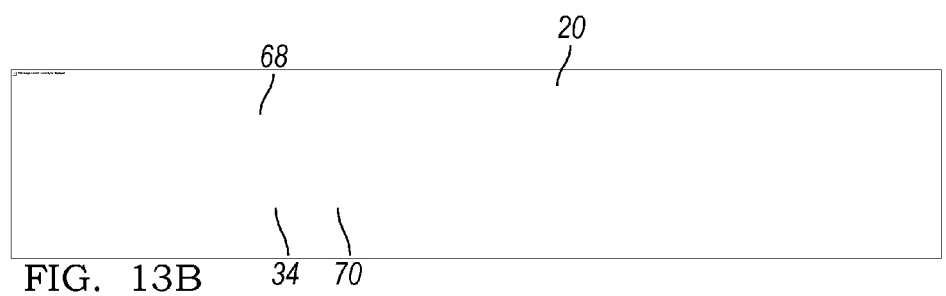
Figure 13C:
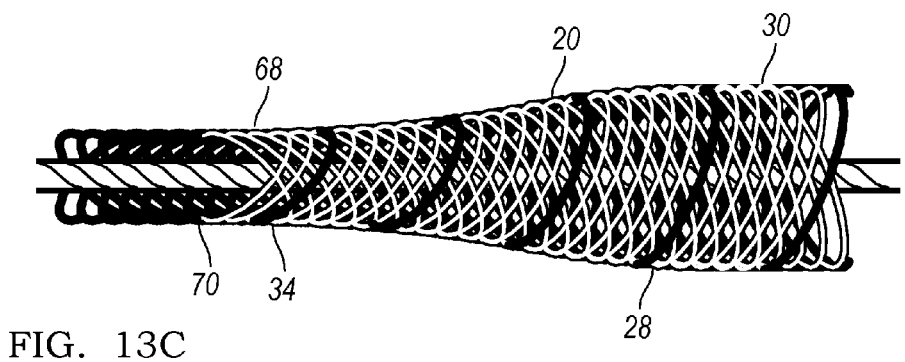
Figure 13D:
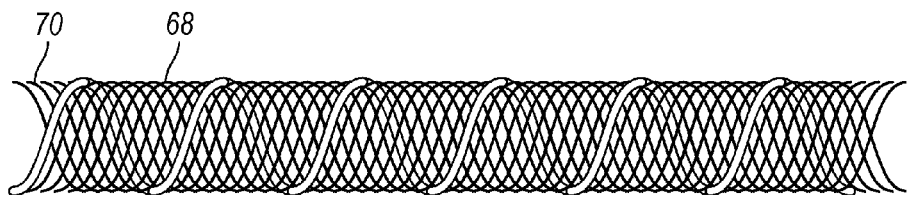

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter d1 which is larger than the diameter d2 of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14A:
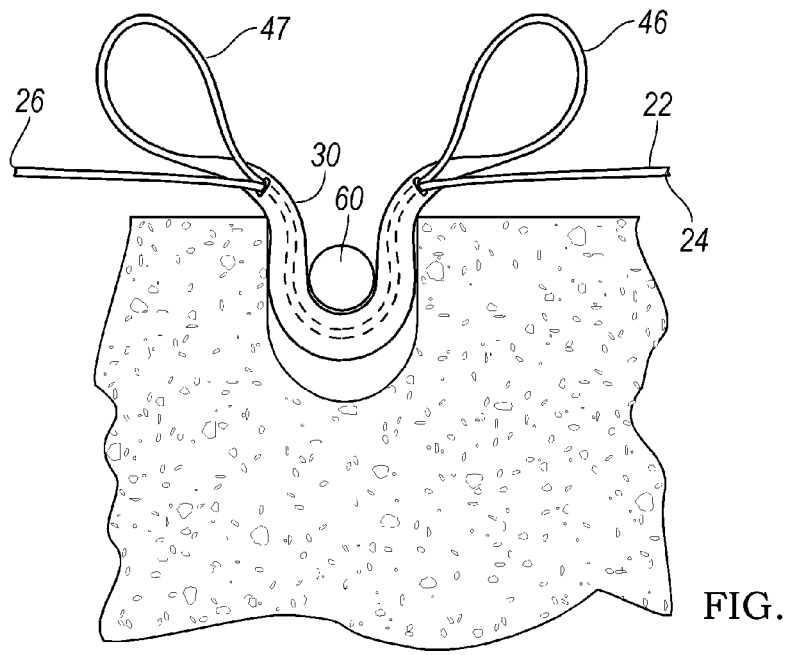
FIGS. 14A and 14B represent the coupling of the suture construction of FIG. 2A and FIG. 4 to bone.
Figure 14B:
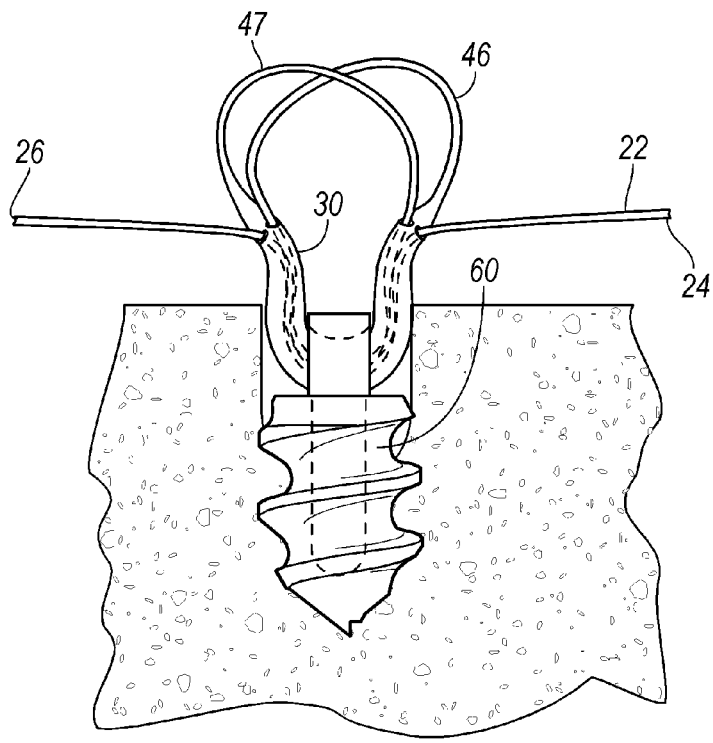

FIGS. 14A and 14B represent the coupling of suture construction 22 of FIG. 2A and FIG. 4 to a bone. The longitudinal passage 30 is coupled to a fixation member 60 which can be disposed within an aperture formed in the bone. The fixation member 60 can be, for example, a staple or a bone engaging screw. After coupling the suture construction 22 to the bone, loops 46 and 47 and ends 24 and 26 are readily accessible by the physician. The application of tension to the ends 24 and/or 26 causes the loops 46 and 47 to constrict. The loops 46 and 47 can be used to couple two or more portions of the anatomy. In this regard, the loops can be used to couple bone to bone or soft tissue to bone.

Figure 15A:
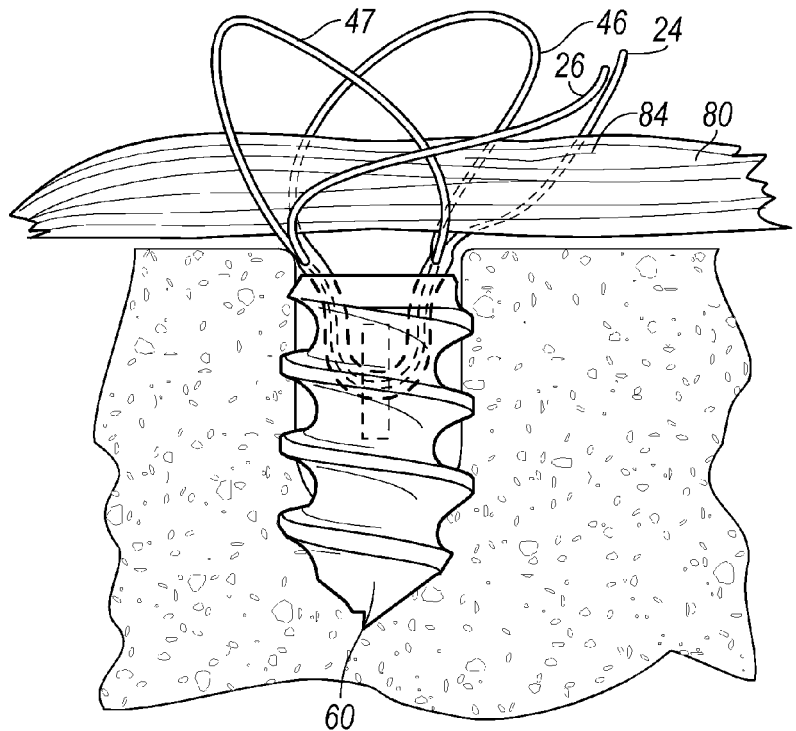
FIGS. 15A-15G represent the coupling of soft tissue to a bone according to the present teachings.
Figure 15B:
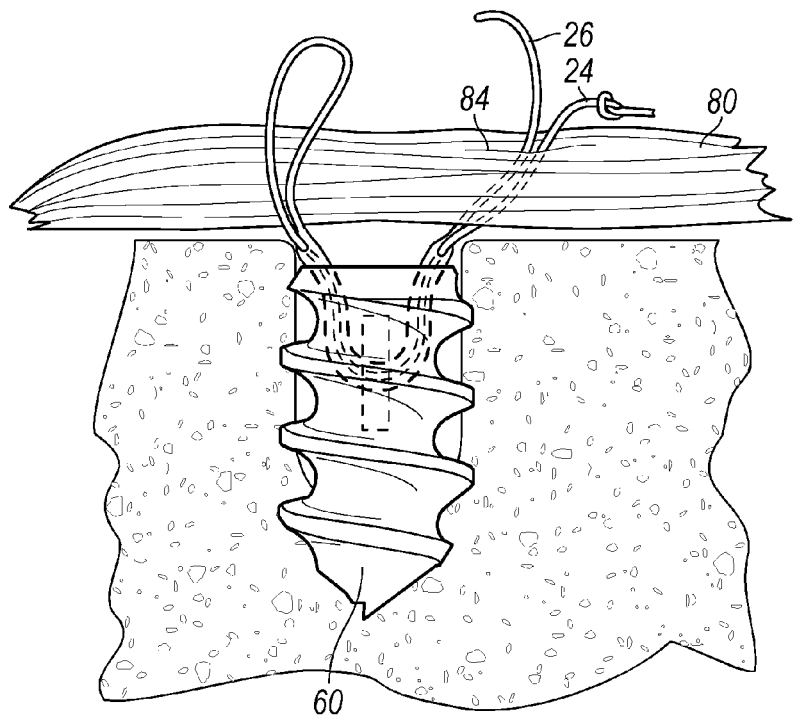

FIGS. 15A-15G represent the coupling of soft tissue 80 to bone. As shown in FIGS. 15A and 15B, the suture construction 22 is disposed about a portion of the soft tissue 80. Alternatively, an aperture or hole 84 can be formed in the soft tissue 80. A portion of the suture construction 22, for example, a loop 46 or loops 46, 47 or ends 24 and 26 can be threaded or pulled through the aperture 84. As seen in FIG. 15B, a single loop 46 of suture can be coupled to the fastener 60. This single loop 46 can be disposed over or around the soft tissue 80.

Figure 15C:
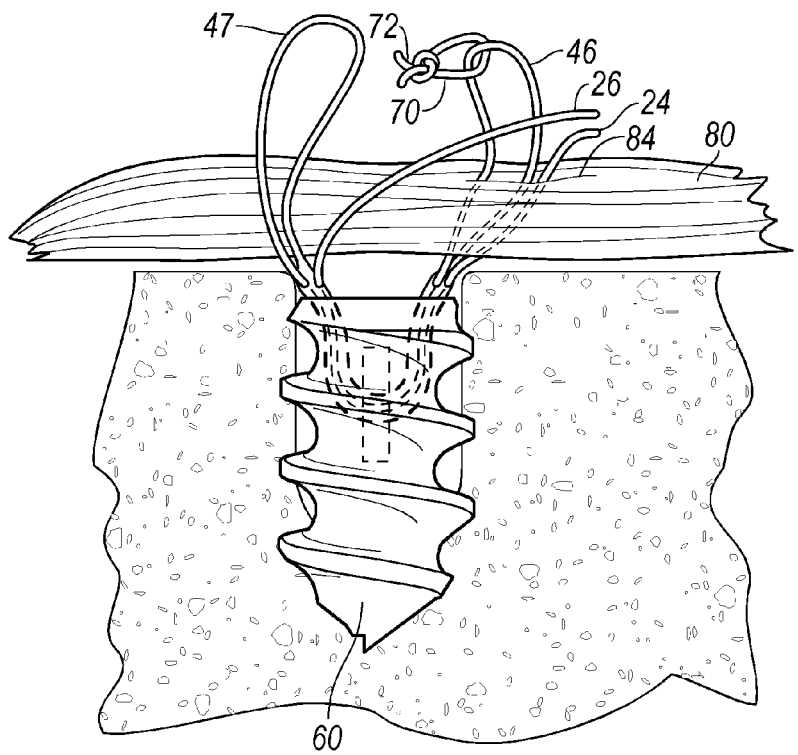

As shown in FIG. 15C, one loop 46 can have a fastening element 70 coupled thereto. This fastener element 70 can take the form of a loop of suture having a knot 72. This fastening element 70 along with the loop 46 and one or more strands 24 can be passed through the aperture 84 formed in the soft tissue 80.

Figure 15D:
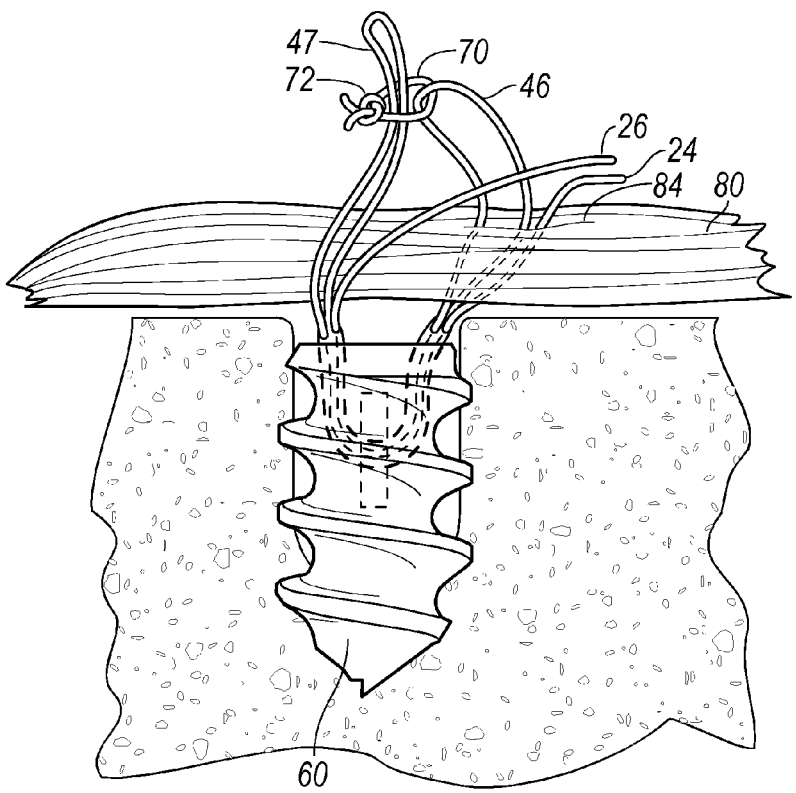

FIG. 15D shows the second loop 47 can be passed around the soft tissue and coupled to the fastening element 70. The first and second loops 46 and 47 are coupled together about the soft tissue 80, and optionally can be positioned about the knot 72.

Figure 15E:
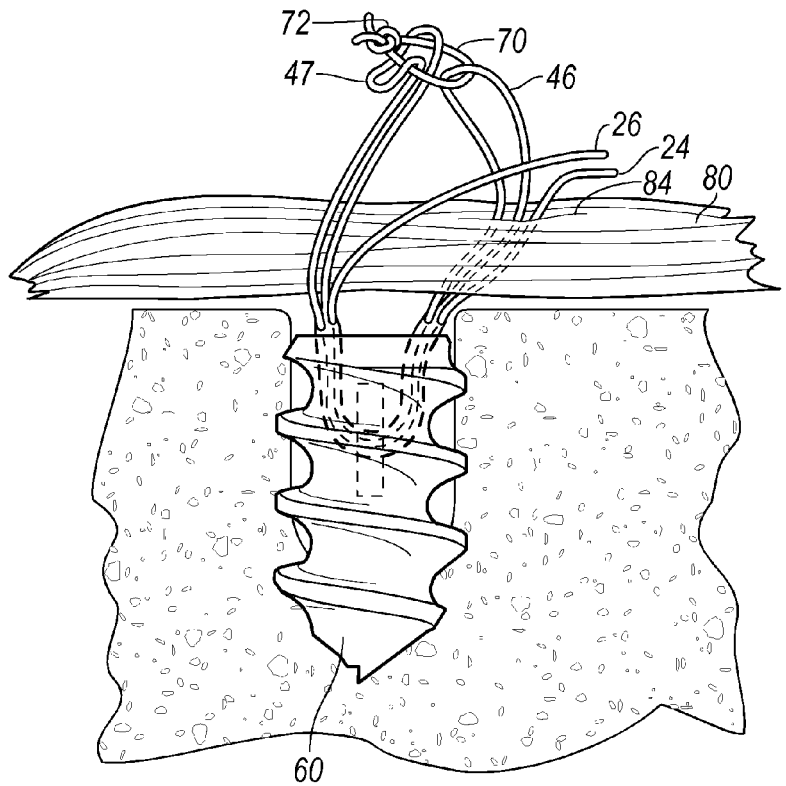
Figure 15F:
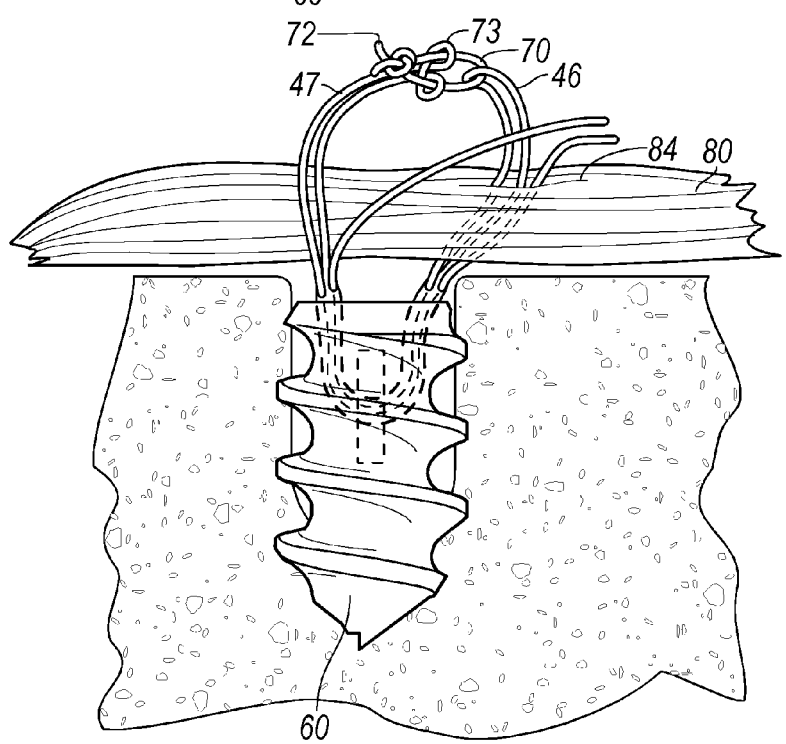
Figure 15G:
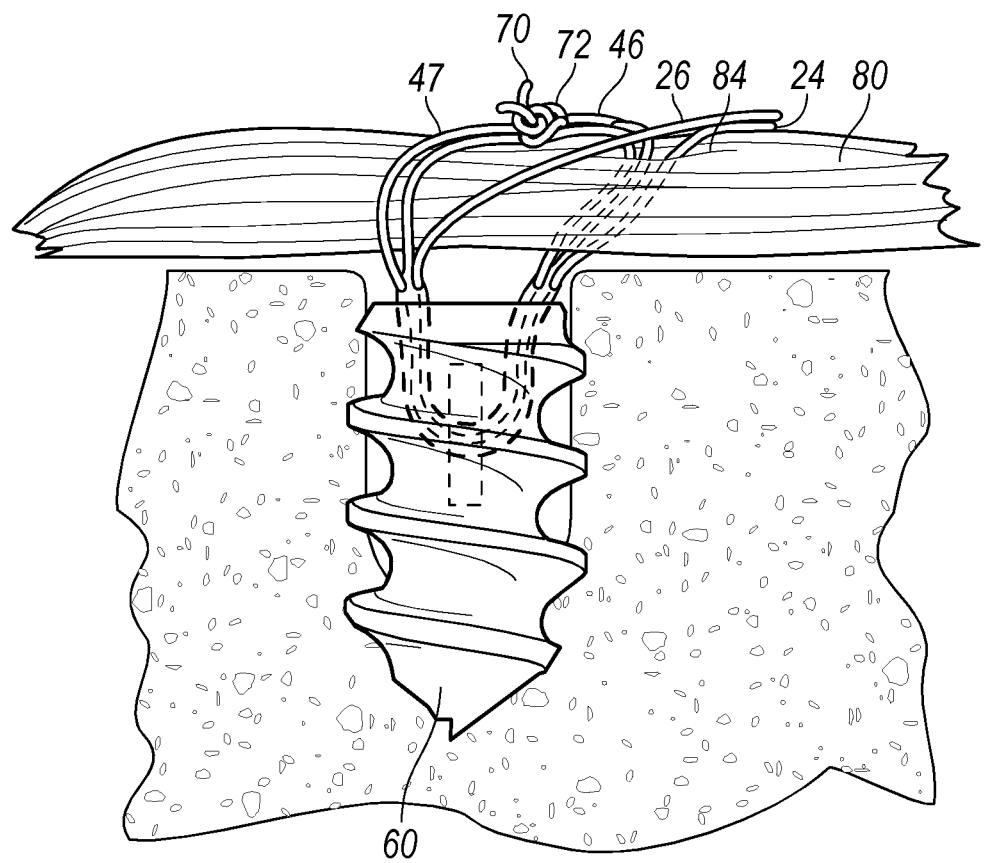

As shown in FIG. 15E, the first loop 46 and first end 24 can be passed through an aperture 84 of the soft tissue 80. Coupled to the first loop 46 is a fastener 70 in the form of a suture having a knot 72. The second loop 47 can be passed through the suture 70 and the knot 72 so as to form a pair of locking loops 73 (see FIG. 15F). FIG. 15G shows that tension can be applied to the first and second ends 24 and 26 of the suture 22 to constrict the suture 22 about the soft tissue 80. In this regard, the first and second loops 46 and 47 are tightened to constrict about and fix the soft tissue 80 to the bone.

Figure 16A:
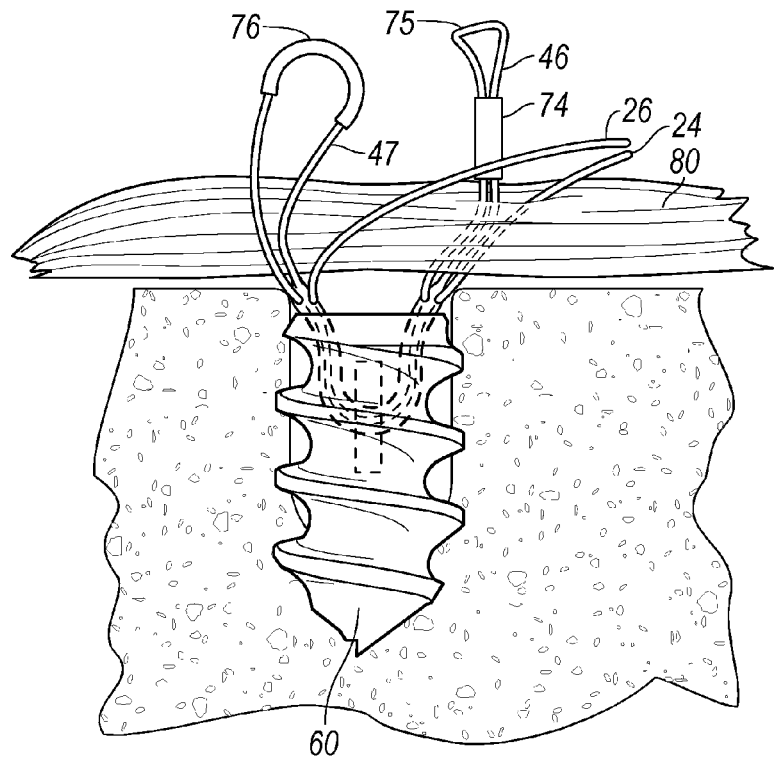
FIGS. 16A-16D represent the coupling of soft tissue to a bone using alternate teachings.

As seen in FIG. 16A, the construction of FIGS. 14A and 14B can be modified so as to place a pair of collapsible fabric tubes 74 and 76 about a portion of the suture 22. In this regard, collapsible tubes 74 and 76 can be coupled to the first and second suture loops 46 and 47. It is also envisioned several collapsible tubes can be coupled to a single loop 46 or the suture ends 26, 27.

Figure 16B:
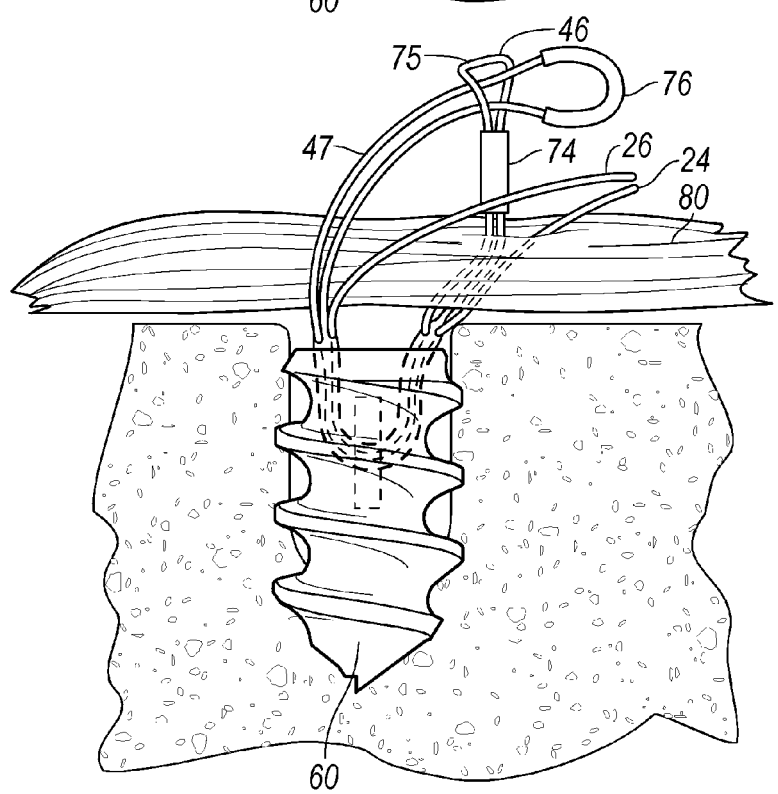
Figure 16C:
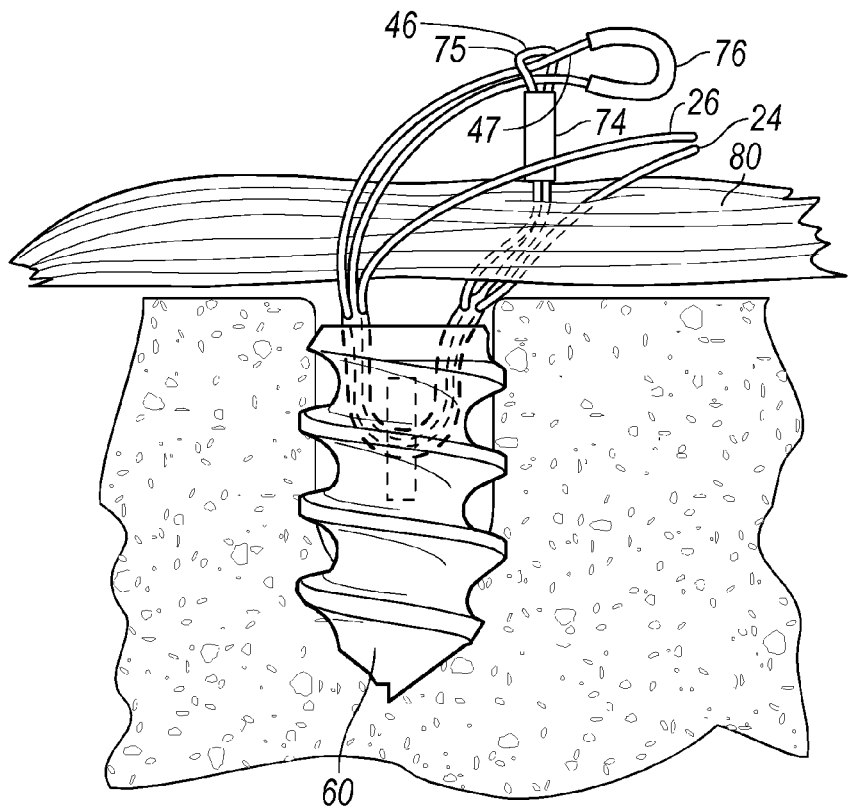
Figure 16D:
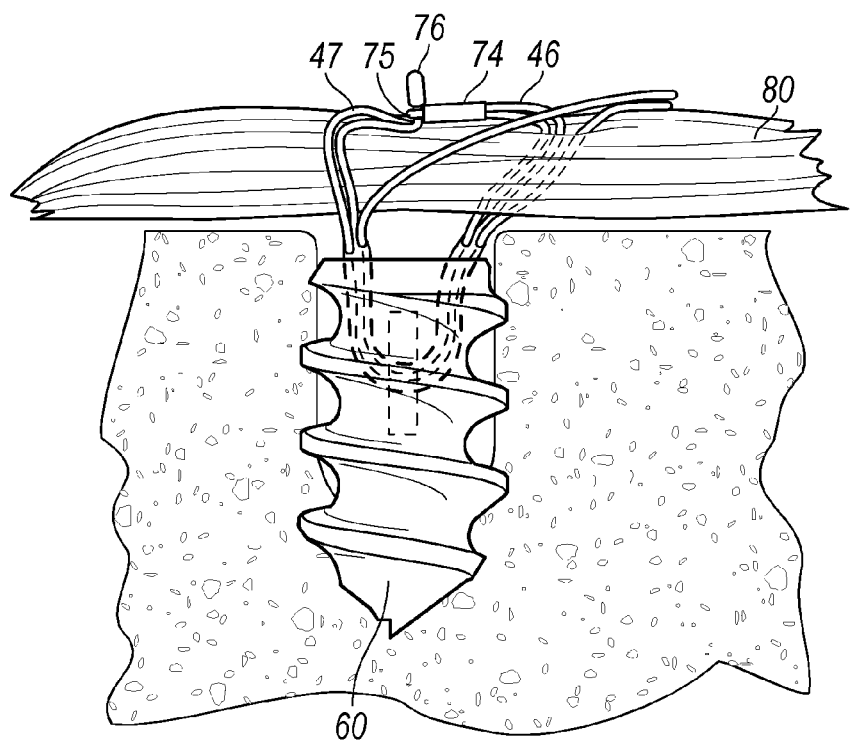

The collapsible tubes 74 and 76 can be either threaded onto (76) or disposed about a loop 75 formed in the suture loop 46. As seen in FIG. 16B, the first collapsible tube 76 can be fed through the loop 75. When tension is applied to the second end 26 of the sutures 47, the first loop 46 constricts about the second loop causing the collapse of the first collapsible tube 74. As shown in FIG. 16D, tension can be applied to the first suture end 24 causing the second loop 47 to constrict causing the collapse of the second collapsible tube 76 and the subsequent locking of the soft tissue 80 to the bone.

Figure 17A:
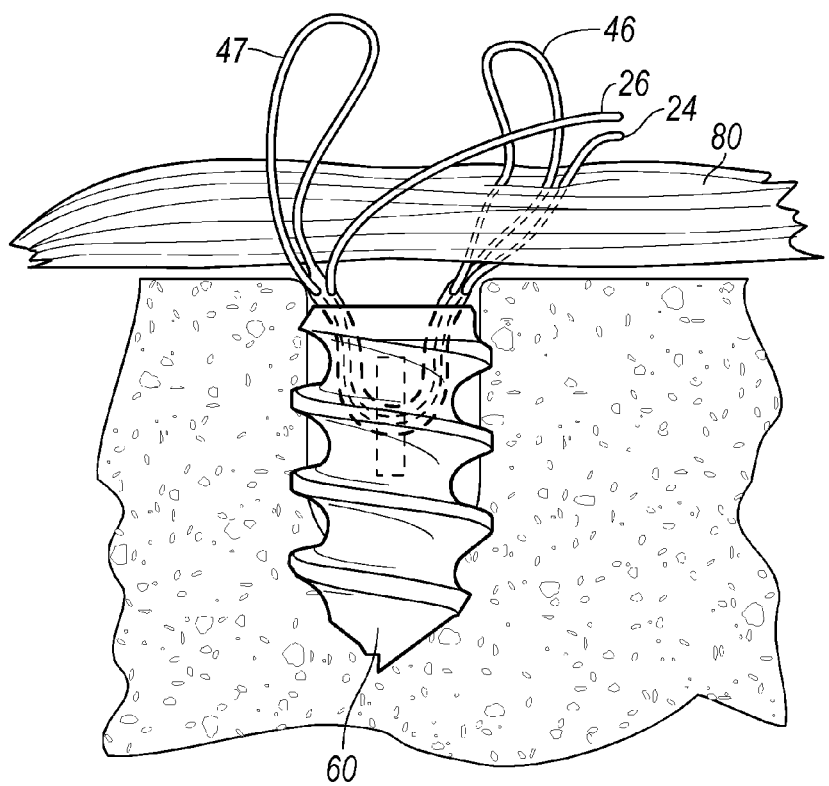
FIGS. 17A-17E represent the coupling of soft tissue to a bone using alternate teachings.
Figure 17B:
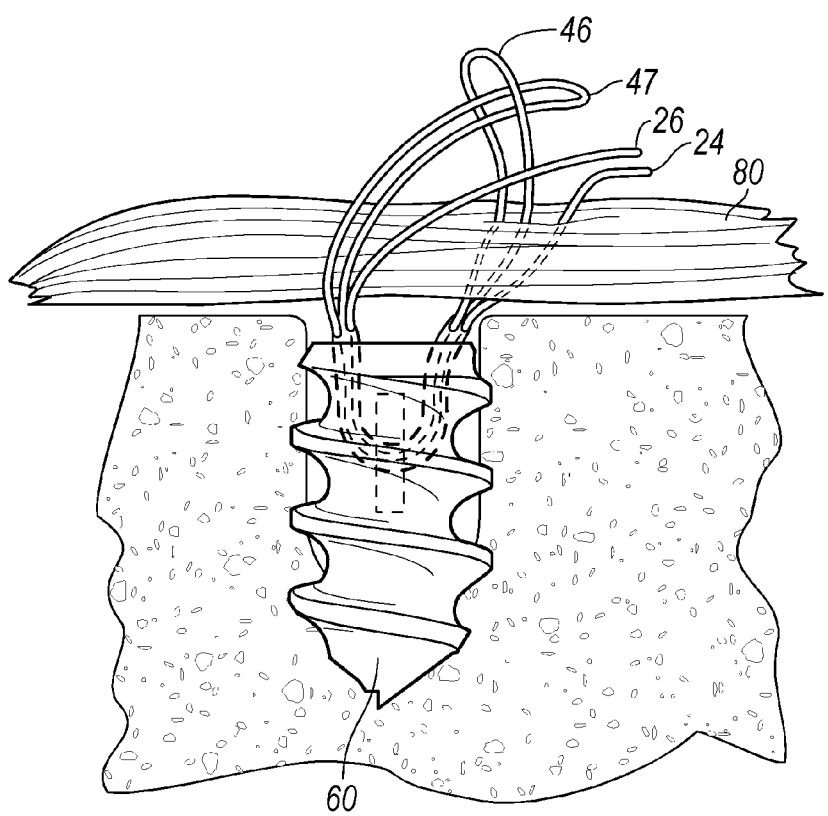
Figure 17C:
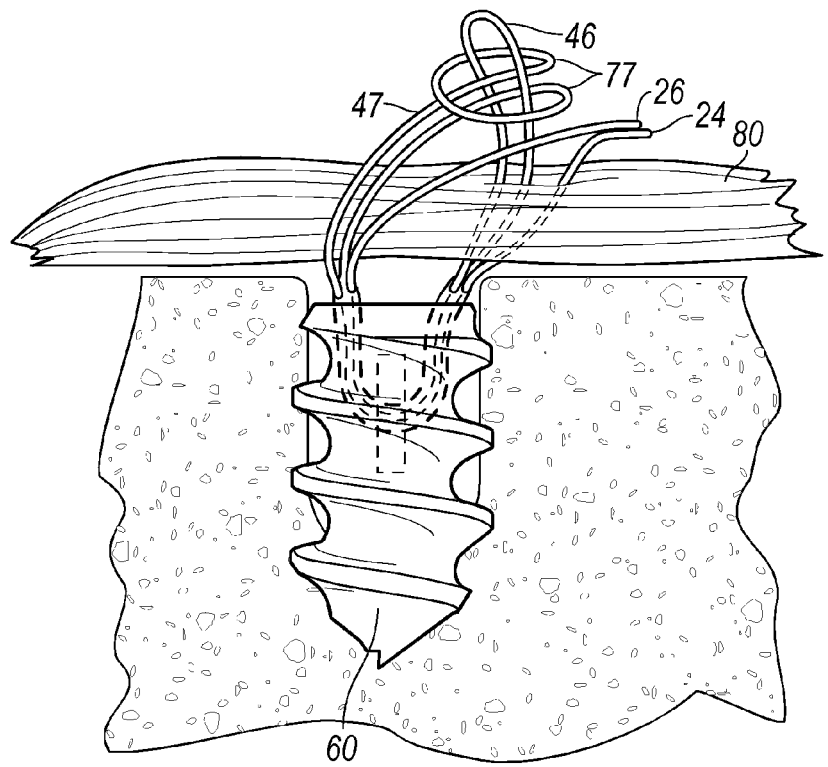

FIGS. 17A-17E represent an alternate method for coupling soft tissue 80 to a bone using the construction of FIGS. 14A and 14B. As shown in FIG. 17A, the first loop 46 and first suture end 24 are passed through an aperture 84 formed in the soft tissue 80. The second loop 47 is passed through the first loop 46.

Figure 17D:
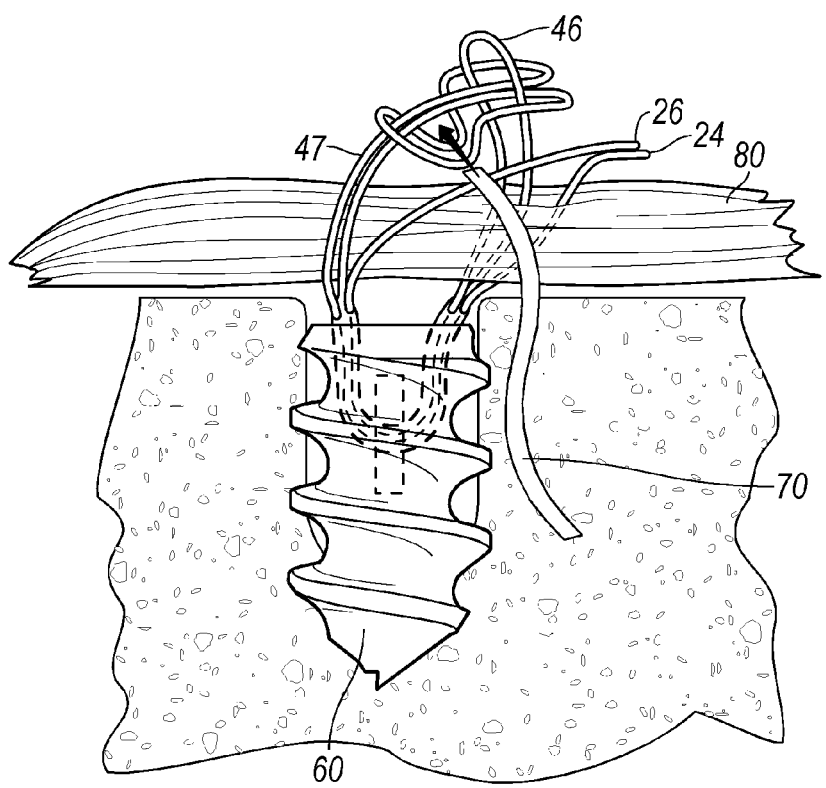
Figure 17E:
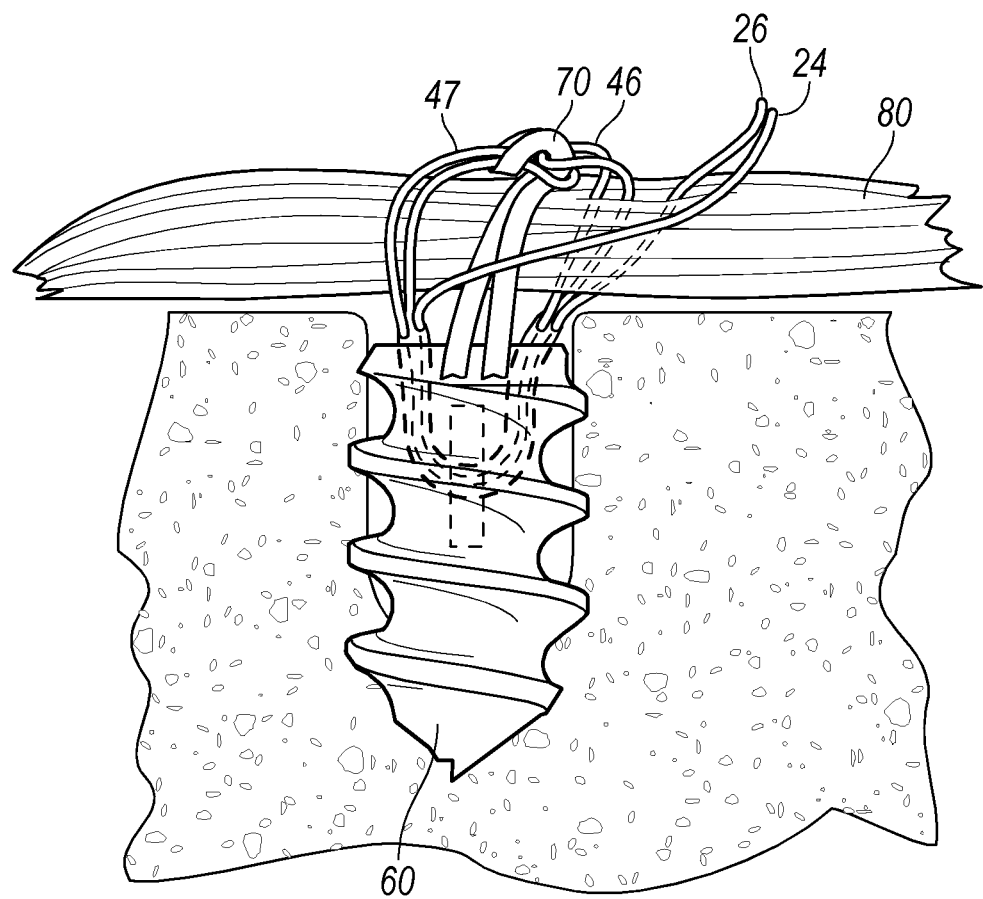

The second loop 47 is then doubled back over the first loop 46 causing a pair of intermediate loops 77. As shown in FIG. 17D, a locking member 70, soft or hard, can then be passed through the pair of intermediate loops 77 or a portion of the first loop 75 to lock the first and second loops 46 and 47 together. As shown in FIG. 17E, tension applied to the suture ends 26, 27 tightens the loops 46 and 47 about the locking member 70. The soft tissue 80 is also fixed to the bone.

Figure 18A:
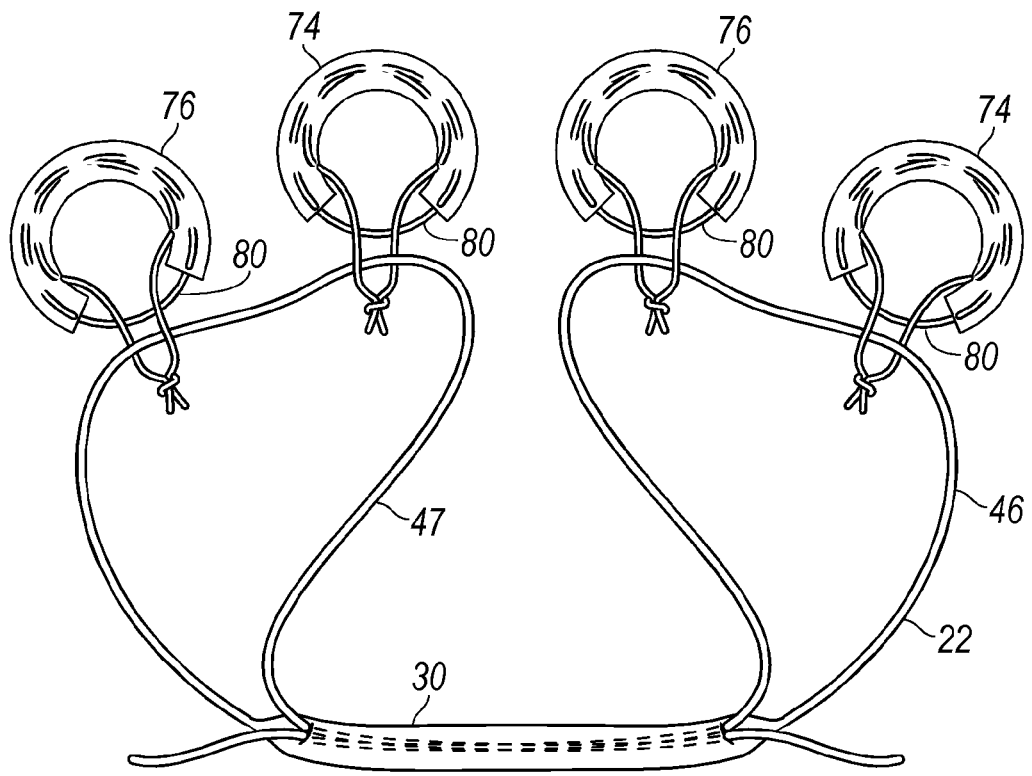
FIGS. 18A-18C represent the coupling of soft tissue to a bone using multiple collapsible loop structures.
Figure 18B:
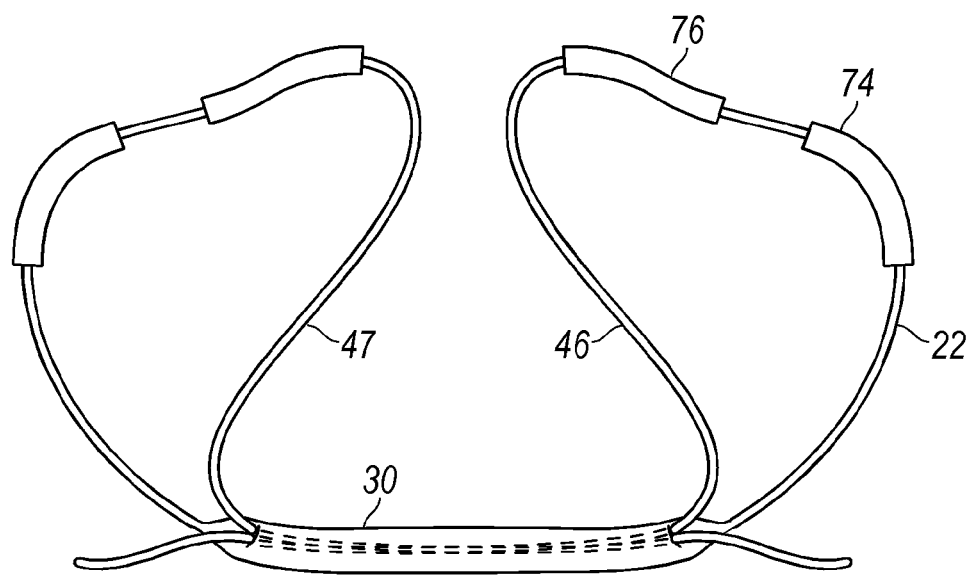
Figure 18C:
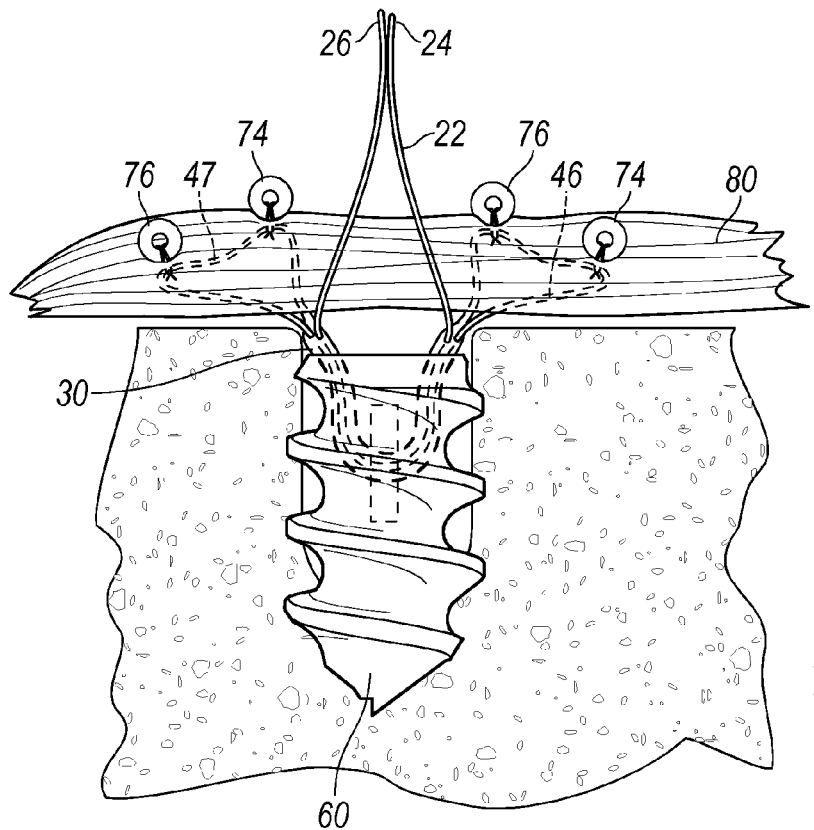

FIGS. 18A-18C represent alternate suture constructions 22 which are used to couple soft tissue 80 and 81 to bone. Disposed about the first and second loops 46 and 47 are collapsible tubes 74 and 76. The tubes 74 and 76 which can be, for example, fabric or polymer, can either be directly disposed about the suture 22 of the first and second loops 46 and 47, or can be coupled to the suture loops 46 and 47 using a separate loop member 81.

As shown in FIG. 18C, the suture construction 22 shown in FIG. 18A or 18B, the collapsible tubes 74 and 76 are passed through the apertures 84 formed in the soft tissue 80. The application of tension to the ends 26 and 27 causes the soft tissue 80 to be drawn against the bone and cause compressive forces to be applied to the collapsible tubes 74 and 76. By tightening the suture which passes through the passage 30, the soft tissue 80 is coupled to the bone without the use of knots.

Figure 19A:
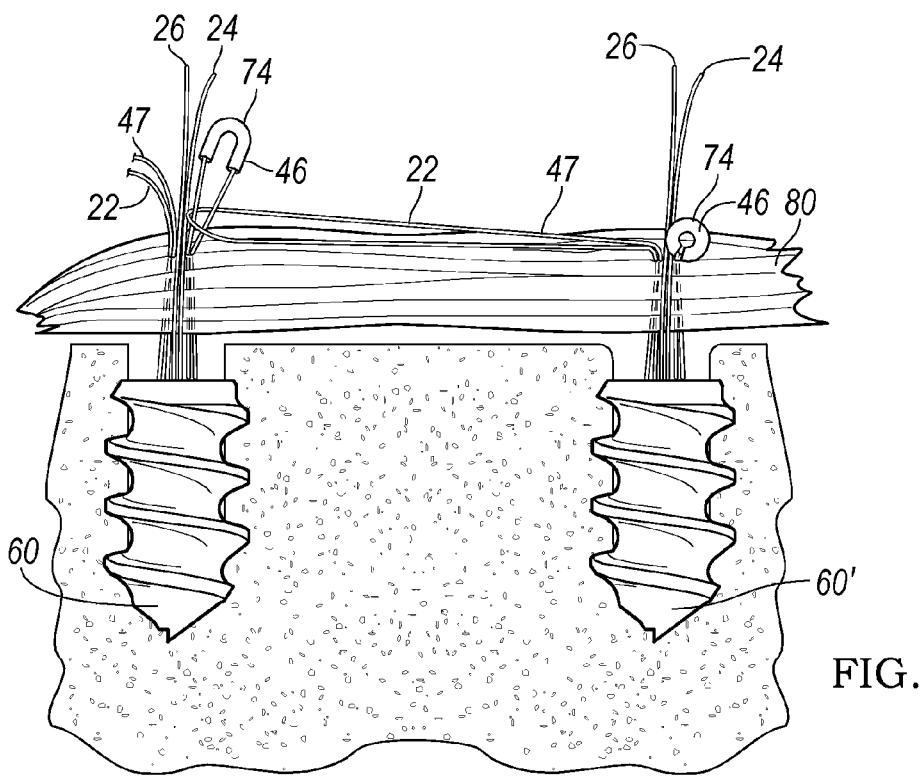
FIGS. 19A-19C represent the coupling of soft tissue to a bone using yet alternate teachings.
Figure 19B:
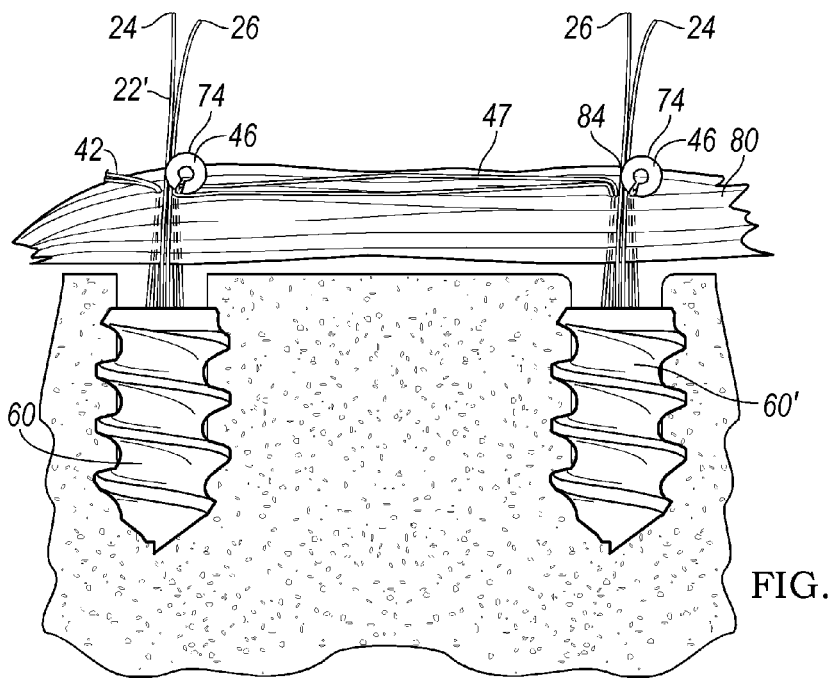
Figure 19C:
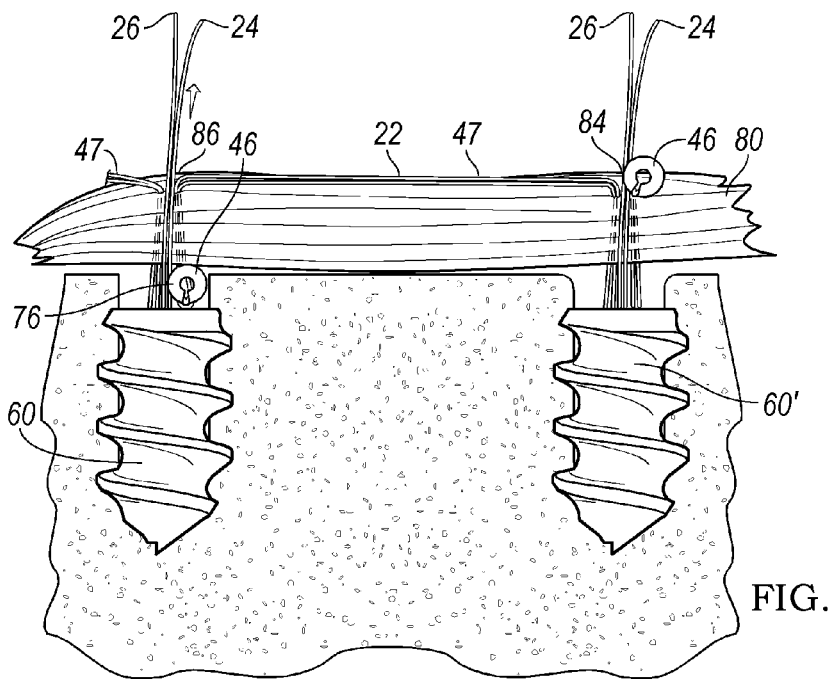

As can be seen in FIGS. 19A-19C, several fixation members 60 and 60' can be coupled to the suture construction 22 to fasten soft tissue 80 to bone. As seen in FIG. 19A, the collapsible tube 74 can be coupled to a first loop 46 while the second loop 47 can be used to couple the first suture 22 to the second fastener 60'. In this regard, they are coupled using a collapsible tube 76 of the second suture 22', thus allowing downward force along the entire length between the fasteners, thus providing bridge fixation as well as point fixation.

As seen in FIG. 19B, tension of the ends 24 and 26 of the first suture 22 draws the second loop 47 into the fixation member 60'. The second loop 47 of the first suture 22 is then coupled to the collapsed tube 76. This couples the first and second fasteners together and applies the downward force.

As seen in FIG. 19C, the second loop 47 of the first suture 22 can be passed through a second aperture 86 in the soft tissue 80. A second loop 47 is then coupled to the collapsible tube 76 associated with the second suture 22'. The collapsed tube 76 of the second suture 22' functions to fix the suture 22' to the fixation member 60'. It is envisioned the collapsed tube 76 can be found within a bore defined in the bone or the fastener 60.

Figure 20A:
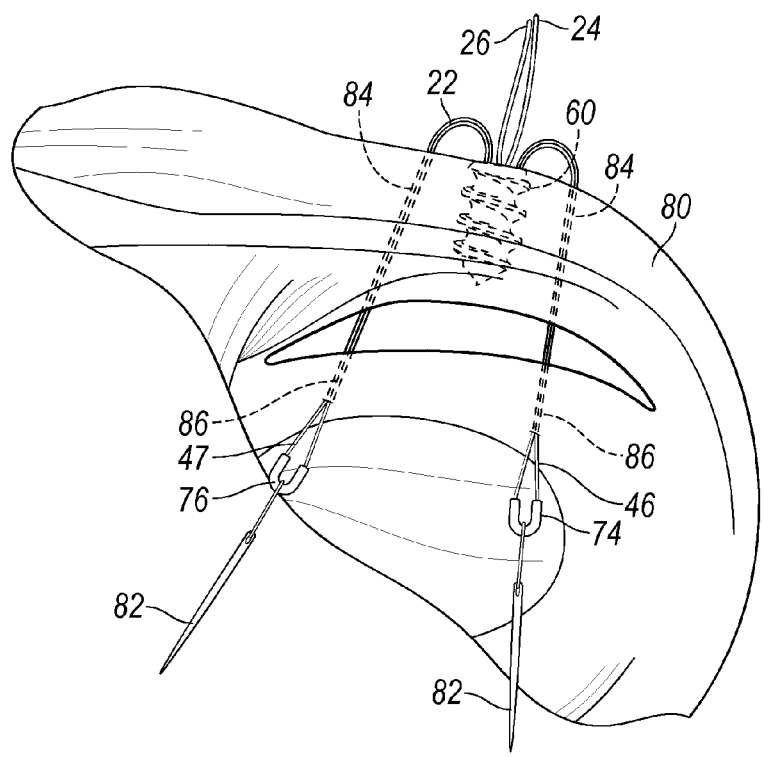
FIGS. 20A and 20B represent a meniscal repair according to the present teachings.
Figure 20B:
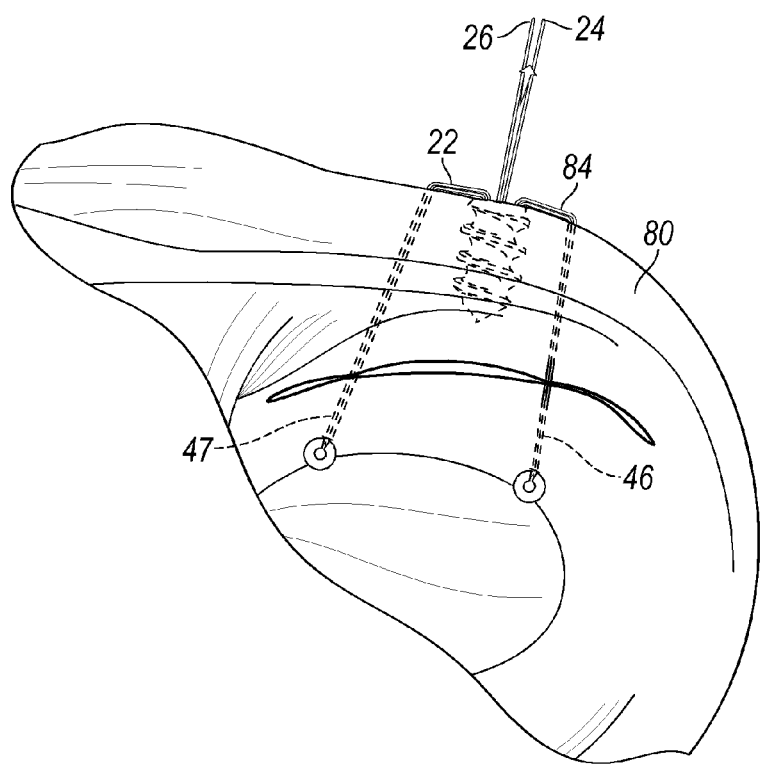

FIGS. 20A and 20B represent the use of a suture construction 22 to repair a meniscus. Fasteners 82 are coupled to first and second loops 46 and 47.

After the fixation member 60 is coupled to bone or soft tissue, the first loop 46 is passed through a first aperture 84 in a first portion of the meniscus. The first loop and collapsible tube 74 is then passed through a second aperture 86 and a second portion of the meniscus. The second loop 47 and second collapsible tube 76 are similarly passed through the meniscus. Tension is applied to the first and second ends 24 and 26 of the suture 22 to pull the meniscus together. As seen in FIG. 20B, a first and second collapsible tube 74 and 76 are constricted so as to couple the suture to the meniscus.

Figure 21:
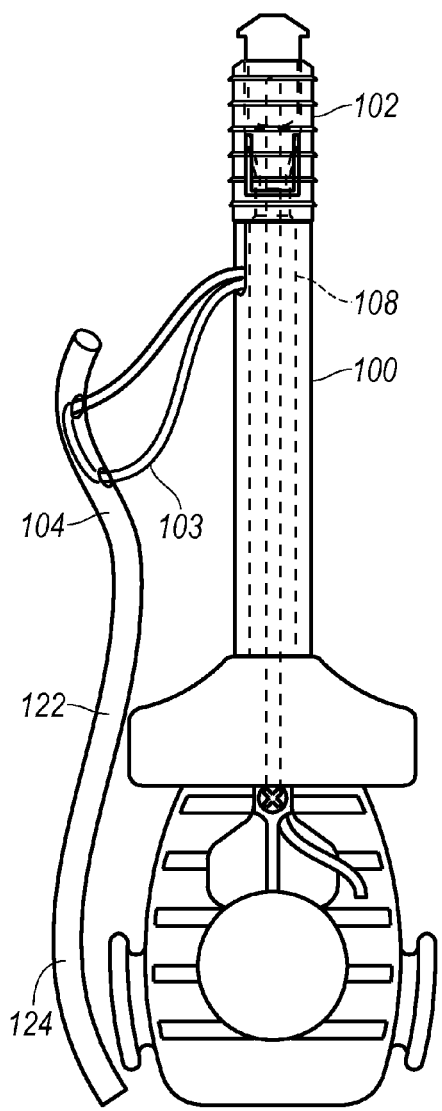
FIG. 21 represents an insertion tool with associated fastener and soft tissue anchor.

FIG. 21 represents a tool 100 with associated fastener 102 and soft tissue anchor 104. The tool 100 has a handle portion 106 which releasably engages the fastener 102. Associated with the handle portion 106 is a hollow longitudinal suture 103 which accepts a soft tissue anchor 104. Disposed at a distal end 110 of the hollow longitudinal portion 108 is a slot having a portion of the soft tissue anchor 104 disposed therethrough. The distal end 110 is further configured to support the fastener 102 for insertion into a bore defined within bone 112.

Figure 22:
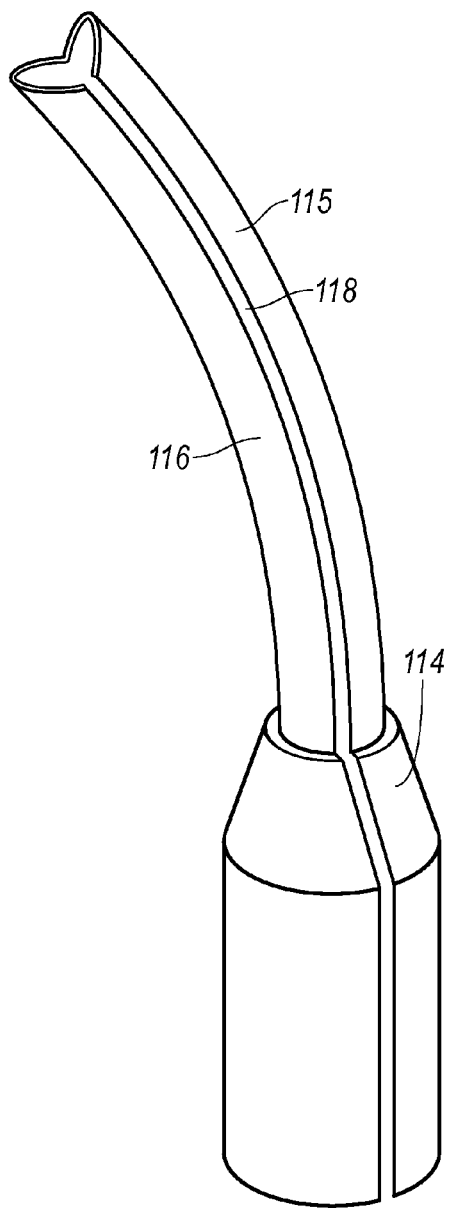
FIG. 22 represents an insertion sleeve associated with the tool shown in FIG. 21.

FIG. 22 represents an insertion guide 115 having a handle portion 114 and a curved longitudinal guide tube 116. The longitudinal guide tube 116 and handle portion 114 slidably accept the fastener 102 and soft tissue anchor 104. The curved longitudinal tube 116 and handle portion 112 define a slot 118 which also slidably accepts the suture 103 of soft tissue anchor 104.

Figure 23:
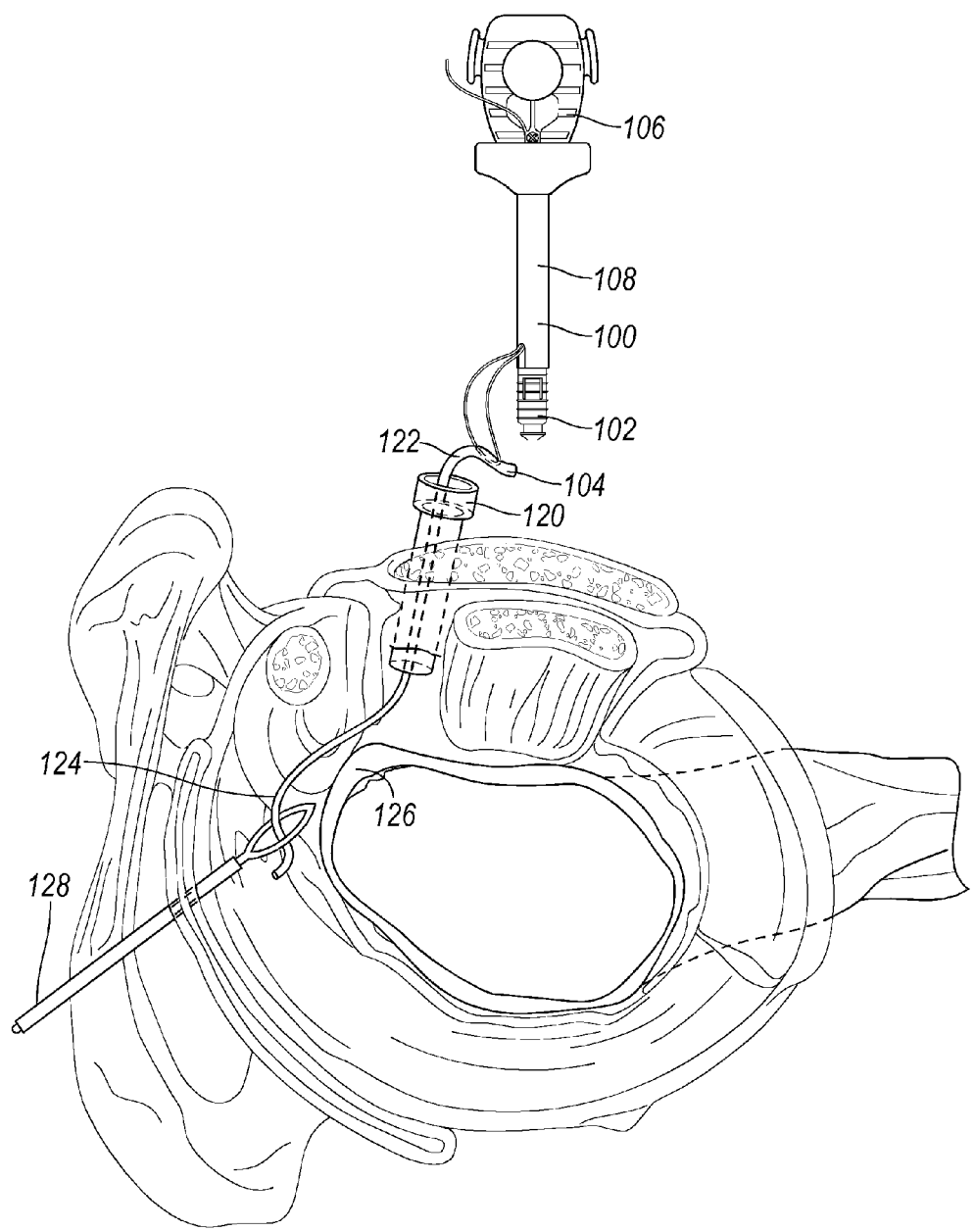
FIGS. 23-31 represent the repair of a rotator cuff using a tool shown in FIG. 21.

FIGS. 23-38 generally depict the repair of labral tissue of a glenoid. While the repair shown generally relates to a specific anatomical injury, it is envisioned the teachings herein can be applied to other anatomical regions which require the coupling of soft tissue to bone. For example, a meniscal repair in a knee may be performed using similar techniques. As shown in FIG. 23, access to the region of the injury is made through a tube 120. At this point, a collapsible tube 122 having an extended portion 124 is threaded through tube 120 into close proximity of the soft tissue 126 to be coupled to bone. A suture grabber 128 such as a speed pass by Biomet Sports Medicine is used to pierce the soft tissue 126 and to grab the extended portion 124 of the collapsible tube 122. This extended portion 124 is then pulled through the soft tissue 126.

Figure 24:
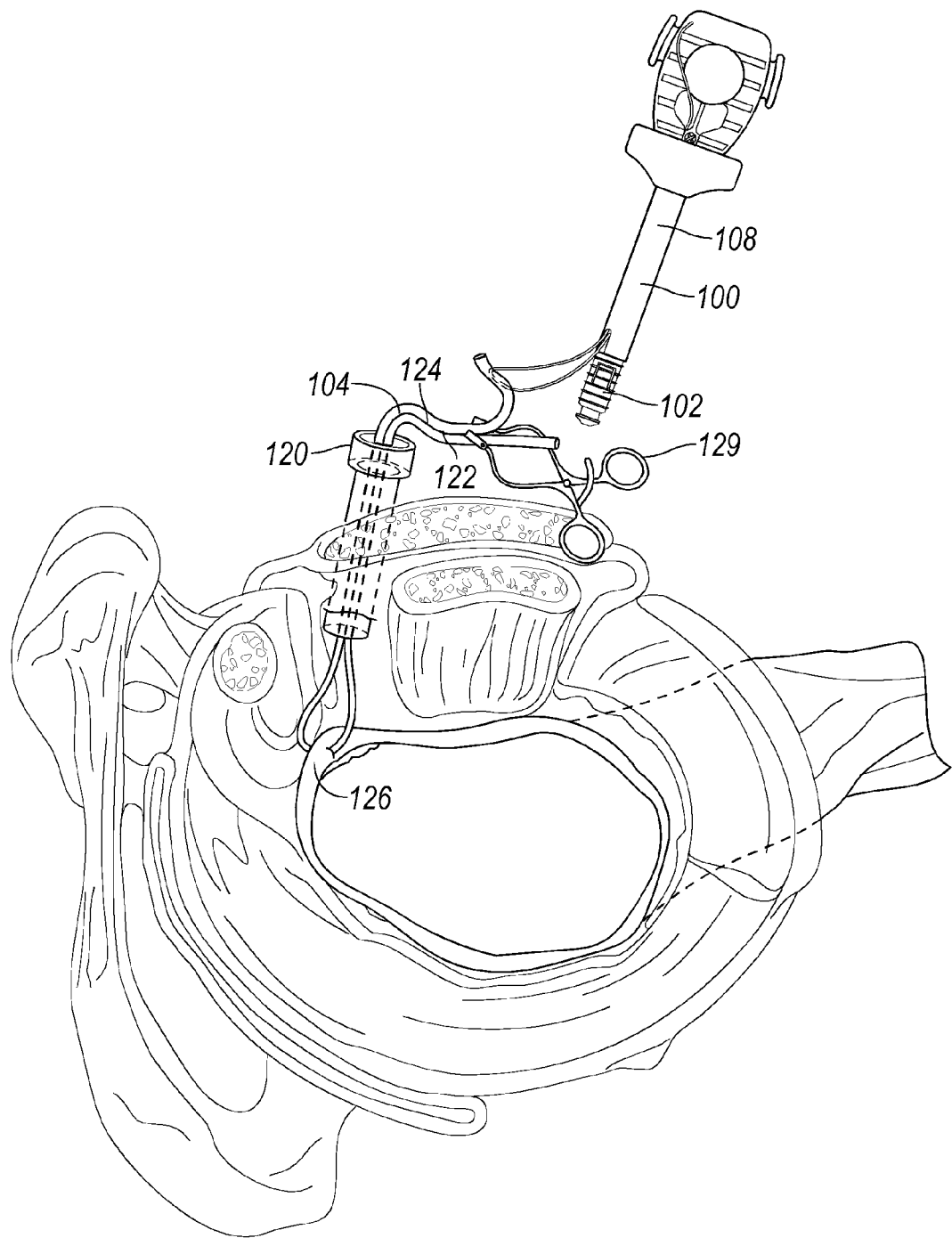
Figure 25:
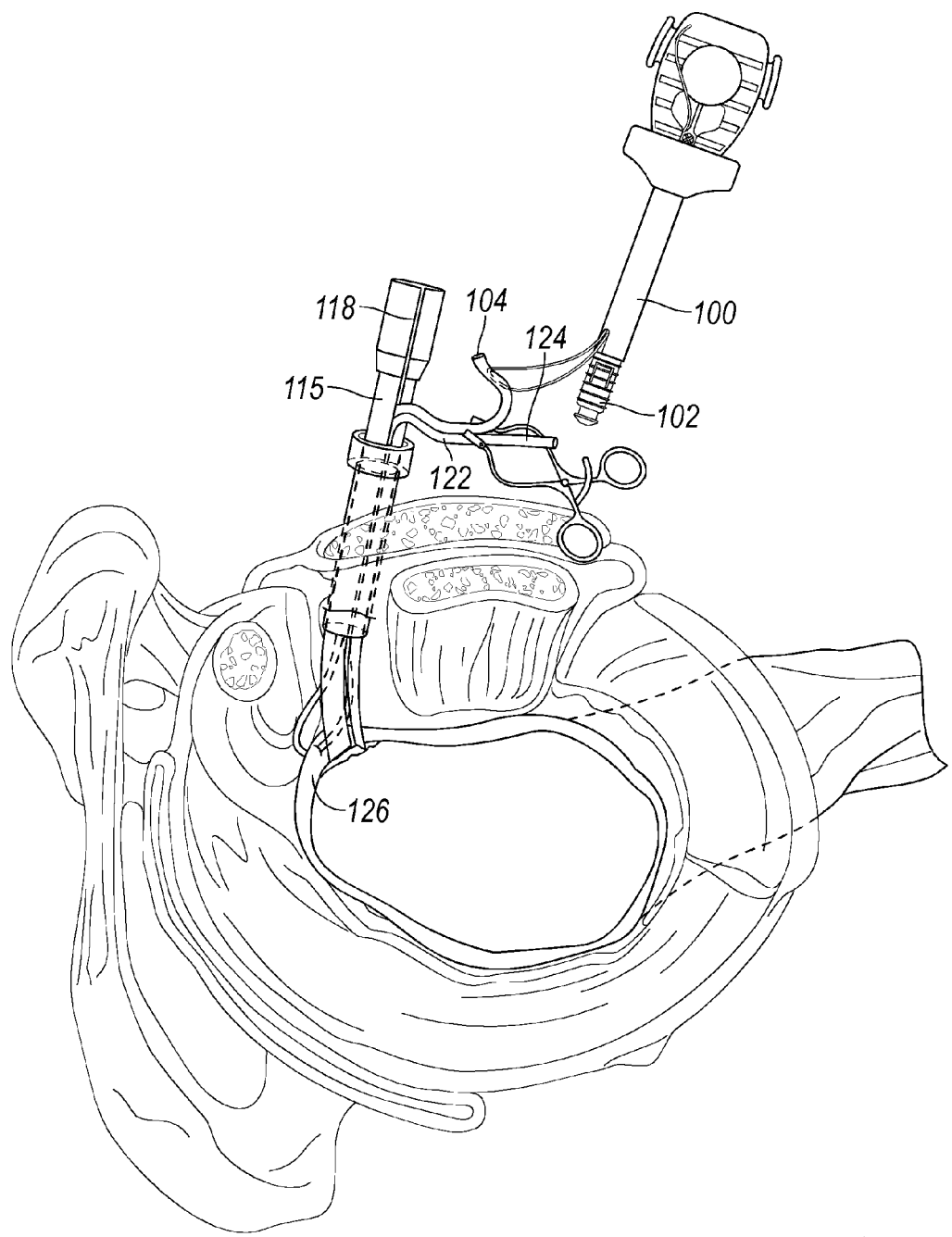

As shown in FIG. 24, the extended portion 124 of the collapsible tube 122 is fed back out the access tube 120 and clamped with clamp 129 so as to prevent inadvertent translation with respect to the tube. As shown in FIG. 25, the insertion sleeve 115 is placed through the access tube 120. The collapsible tube 122 is placed through the slot 118 defined in the handle portion 114 and longitudinal guide tube 116.

Figure 26:
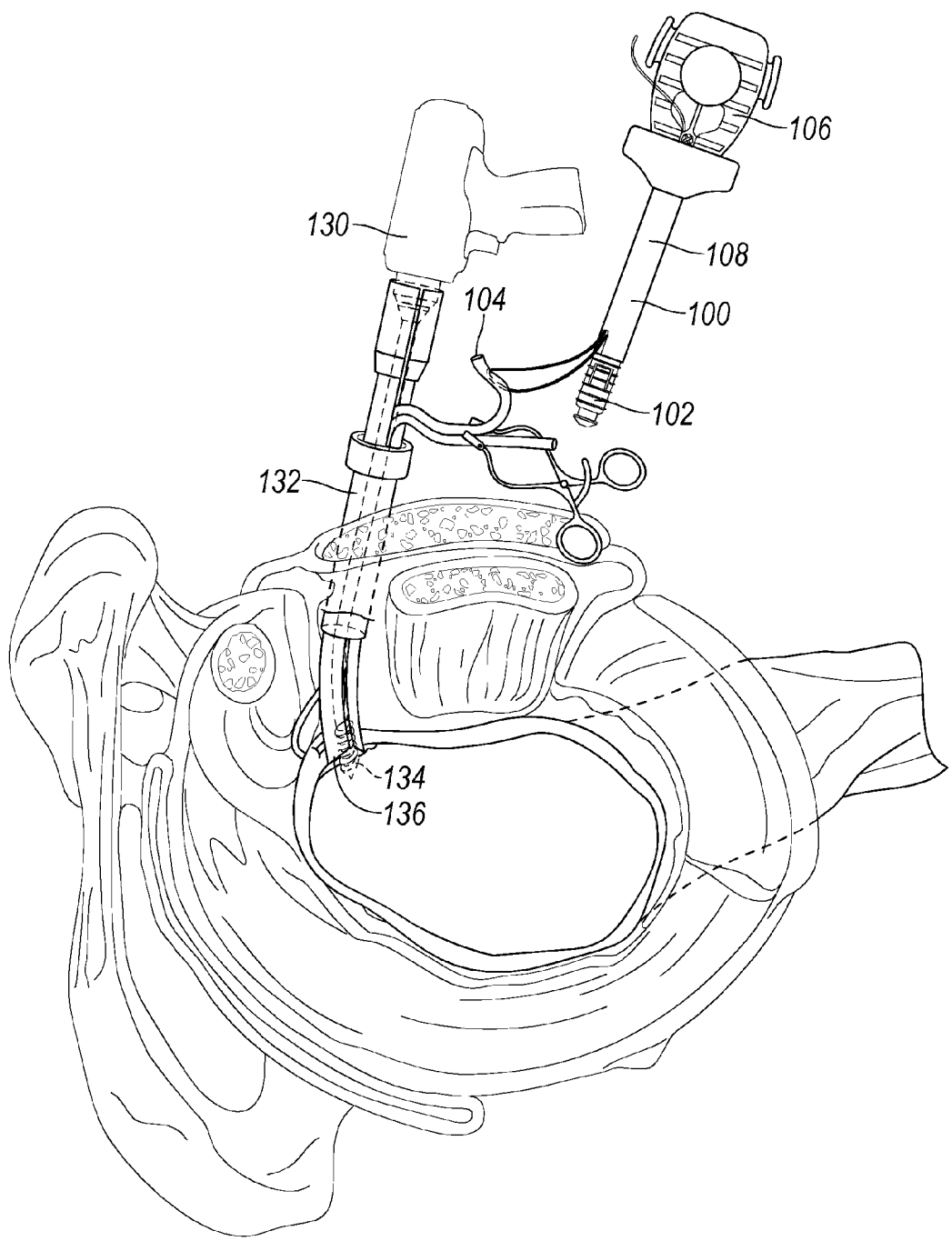
Figure 27:
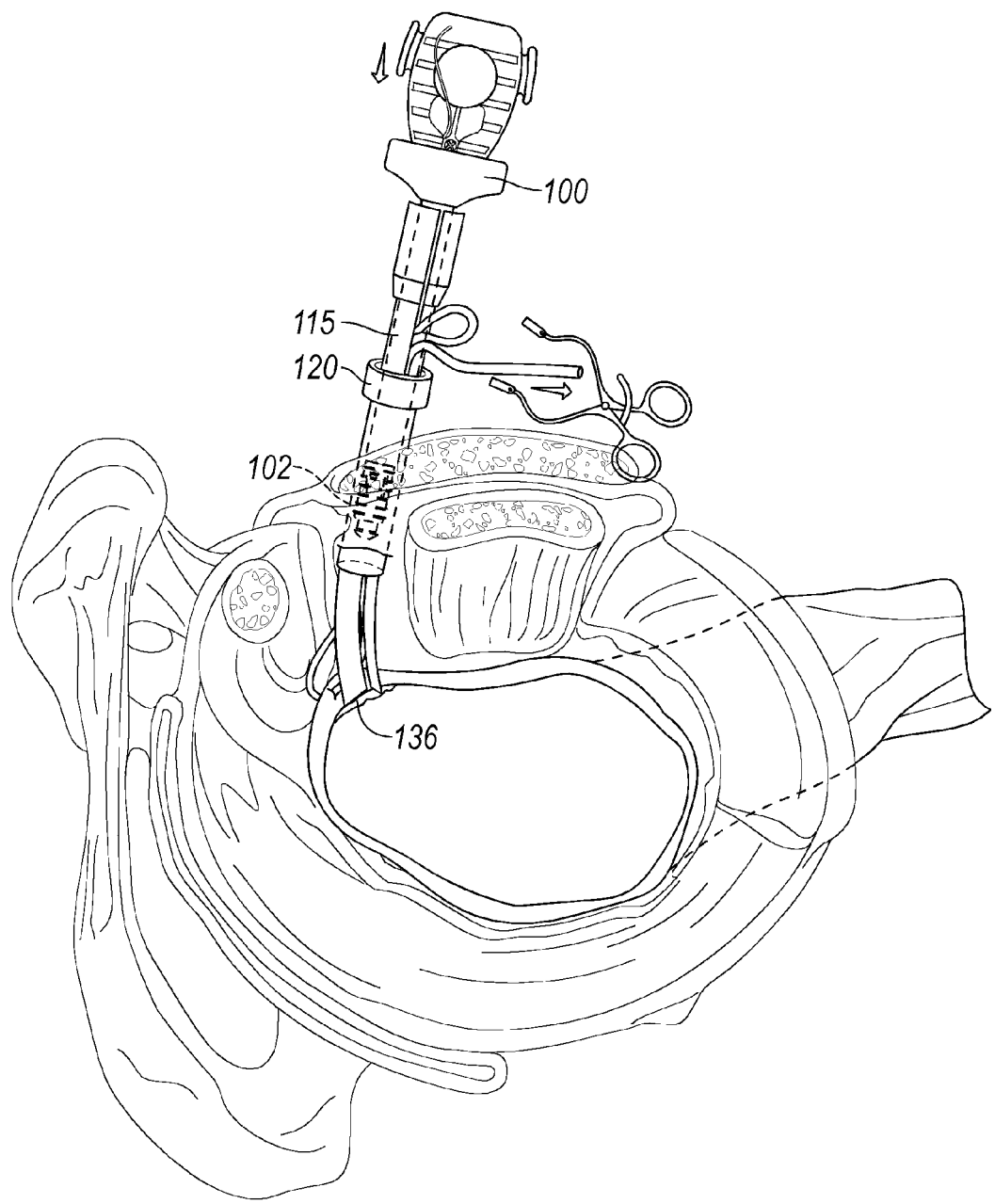

FIG. 26 shows a drill 130 having a flexible drive shaft 132 and a bone cutting drill bit 134. The drill bit 134 is placed through the guide tube 116 to form a bore 136 in bone at a location adjacent to a soft tissue repair. It is envisioned the bore 136 can be placed under or adjacent the soft tissue repair.

Figure 28:
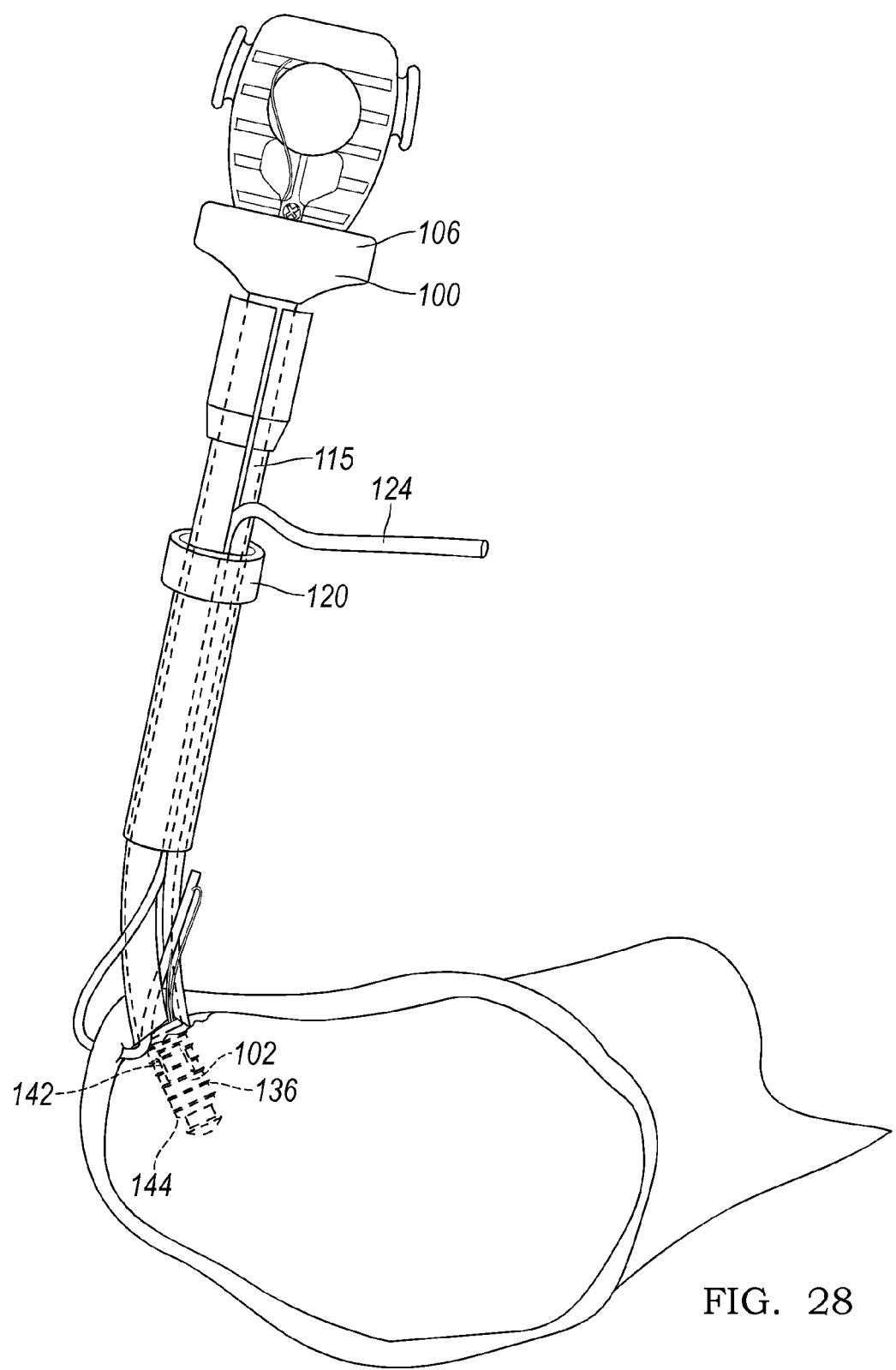
Figure 29:
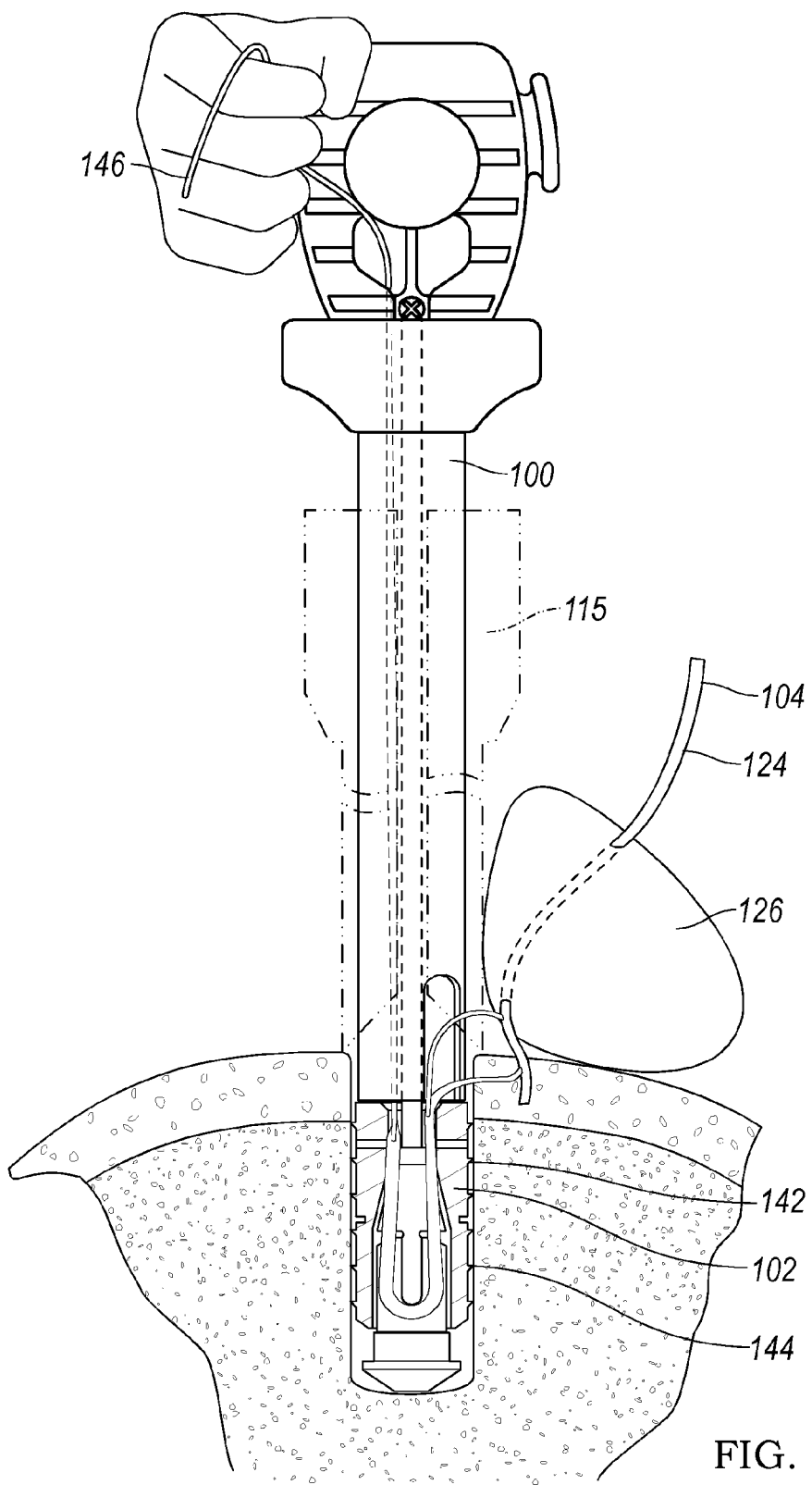

After the bore 136 has been formed in the bone, the tool 100, fastener 102, and associated soft tissue anchor 104 are placed through the insertion guide 115. As shown in FIG. 28, the fastener is inserted into the bore 136. It is envisioned the fastener 102 can be a two-part fastener having a first insertion portion 140 and a locking portion 142. The locking portion 142 can have a plurality of expandable bone engaging members 144.

Figure 30:
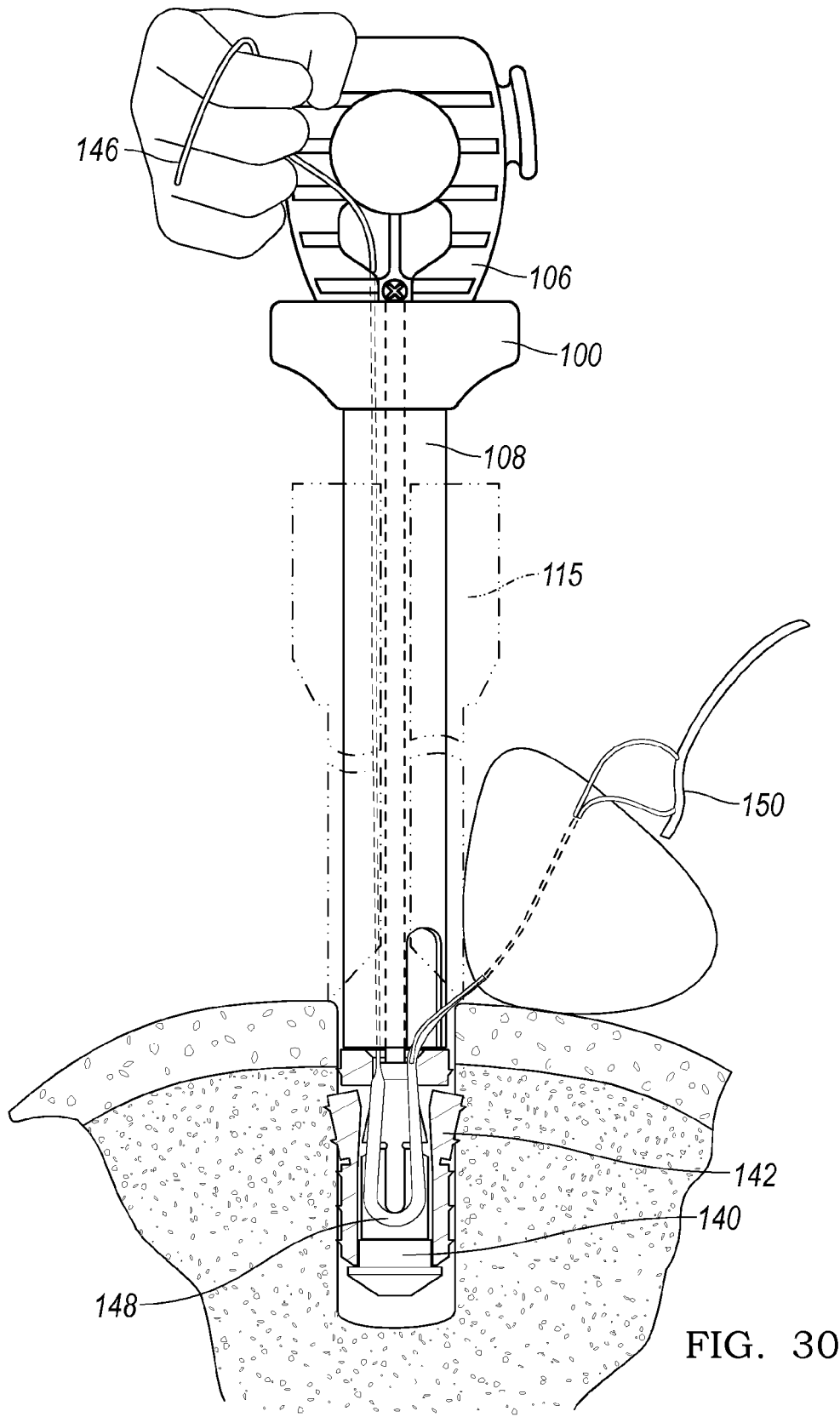

As seen in FIG. 30, the pair of sutures 146 can be pulled through the soft tissue 126. The sutures 146 can be coupled together using a suture construction shown in FIG. 1A or 1B. In this regard, the suture 146 can be looped through an integrally formed collapsible member or tube 148 which can be used to fix the suture construction with respect to either the insert or locking portion 140, 142 of the fastener.

Figure 31:
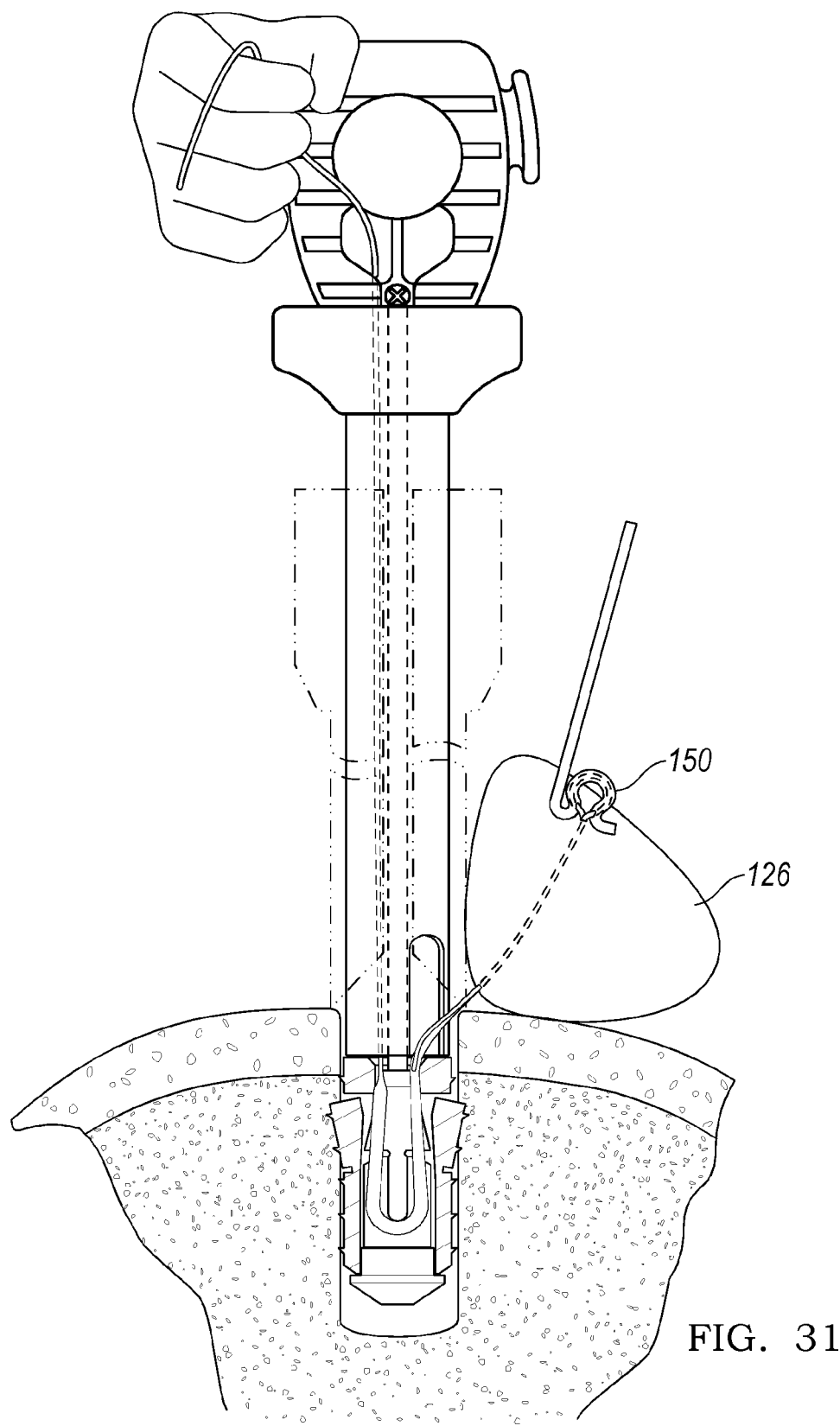
Figure 32:
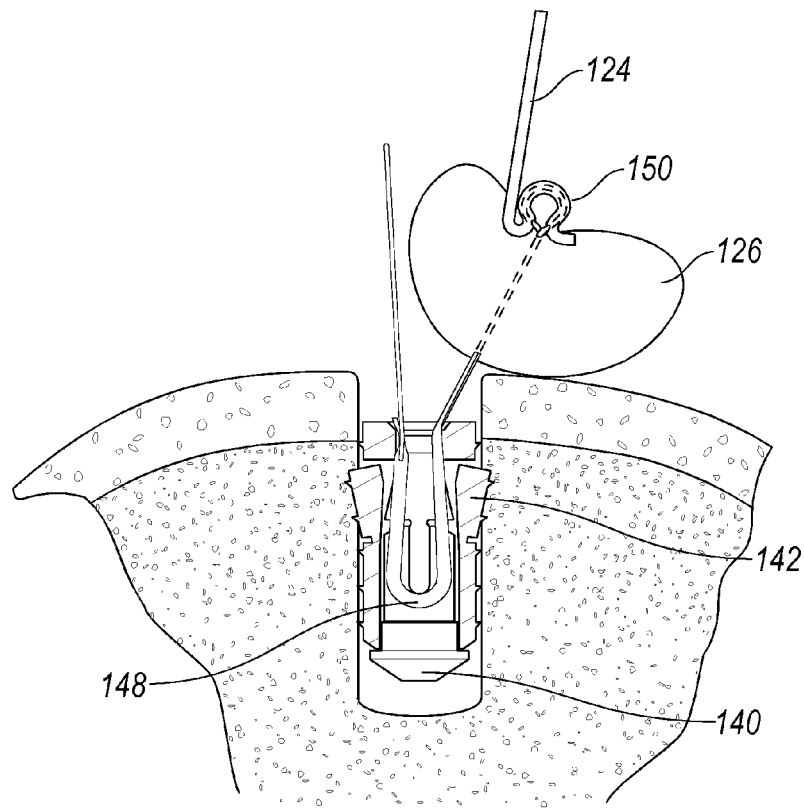
FIGS. 32-38 represent alternate methods for tying a suture anchor to the fastener.
Figure 33A:
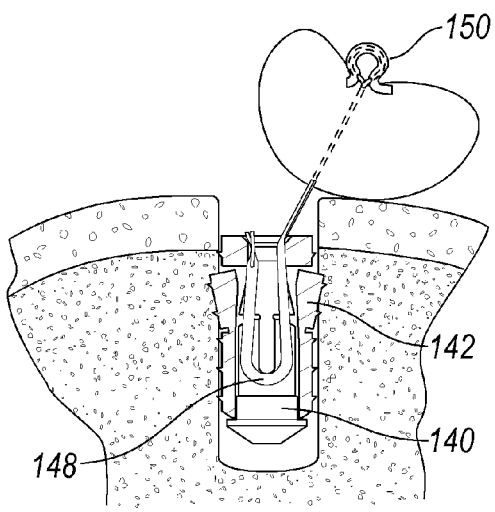
Figure 33B:
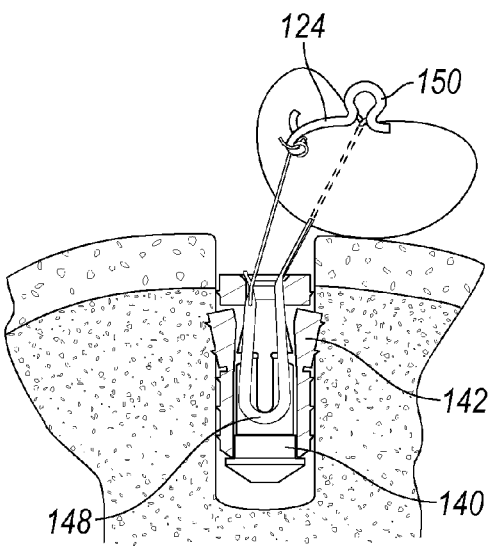

As shown in FIG. 31, when tension is applied to the suture 146 through the tool 100, a collapsible portion 150 of the collapsible tube engages the soft tissue 126. As seen in FIGS. 32-33B, once the collapsible portion 150 of the collapsible tube is set, the tool 100 can be removed from the insertion guide 115. At this point, the end of the longitudinal tube can be removed, or can be tied to the suture 146.

Figure 34:
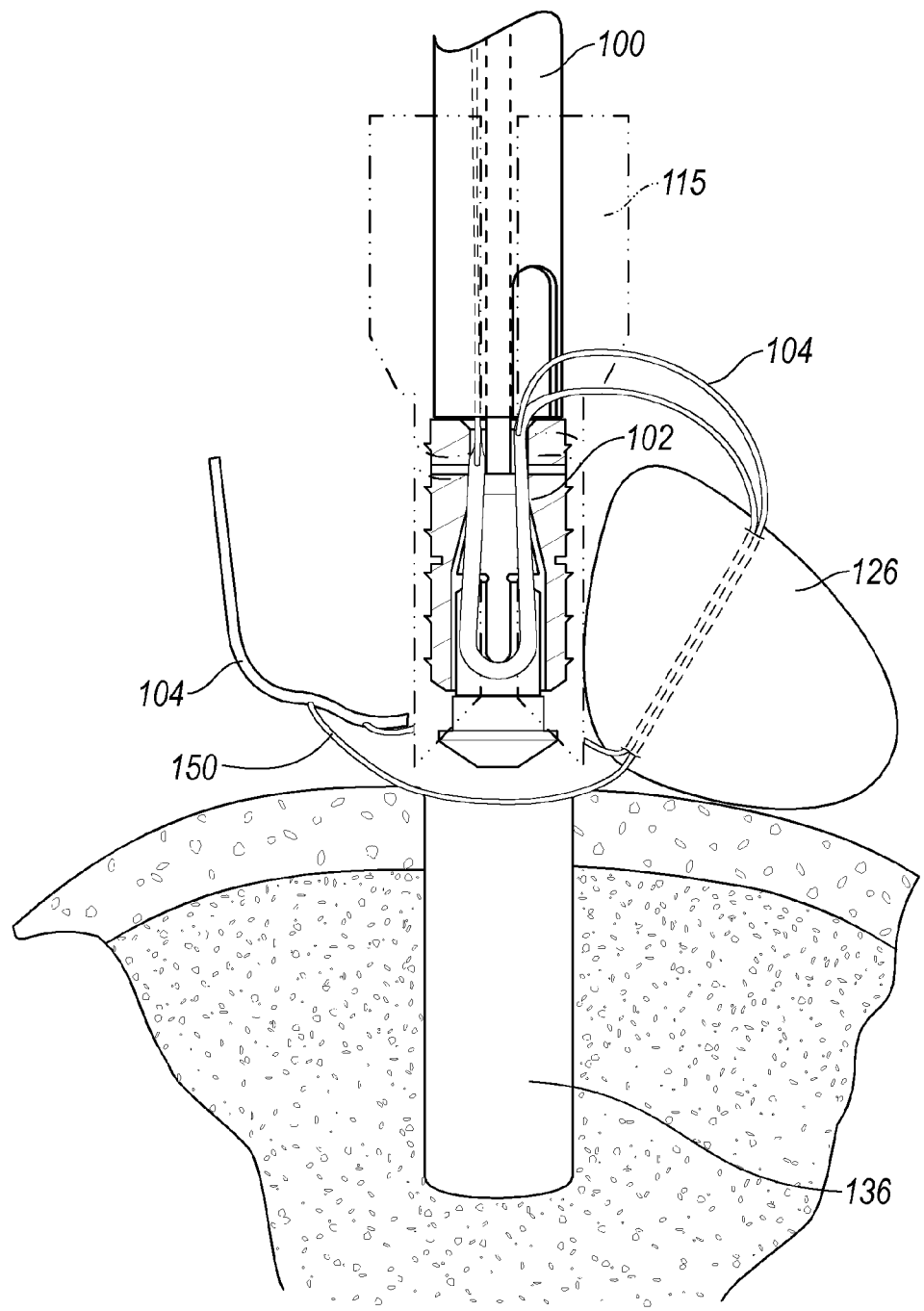
Figure 35:
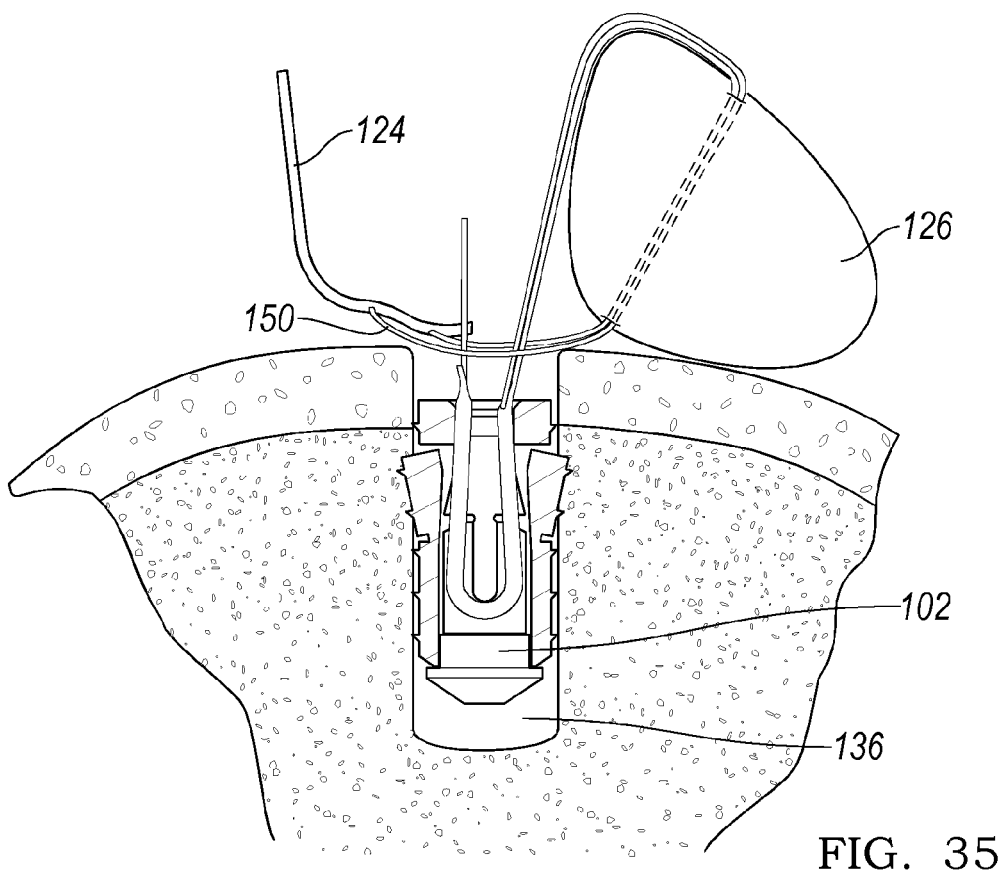
Figure 36:
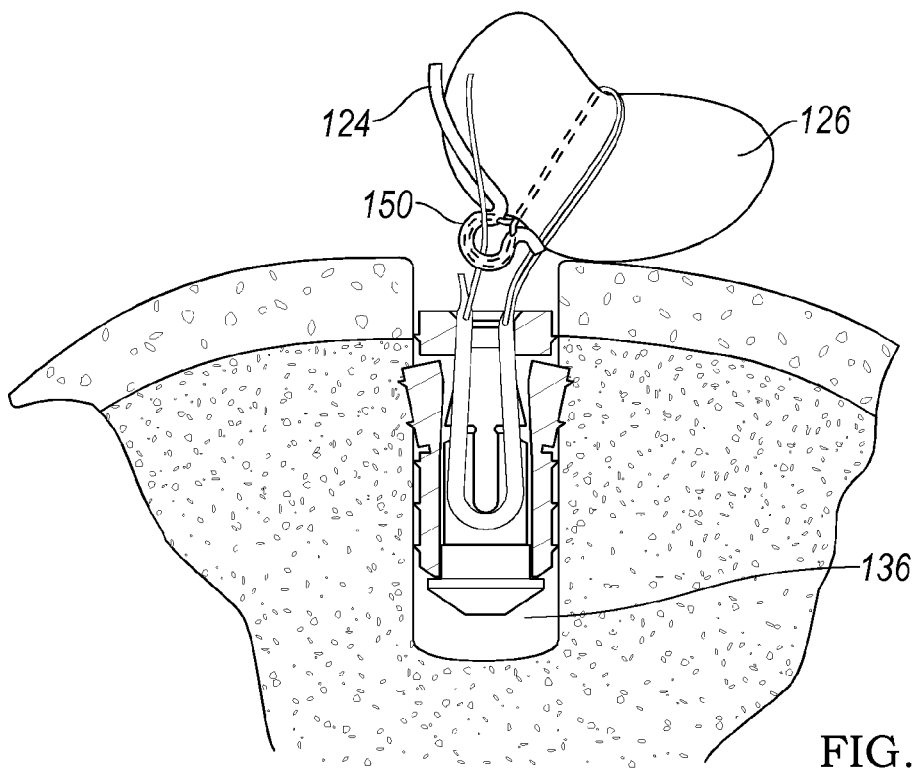

FIGS. 34-36 represent an alternate method for coupling a suture construction 104 to the fastener 102. Shown is a fastener 102 being passed through the loop of the suture. In this regard, the fastener 102 is passed through the loop of the suture prior to insertion of the fastener 102 within the bore 136 in the bone. After removal of the tool 100, tension is applied to the ends of the suture to constrict the collapsible portion 150 of the collapsible tube. This tensioning pulls the soft tissue 146 into a position with respect to the fastener 102.

Figure 37:
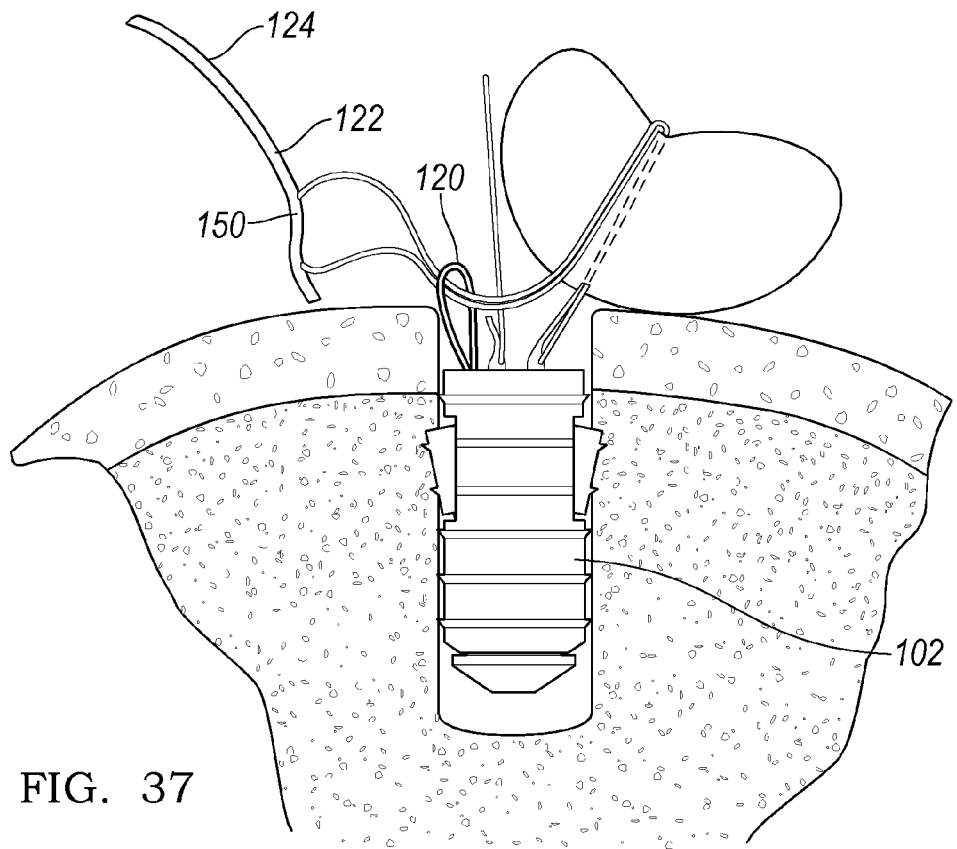
Figure 38:
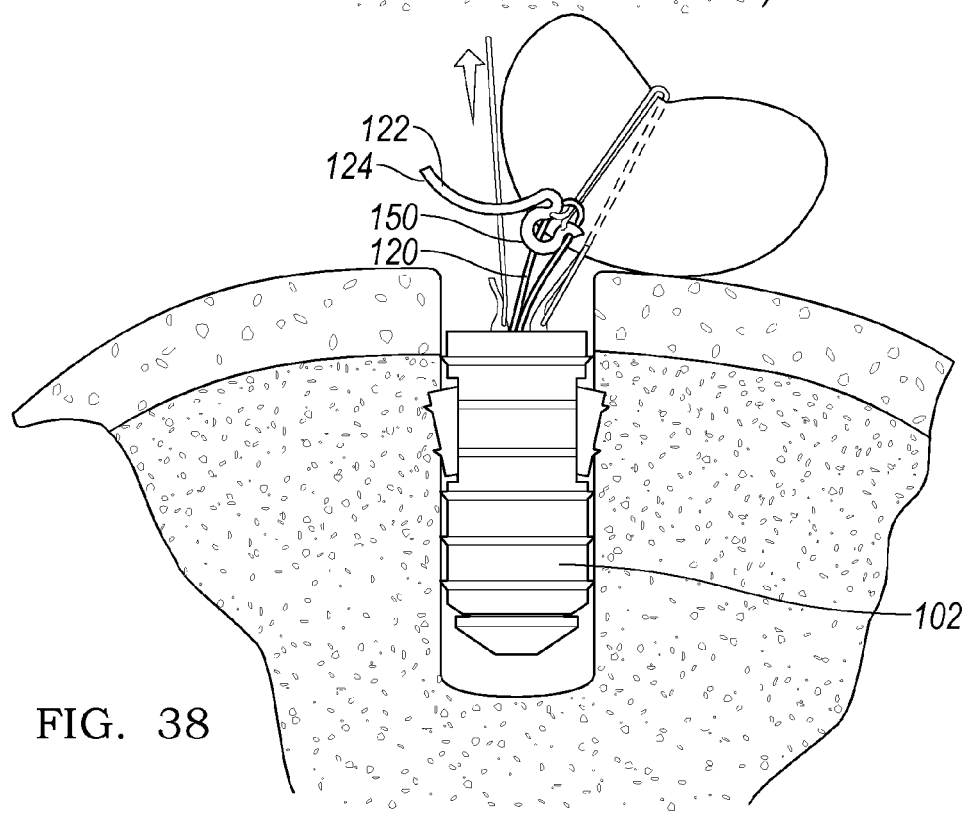

As shown in FIGS. 37 and 38, the fastener 102 can have an associated integral loop 120. The integral loop 120 can be a suture or can be an integral polymer construction. The compressible tube 122 can be threaded through the integral loop 120. Application of tension onto the suture causes the collapsible portion 150 of the collapsible tube to bear against the integral loop 120 and the soft tissue. It is envisioned the integral loop can be elastically deformable or can be fixed with respect to the fastener.

Figure 39:
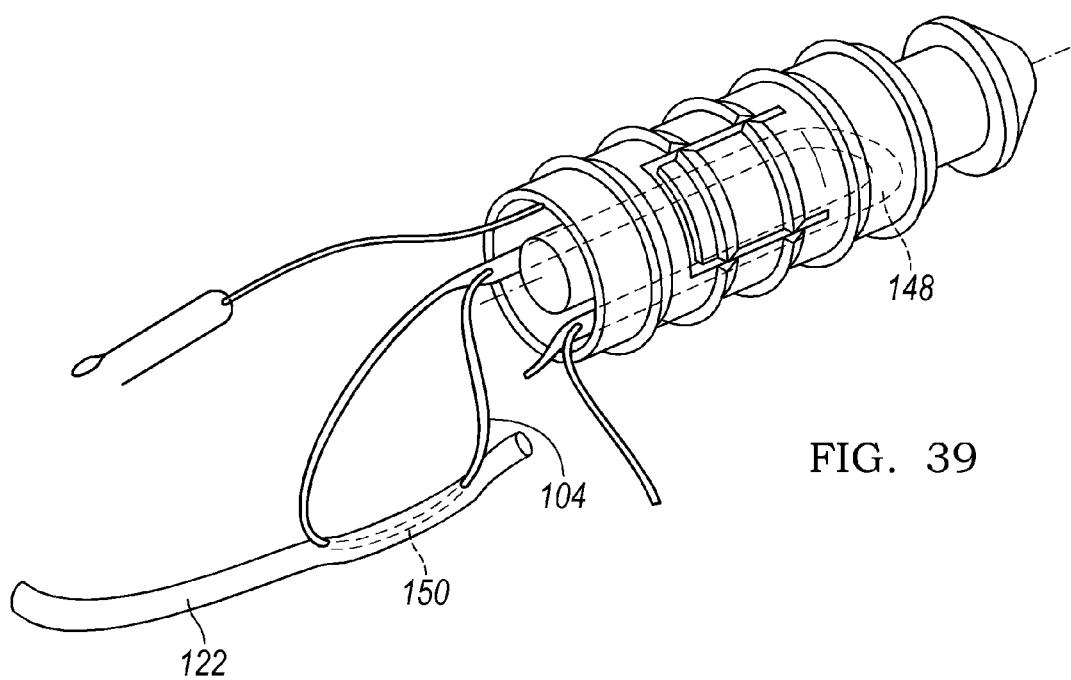
FIG. 39 represents the suture anchor coupled to a two-piece fastener.

FIG. 39 represents a suture construction coupled to a two-piece fastener 102. The suture construction 104 can be threaded through the aperture formed within the first or second portions of the fastener 102. As shown, an integrally formed collapsible tube portion 148 can be disclosed within the aperture of the fastener. Upon application of tension onto the suture, the tension will cause the collapse of this second collapsible tube portion 148, thus locking the suture to the fastener body 102.

FIGS. 40-44 represent an alternative system and method of coupling soft tissue to bone. By way of non-limiting example, a fastener 102 can be coupled to the bone as described above and shown in FIGS. 23-30. Subsequent to this, the collapsible portion 150 of the tube 104 can be passed through the soft tissue 126.

Figure 40:
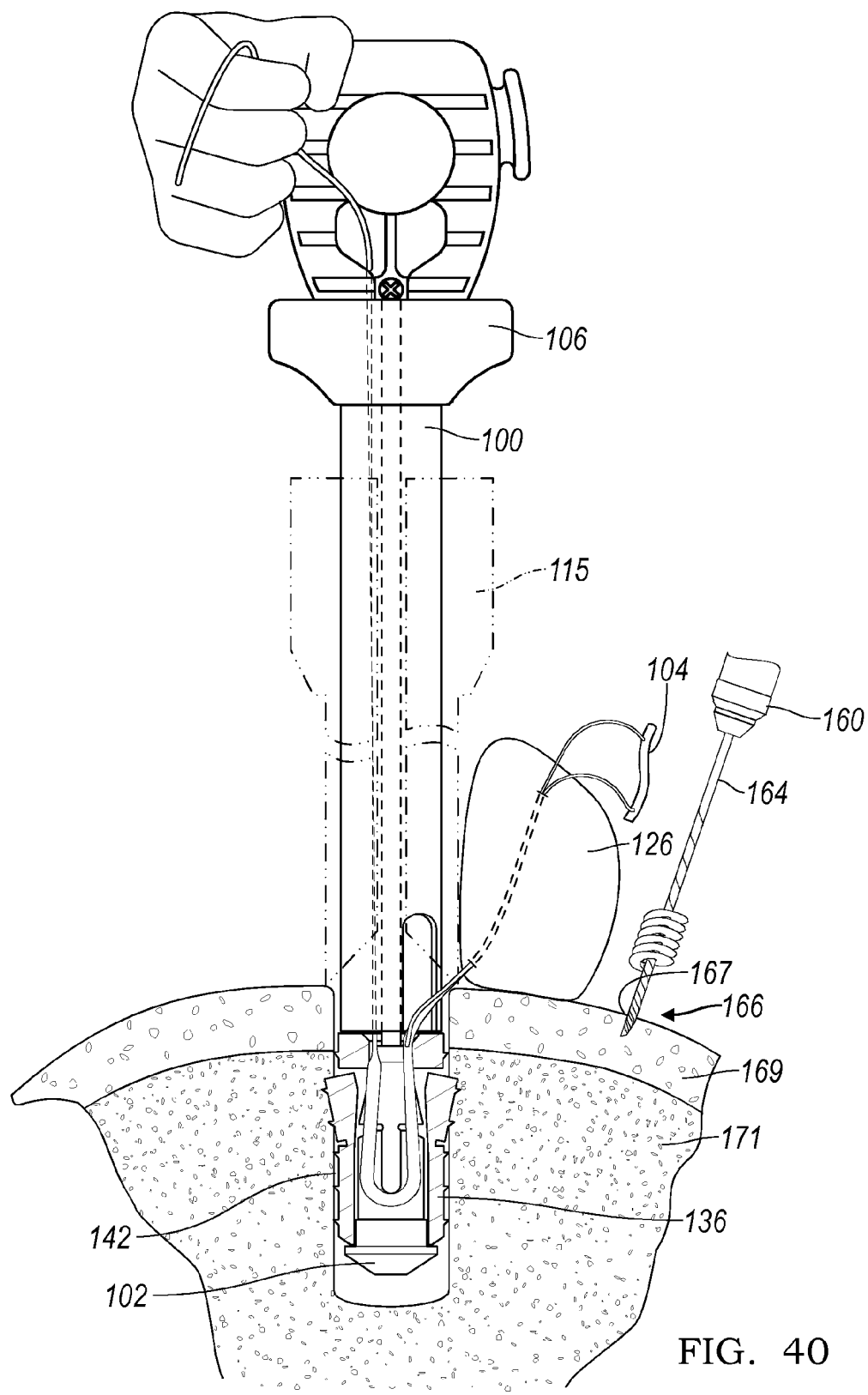
FIGS. 40-44 represent an alternate system and method of coupling soft tissue to the bone.
Figure 41:
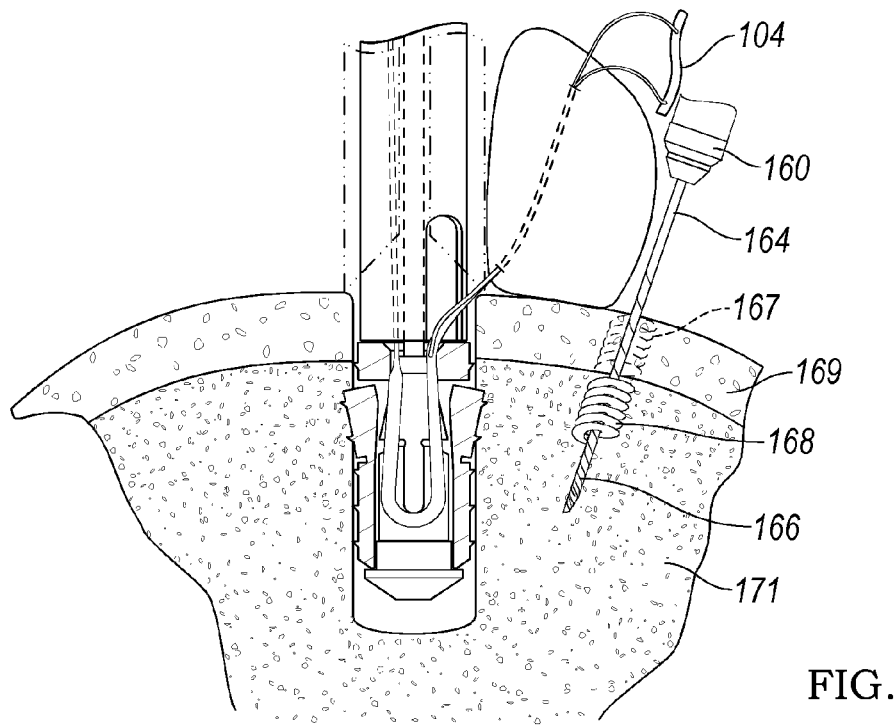
Figure 42:
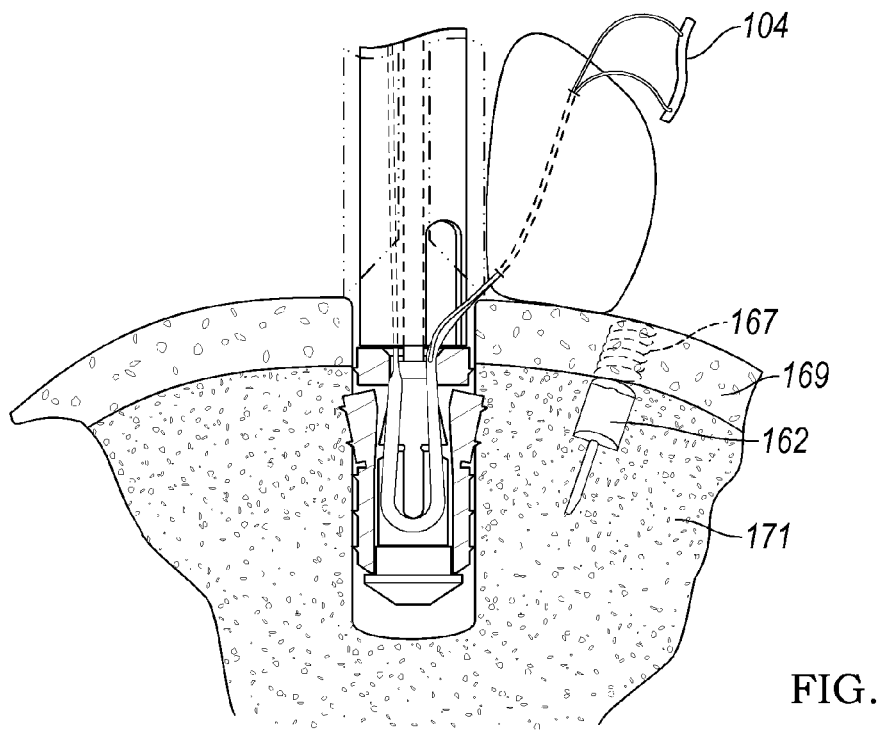

As best seen in FIGS. 40-42, a drive tool 160 is used to form a soft tissue engagement site 162 in a bone structure. The tool 160 has a drive (not shown) which rotates a bone cutting bit 164. The bone cutting bit 164 has a first portion 166 configured to drill a hole 167 through cortical bone and a threaded second portion 168. The threaded second portion 168 is configured to cut threads in the cortical 169 and cancellous bone 171 structures. This is accomplished by advancing the cutting bit 164 into the bone at a predetermined rate while rotating the bit at a predetermined speed. As shown in FIG. 41, after the second portion 168 has entered the cancellous bone 171, the bit is rotated while keeping the rotating tool 160 in a substantially stationary position. The thread cutting threads of the second portion 168 then displace cancellous bone 171, forming the cavity 162. The bit is removed by rotating the thread cutting threads through the threads formed in the cortical bone 169.

Figure 43:
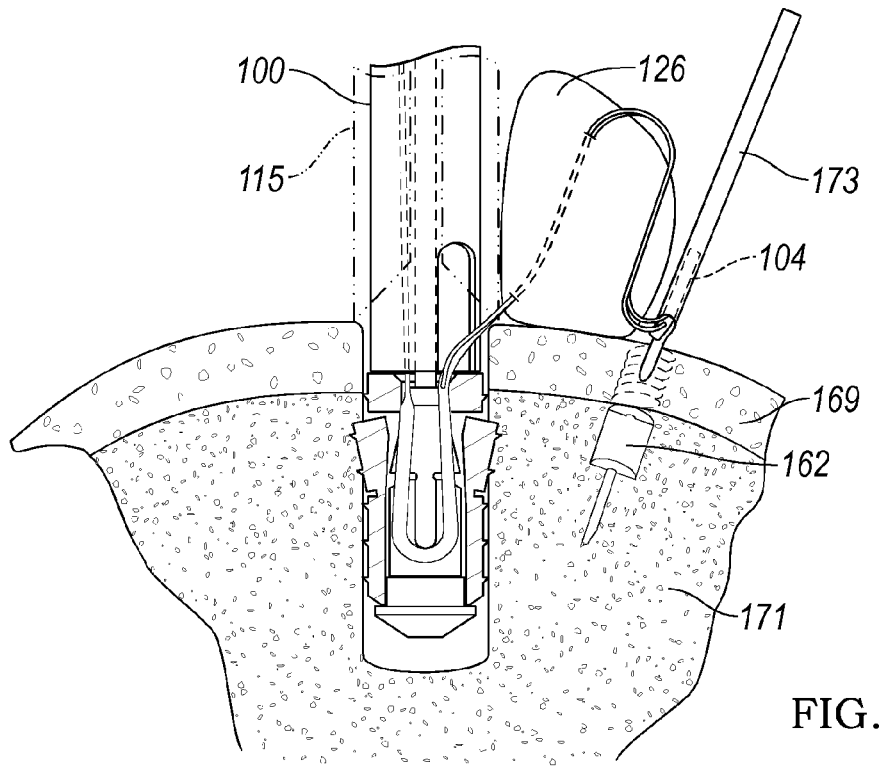
Figure 44:
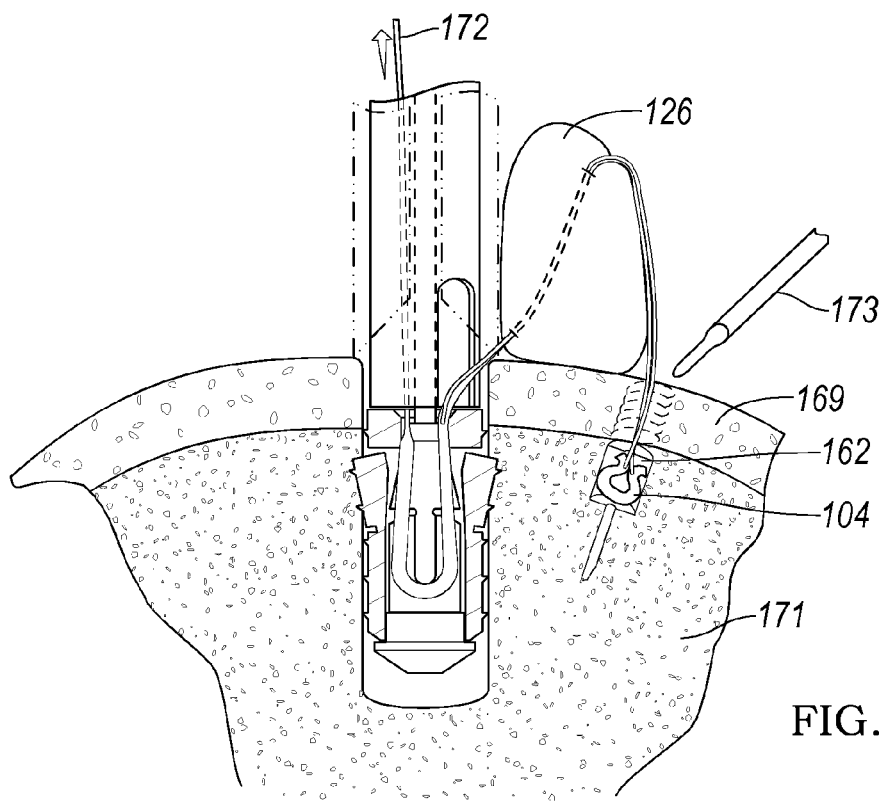

As shown in FIG. 43, the collapsible tube 104 of suture anchor is passed through passage 167 and into the cavity 162. In this regard, an insertion tool 173 can be used to insert the collapsible tube 104 into the cavity 162. As shown in FIG. 44, tension is applied to the end 172 of the suture anchor, thus causing the collapsible portion 104 of the anchor.

Figure 45:
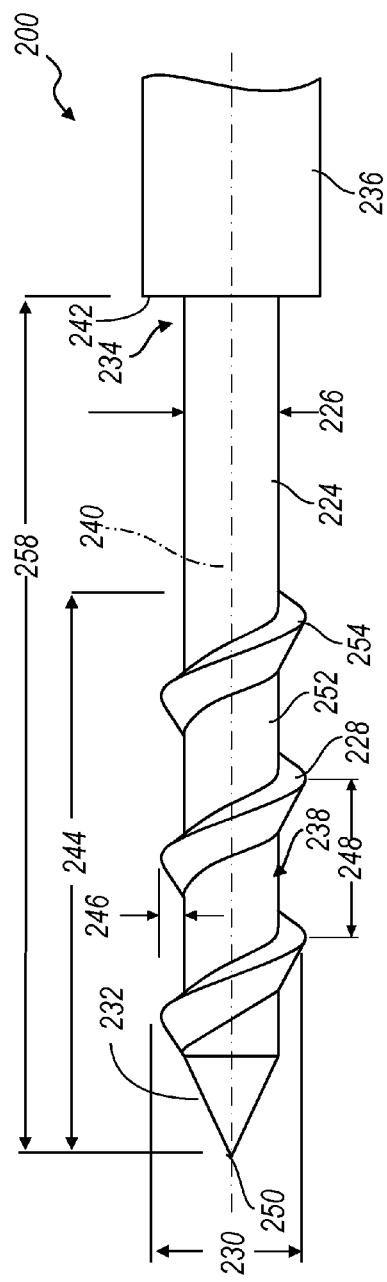
FIG. 45 is a side view of a bone cutting device constructed in accordance with the teachings of the present disclosure.
Figure 46:
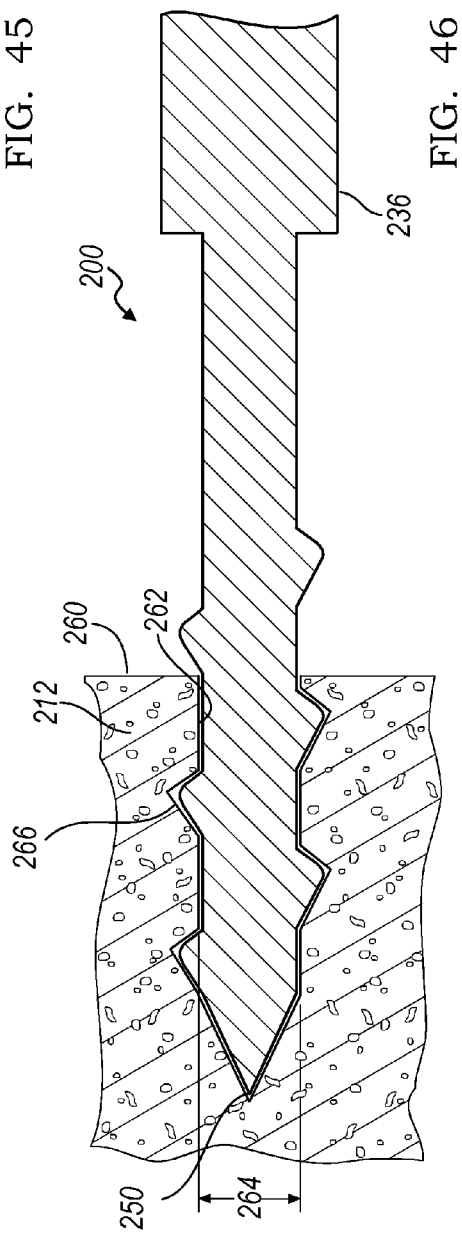
FIG. 46 is a cross-sectional view of the bone cutting device of FIG. 45 in an initial operative position in association with a bone of a body.
Figure 51:
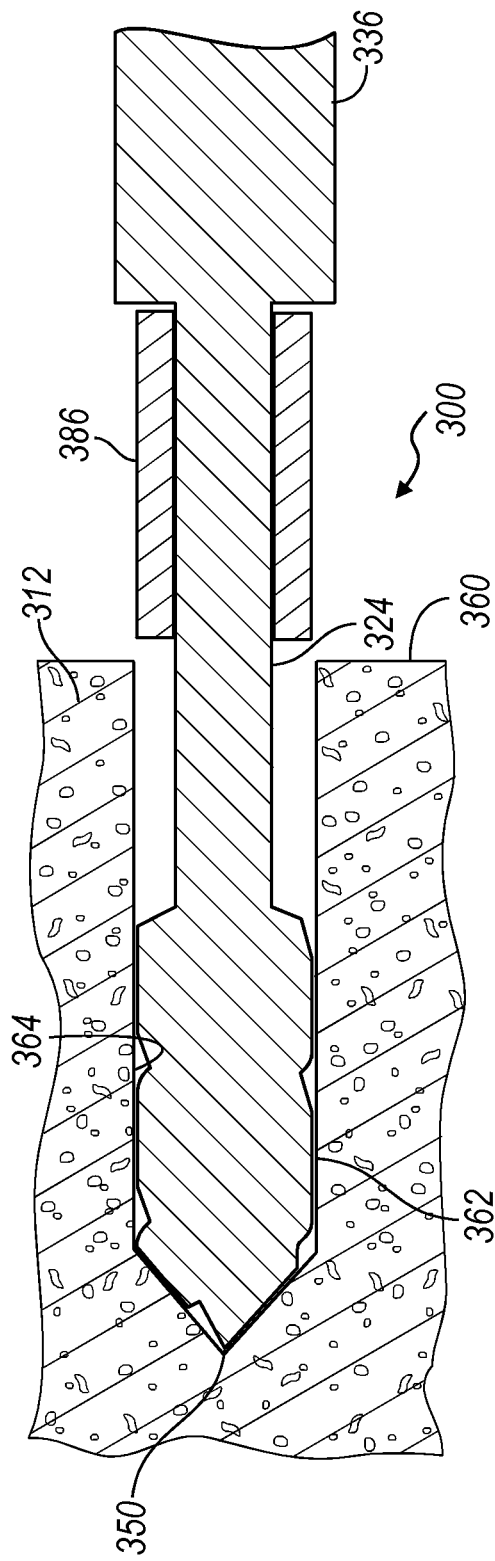
FIG. 51 is a cross-sectional view of the bone cutting device of FIG. 49 in an intermediate operative position in association with the bone of the body.

Referring now to FIGS. 45-47 of the drawings, an alternate bone cutting tool is generally indicated by reference number 200. Bone cutting tool 200 can be any tool operable for forming an open- or closed-end bore having a shoulder in a bone 212 for receipt of a tissue-anchoring device (e.g., a tap as shown in FIGS. 45-47 or a drill as shown in FIGS. 49-60). An exemplary anchoring device is a soft or flexible suture anchor 214, such as the suture-anchoring device described in co-pending U.S. patent application Ser. Nos. 12/915,962 and 11/935,681, both incorporated herein by reference. Soft suture anchor 214 is operable for securing a tissue 216 (e.g., xenograft, allograft, or bone) to bone 212 (see FIG. 48). Soft suture anchor 214 is illustrated to include a bone fixation element 218 and a tissue fixation element 220 interconnected through a suture 222, as will be described below. Those skilled in the art will understand that soft suture anchor 214 may be formed from a non-resorbable material or a resorbable material of the types that are well known in the art so as to permit bone fixation element 218, tissue fixation element 220, and suture 222 to bioabsorb over a selected time span, such as within the time span of the healing process.

With particular reference to FIG. 45, bone cutting tool 200 is shown to include an elongated body or shaft portion 224 having a first diameter 226, at least one distally positioned helical cutting tooth or flute 228 defining a second diameter 230, and a distal tapered end 232. Body portion 224 includes a proximal end 234 configured for receipt by a driving device 236 (e.g., a handle or a chuck of a power drill) and a distal end 238 forming helical cutting tooth 228 and terminating at tapered end 232. Helical cutting tooth 228 can be formed by machining the distal end 238 or otherwise connecting the tooth 228 to the distal end 238. Body portion 224 extends along a longitudinal axis 240 and is configured so as to provide first diameter 226 as a constant over its length. Alternately, body portion 224 may have a varied diameter so as to form an integral shoulder portion (not shown) at the proximal end 234 for receiving an external driving means (e.g., driving device 236). Driving device 236 has a larger size than that of first diameter 226, thereby forming a stop 242 therebetween that can act as a stop or depth limiter.

Helical cutting tooth 228 is coupled to body portion 224 and may extend therefrom by a predetermined length 244, width 246, and pitch 248. For example, helical cutting tooth 228 may extend by length 244 from a distal most tip 250 of tapered end 232 towards proximal end 234. Width 246 may correspond to a distance between an outer surface 252 of body portion 224 and an apex 254 of tooth 228. Accordingly, the second diameter 230 of bone cutting tool 200 may be larger than the first diameter 226 of body portion 224. Notably, predetermined length 244, width 246, and pitch 248 can be varied to provide an appropriately dimensioned bone pocket 256 for receipt of soft suture anchor 214, to accommodate varying bone constructs and densities. Additionally, body portion 224 may have a length 258 extending from distal most tip 250 to stop 242 for establishing the location of bone pocket 256 within the bone 212. For example, length 244 may be 5.0 to 15.0 mm, width 246 may be 0.5 to 1.0 mm, pitch 248 may be 2.0 to 4.0 mm, and length 258 may be 10.0 to 20.0 mm.

Referring now to FIGS. 46-48, the foregoing bone cutting tool 200 may be used to form a blind bore, concavity, or hole having a substantially uninterrupted 360° internal shoulder 272 within bone 212. In particular, distal most tip 250 is brought into contact with an outer surface 260 of bone 212. Bone cutting tool 200 is rotated around longitudinal axis 240 by manipulation of driving device 236. Bone cutting tool 200 gradually moves or is driven into and through outer surface 260 of bone 212 by the cutting action of helical cutting tooth 228. Helical cutting tooth 228 pulls bone cutting tool 200 into bone 212 in a corkscrew motion designed to draw the bone cutting tool 200 inwardly. It should be understood that bone cutting tool 200 is designed to penetrate cortical bone and establish bone pocket 256 within either cancellous or cortical bone. It should be noted, however, that bone cutting tool 200 may be sized to provide bone pocket 256 completely within cortical bone. In either case, bone cutting tool 200 produces a hole, concavity, or blind bore 262 within bone 212 having an inner diameter 264 that corresponds to first diameter 226. Bone cutting tool 200 proceeds inwardly of bone 212 until stop 242 meets outer surface 260.

Helical cutting tooth 228 establishes a single helical groove 266 in cylindrical bore 262 during inward rotation, as can be seen in FIG. 2. Single helical groove 266 extends from outer surface 260 to the beginning of distal tapered end 232 when the bone cutting tool 200 is at the predetermined desired depth into the bone 212. Without removing bone cutting tool 200 from bore 262, bone cutting tool 200 is then repeatedly or continuously rotated around longitudinal axis 240 by manipulation of driving device 236, so as to mill out bone pocket 256. The continuous rotation bores a portion of bone 212 to a second, inner diameter 268 about equivalent to the distance from opposing-facing apices 254 of tooth 228, as can be seen in FIG. 47. In other words, the bone cutting tool 200 is continuously rotated at the predetermined depth to establish the enlarged bone pocket 256 at the distal end of the bore 262. The inner diameter 268 of the bone pocket 256 is diametrically greater than the size of the inner diameter 264 of the bore 262. Bone cutting tool 200 is then slowly backed out of bone 212 leaving bore 262 terminating at bone pocket 256. In order to back bone cutting tool 200 out of bone 212, helical cutting tooth 228 may be brought back into engagement with the helical groove 266 in the bore 262. This may be achieved by putting slight back pressure on driving device 236, so as to allow helical cutting tooth 228 to catch on the single helical groove 266 in the cylindrical bore 262. The bone cutting tool 200 is then rotated around the longitudinal axis 240, but in reverse. Alternatively, a second helix form may be established during outward rotation of bone cutting tool 200 (not shown).

As can be seen in FIG. 48, bone pocket 256 includes a tapered cone 270 corresponding in shape and size to distal most tip 250, inner diameter 268 corresponding to the second diameter 230, and a substantially uninterrupted 360° shoulder 272 defined between the bore 262 and the bone pocket 256. Tapered cone 270 may terminate at a location within the bone 212 corresponding in length to the distance between stop 242 and distal most tip 250, or in other words length 258 (e.g., 15.0 mm). Shoulder 272 may be located within the bone 212 at a distance from outer surface 260 at a dimension equal to the difference between length 258 and length 244 (e.g., 5.0 mm).

Bone pocket 256 is sized to receive a deformable fixation device, such as soft suture anchor 214. It should be understood that while one exemplary soft suture anchor 214 is described herein, other anchoring devices are contemplated. For example, soft anchors having a single suture extending therethrough or rigid anchors, may be used. Soft suture anchor 214 can be preformed to include a looped configuration having at least one looped suture 222 and a pair of flexible anchors or bone fixation element 218 and tissue fixation element 220, as described in co-pending U.S. patent application Ser. No. 12/915,962, incorporated herein by reference. In one example as shown herein, looped suture 222 may traverse a path from one end of bone fixation element 218 to the other end thereof. Soft suture anchor 214 can be formed by passing a first suture end 274 through a first aperture 276 in bone fixation element 218 and out a second aperture 278 in bone fixation element 218. A second end 280 is then passed in through second aperture 278 in bone fixation element 218 and out first aperture 276 in bone fixation element 218. Passing ends 274, 280 through apertures 276, 278 can form looped suture 222. Similarly, ends 274, 280 are passed through apertures 282, 284 of tissue fixation element 220.

The soft suture anchor 214 has a first configuration during installation and a second configuration upon applying tension to first and second ends 274, 280. In particular, the configuration of the looped suture 222 can be placed in a desired tension to engage shoulder 272. Tension in looped suture 222 can cause constriction throughout soft suture anchor 214. This constriction can cause soft suture anchor 214 to "automatically" lock in a compressed configuration. Further tension on ends 274, 280 causes tissue 216 to be brought into engagement with outer surface 260 of bone 212. This can fix selected tissue 216 (e.g., a ligament) to bone 212 in which the bone pocket 256 is formed.

With reference now to FIGS. 49-53, another alternative bone cutting tool 300 is shown. Bone cutting tool 300 is also operable for preparing a bone 312 for receipt of a tissue anchoring device, such as soft suture anchor 214, as previously described. Soft suture anchor 214 is not described in conjunction with bone cutting tool 300; however, its insertion within a bone pocket 356 is similar to that described with reference to bone cutting tool 200 and bone pocket 256 as shown in FIG. 48.

With particular reference to FIG. 49, bone cutting tool 300 is shown to include a shaft or body portion 324, a tubular sleeve 386, and a tapered drill end 332. Body portion 324 includes a proximal end 334 configured for receipt of a driving device 336 (e.g., a handle, a chuck of a power drill) and a distal end 338 supporting tapered drill end 332. While body portion 324 is described as receiving driving device 336, it should be understood that distal end 338 may also terminate in an expanded shoulder (not shown) capable of insertion within a chuck (not shown) of the driving device 336. Furthermore, driving device 336 may be an integral piece used as a depth stop and also as a pivot point when maneuvering the drill (see FIG. 52A).

Tapered drill end 332 of bone cutting tool 300 may terminate at a distal most tip 350. Tapered drill end 332 can include cutting teeth or flutes 328 for axial and/or transverse cutting. Tapered drill end 332 may be self-tapping, so as to omit the need for a second, preparatory tool. Body portion 324 is situated along a longitudinal axis 340 and is configured to have a constant shaft diameter 326 over its length. Body portion 324 may be formed from a rigid material (e.g., stainless steel) or may be a more elastic material (e.g., nitinol).

Sleeve 386 may have a predetermined length 344, outer diameter 346, and concentric inner diameter 348 and may be slidingly coupled to body portion 324. Length 344 and outer diameter 346 of sleeve 386 may correspond to a selected depth and width of cut in bone 312, as outer diameter 346 of sleeve 386 is approximately equal to an outer diameter 330 of tapered drill end 332. Notably, predetermined length 344 and outer diameter 346 can be varied to provide an appropriately dimensioned bone pocket 356 for receipt of soft suture anchor 214, to accommodate varying bone constructs and densities. Inner diameter 348 may be slightly larger than shaft diameter 326, so as to allow sleeve 386 to glide over body portion 324 during use. Sleeve 386 may be a rigid material (e.g., stainless steel), so as to provide stiffness to body portion 324 during insertion into bone 312. Sleeve 386 may also work as a centralized cutting guide for bone cutting tool 300 during insertion into bone 312, as will be described in detail below.

Referring now to FIGS. 50-53, the foregoing bone cutting tool 300 may be used to form an undercut or shoulder 372 in bone 312. In particular, distal most tip 350 is brought into contact with an outer surface 360 of bone 312. Bone cutting tool 300 is rotated around longitudinal axis 340 by manipulation of driving device 336. Gradually, bone cutting tool 300 moves into and through outer surface 360 of bone 312 by the cutting action of tapered drill end 332. Bone cutting tool 300 produces a bore 362 within bone 312 having an inner diameter 364 that corresponds to the outer diameter 330 of tapered drill end 332 and outer diameter 346 of sleeve 386. Bone cutting tool 300 advances inwardly of bone 312 until a desired cutting depth is reached.

Sleeve 386 is then retracted from bore 362 within bone 312. Bone cutting tool 300 can then be further rotated by manipulation of driving device 336. As body portion 324 and tapered drill end 332 are no longer supported by sleeve 386, they are allowed to freely move within bore 362. The movement can be either randomized or can be cyclical as performed by a user, but is typically defined as a pivot of the body portion 324 near the entrance to the bore 362. The side or transverse cutting flutes 328 allow cutting of bone 312 transverse to the axis 340.

Figure 52A:
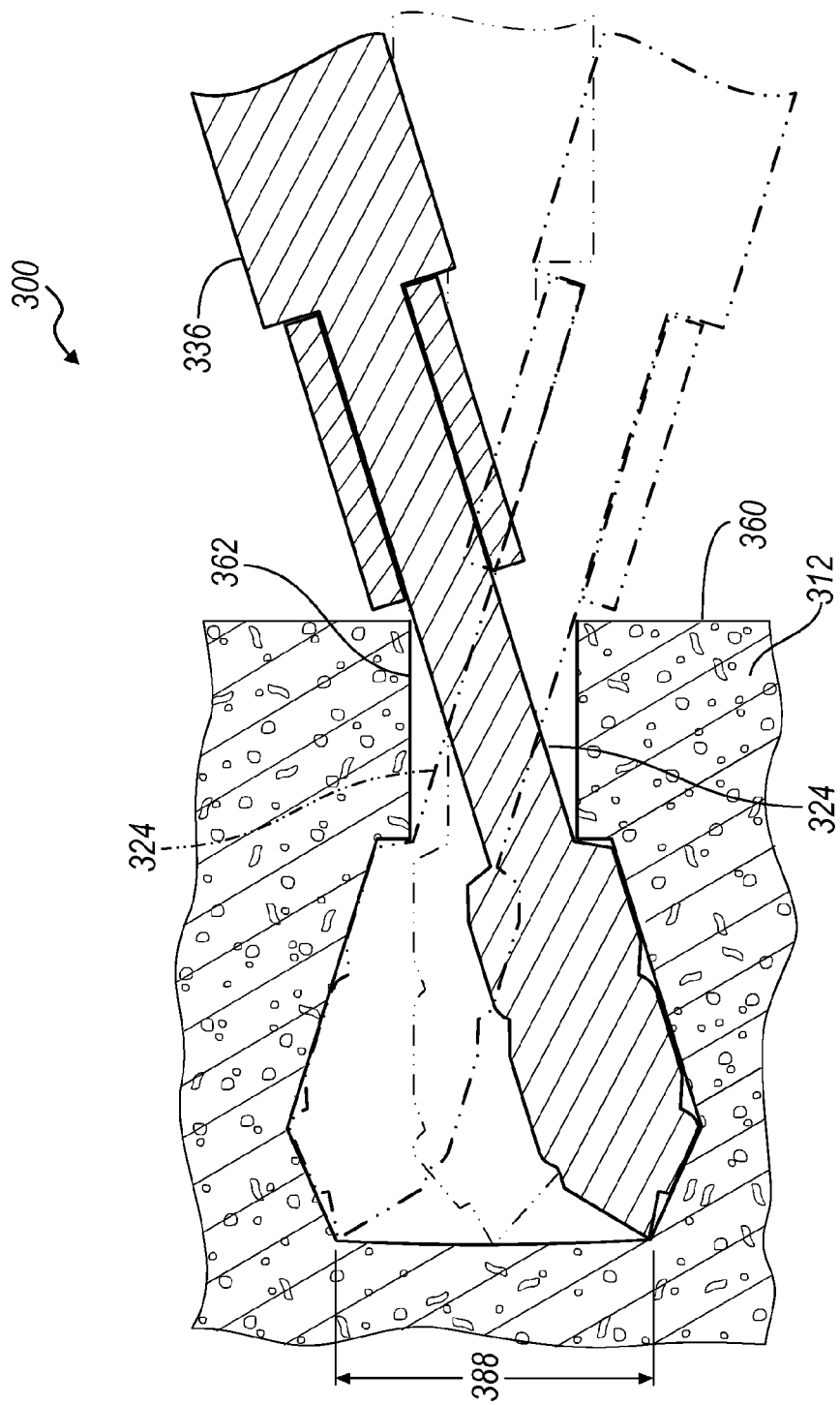
FIG. 52A is a cross-sectional view of the bone cutting device of FIG. 49 in a final operative position in association with the bone of the body and having a rigid body portion.
Figure 52B:
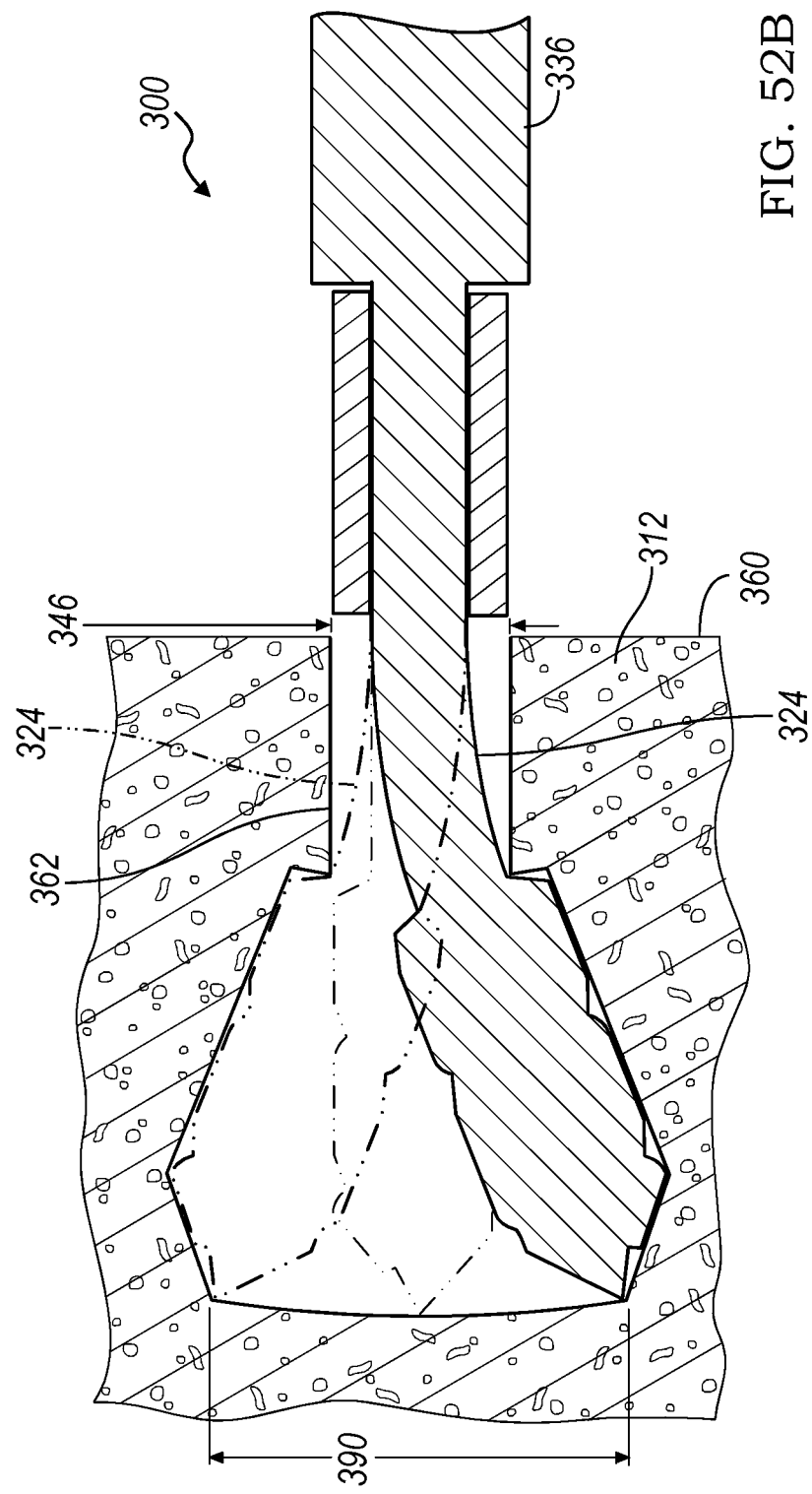
FIG. 52B is a cross-sectional view similar to that of FIG. 52A having a flexible body portion.

It should be understood that when body portion 324 can be formed from an elastic material, the range of tapered drill end 332 may be greater than when body portion 324 is formed from a rigid material. For example, FIG. 52A shows body portion 324 formed from a rigid material, while FIG. 52B shows body portion 324 formed from an elastic material. As can be seen, a diametrical range 388 of tapered drill end 332 in FIG. 52A is smaller than that of a diametrical range 390 of tapered drill end 332 in FIG. 52B. While body portion 324 is described and illustrated as a straight shaft, it should be understood that body portion 324 may also be formed to include a multi-piece pivoting arrangement (e.g., a pivot driver). In this way, body portion 324 may include an elbow (not shown) at a midpoint thereof. The elbow can allow the body portion 324 to flex in a mode similar to that shown in FIG. 52B. Therefore, size of bone pocket 356 is directly related to material and/or configuration of body portion 324. Bone cutting tool 300 may then be oriented with bore 362 and then backed out of bone 312. In this way, all cutting operations are performed without removing bone cutting tool 300 from bore 362.

Figure 53:
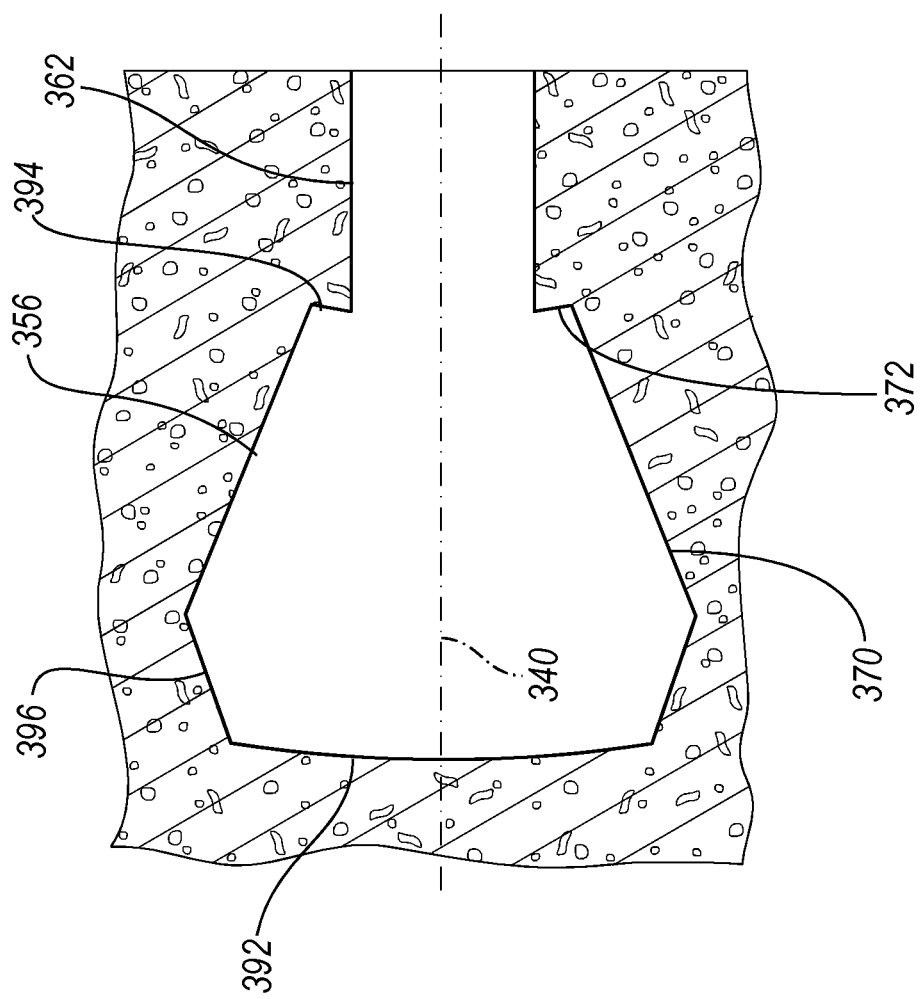
FIG. 53 is a cross-sectional view of a bone socket established by the bone cutting device of FIG. 49.

As can be seen in FIG. 53, bore 362 terminates at bone pocket 356. Bone pocket 356 includes a widened socket 370 including an arc-shaped distal end 392 and a convex shoulder 372 forming a circumferential tooth 394. The arc-shaped distal end 392 corresponds to the path of cutting of the distal most tip 350. The arc-shaped distal end 392 may be adjacent to an angled side 396 corresponding to the profile of the tapered drill end 332. The angled side 396 may extend around a periphery of the arc-shaped distal end 392 and may terminate at the circumferential tooth 394 of the convex shoulder 372. The convex shoulder 372 may extend 360° around the periphery of the bore 362 between the widened socket 370 and the bore 362. While the bone pocket 356 is shown with a symmetrical arrangement, it should be understood that the bone pocket 356 may also have an asymmetrical arrangement dictated by the cyclical movement of the bone cutting tool 300. In either case, however, bone pocket 356 is sized to receive soft suture anchor 214, as previously described. It should be understood that the selection of shaft material may be directly related to the size of the suture anchor to be inserted within the bone pocket 356. For example, the larger size of the bone pocket 356 obtained with a flexible material may be necessary for larger suture anchors.

With reference now to FIGS. 54-60, an alternative bone cutting tool 400 is shown. Bone cutting tool 400 is also operable for preparing a bone 412 for receipt of a tissue anchoring device, such as soft suture anchor 214, as previously described. Soft suture anchor 214 is not described in conjunction with bone cutting tool 400; however, its insertion within a bone pocket 456 is similar to that described with reference to bone cutting tool 200 and bone pocket 256 as shown in FIG. 48.

With particular reference to FIG. 54, bone cutting tool 400 is shown to include a body portion 424, a sleeve 486, and a tapered drill end 432. Body portion 424 includes a proximal end 434 configured for receipt of a driving device 436 (e.g., a handle, a chuck of a power drill) and a distal end 438 supporting tapered drill end 432. Tapered drill end 432 of bone cutting tool 400 may terminate at a distal most tip 450. Body portion 424 extends along a longitudinal axis 440 and is configured to have a constant shaft diameter 426 over its length. Body portion 424 may be formed from a rigid material (e.g., stainless steel).

Sleeve 486 may have a predetermined length 444 and outer diameter 446. Sleeve 486 may also have a non-concentric or offset inner aperture 448, a flange 498, and a chamfered end 499. Length 444 of sleeve 486 may correspond to a selected depth of cut in bone 412 with flange 498 limiting movement of sleeve 486, as will be described in more detail below. Outer diameter 446 may correspond to an outer diameter 430 of tapered drill end 432. Furthermore, inner aperture 448 may be slightly larger than shaft diameter 426 so as to allow sleeve 486 to glide over body portion 424 during use. As should be understood, diameters 430, 446 and location of offset inner aperture 448 can be varied to provide an appropriately dimensioned bone pocket 456 for receipt of soft suture anchor 214, to accommodate varying bone constructs and densities.

Referring now to FIGS. 55-59, the foregoing bone cutting tool 400 may be used to form an undercut in bone 412 with sleeve 486 working as a guide for cutting bone pocket 456 after insertion to appropriate depth into bone 412. In particular, distal most tip 450 is brought into contact with an outer surface 460 of bone 412, while sleeve 486 is located at a position away from the tapered drill end 432. Bone cutting tool 400 is rotated around longitudinal axis 440 by manipulation of driving device 436. Gradually, bone cutting tool 400 moves into and through outer surface 460 of bone 412 by the cutting action of tapered drill end 432. Bone cutting tool 400 may establish a bore 462 within bone 412 having an inner diameter 464 that corresponds to the outer diameter 430 of tapered drill end 432. Bone cutting tool 400 advances inwardly of bone 412 until an appropriate cutting depth is reached.

Chamfered end 499 of sleeve 486 is then inserted into bore 462. Continuous rotation of bone cutting tool 400 by manipulation of driving device 436, while simultaneously applying axial and rotational force to sleeve 486, causes eccentric rotation of tapered drill end 432 allowing the sleeve 486 to be inserted into the bore 462. Movement of sleeve 486 into bore 462 forces body portion 424 and tapered drill end 432 to cut into bore 462 in a spiraled offset manner. Sleeve 486 is prevented from moving further into bone 412 by flange 498. As bone 412 is removed from bore 462, a bone pocket 456 is formed having a 360° shoulder 472 therewith. Each rotation of tapered drill end 432 causes sleeve 486 to more freely move within bore 462. Accordingly, tapered drill end 432 begins to move freely within bore 462, but only to the extent permitted by the dimensional offset of inner aperture 448.

As can be seen in FIG. 58, bone cutting tool 400 is then centered and reversed out of bore 462 and bone 412. Bone pocket 456 includes a widened socket 470 and 360° shoulder 472, corresponding in shape and size to tapered drill end 432. Bone pocket 456 is sized to receive soft suture anchor 214, as previously described.

With reference now to FIG. 60, an alternate sleeve 586 is shown for attachment to the bone cutting tool 400. Sleeve 586 includes an offset inner aperture 548 and a flange 598, which function as described above. Accordingly, alternative sleeve 586 is similar to the sleeve 486 of FIGS. 54-59, but does not include chamfered end 499. When sleeve 586 is in use, bone cutting tool 400 may be manually angled to allow for insertion of sleeve 586 into bore 462.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Further, the suture material and collapsible tubes can be formed of resorbable material. Such variations are not to be regarded as a departure from the spirit and scope of the invention.

What is claimed is:

1. A method for attaching a fixation device to a bone, the method comprising:
    bringing a bone cutting tool that extends along a longitudinal axis into engagement with an outer surface of the bone;
    rotating the bone cutting tool about the longitudinal axis while driving the bone cutting tool from the outer surface of the bone to a predetermined depth in the bone to form a bore;
    continuously rotating the bone cutting tool at the predetermined depth while maintaining the bone cutting tool in a substantially stationary position to establish an enlarged bone pocket at a distal end of the bore, the bone pocket defining a shoulder extending around a circumference between the bone pocket and the bore;
    removing the bone cutting tool from the bone pocket and the bore;
    inserting the fixation device into the bone pocket through the bore; and
    positioning the fixation device against the shoulder of the bone pocket.

2. The method of claim 1, wherein continuously rotating the bone cutting tool is performed without removing the bone cutting tool from the bore and after rotating the bone cutting tool into position at the predetermined depth.

3. The method of claim 1, wherein rotating the bone cutting tool about the longitudinal axis pulls the bone cutting tool into the bore.

4. The method of claim 3, further comprising:
    creating a helical groove relative to the bore as the bone cutting tool is rotating about the longitudinal axis.

5. The method of claim 3, wherein rotating the bone cutting tool about the longitudinal axis is performed until a stop at a proximal end of the bone cutting tool engages the outer surface of the bone.

6. The method of claim 1, further comprising:
    removing the bone at the distal end of the bore to form the bone pocket by the continuously rotating the bone cutting tool at the predetermined depth.

7. The method of claim 1, wherein rotating the bone cutting tool about the longitudinal axis includes forming a first aperture in the bone with a portion of the bone cutting tool having a first diameter.

8. A method for attaching a fixation device to a bone, the method comprising:
    bringing a bone cutting tool having a helical flute into engagement with an outer surface of the bone;
    rotating the bone cutting tool about a longitudinal axis to form a first bore having a helical flute groove extending from the outer surface of the bone to a depth within the bone;
    continuously rotating the bone cutting tool at the depth to establish a second bore having a shoulder and a continuous sidewall, the shoulder extending around a circumference between the second bore and the first bore;
    aligning the bone cutting tool with the first bore;
    drawing the bone cutting tool out of the second and first bores;
    inserting the fixation device into the second bore through the first bore; and
    positioning the fixation device against the shoulder of the second bore.

9. The bone cutting tool of claim 8, wherein continuously rotating the bone cutting tool is performed while maintaining the bone cutting tool in a substantially stationary position without removing the bone cutting tool from the first bore.

10. The bone cutting tool of claim 8, wherein rotating the bone cutting tool about the longitudinal axis pulls the bone cutting tool into the bore.

11. The bone cutting tool of claim 10, wherein rotating the bone cutting tool about the longitudinal axis is performed until a stop at a proximal end of the bone cutting tool engages the outer surface of the bone.

12. The method of claim 8, further comprising:
transversely cutting the bone while maintaining the bone cutting tool in a substantially stationary position to establish the second bore.

13. The method of claim 8, wherein aligning the bone cutting tool with the first bore further comprises reverse rotating the bone cutting tool to prevent further bone removal as the bone cutting tool is drawn out of the second and first bores along the helical flute groove formed in the first bore.

14. A method for attaching a fixation device to a bone, the method comprising:
advancing a bone cutting tool through cortical bone about a longitudinal axis of the tool to a predetermined depth in cancellous bone to form a bore having a helical groove, the bone cutting tool including
a body portion extending from a proximal end to a distal end along the longitudinal axis,
a first member extending radially outwardly from the distal end of the body portion, the first member having a first diameter defined by at least one transverse cutting flute, and
a second member extending radially outwardly from the body portion proximal the first member and having a second diameter greater than the first diameter; and
continuously rotating the bone cutting tool at a substantially stationary position at the predetermined depth to establish an enlarged bone pocket having a cylindrical sidewall at a distal end of the bore, the bone pocket defining a shoulder extending around a circumference between the bone pocket and the bore.

15. The method of claim 14, further comprising:
removing the bone cutting tool from the bone pocket and the bore;
inserting the fixation device into the bone pocket through the bore; and
positioning the fixation device against the shoulder of the bone pocket.

16. The method of claim 14, wherein the second member is a stop extending radially outwardly from the body portion at the proximal end, the stop engaging an outer surface of the cortical bone for establishing the predetermined depth in the cancellous bone.

17. The method of claim 14, wherein the second member is a threaded portion sized for forming the enlarged bone pocket.

18. The bone cutting tool of claim 14, wherein continuously rotating the bone cutting tool is performed without removing the bone cutting tool from the bore and after rotating the bone cutting tool into position at the predetermined depth.

19. The bone cutting tool of claim 14, wherein rotating the bone cutting tool about the longitudinal axis includes forming a first aperture in the bone with the first member of the bone cutting tool.

20. The bone cutting tool of claim 19, wherein continuously rotating the bone cutting tool forms the bone pocket having a pocket diameter substantially equal to the second diameter of the second member.

* * * * *